United States Patent
Lim et al.

(10) Patent No.: US 11,306,141 B2
(45) Date of Patent: Apr. 19, 2022

(54) ANTIBODY AGAINST HUMAN DLK1 AND USE THEREOF

(71) Applicant: Y-BIOLOGICS INC., Daejeon (KR)

(72) Inventors: Jung Chae Lim, Daejeon (KR); Ji-Young Shin, Daejeon (KR); Sunha Yoon, Daejeon (KR); Sang Pil Lee, Daejeon (KR); Yunseon Choi, Daejeon (KR); Jisu Lee, Sejong (KR); Young-Gyu Cho, Daejeon (KR); Seok Ho Yoo, Daejeon (KR); Yeung chul Kim, Daejeon (KR); Si Hyung Lee, Daejeon (KR); Jae Eun Park, Sejong (KR); Youngja Song, Daejeon (KR); Gi Sun Baek, Daejeon (KR); Bum-chan Park, Daejeon (KR); Young Woo Park, Daejeon (KR)

(73) Assignee: Y-BIOLOGICS INC., Daejeon (KR)

( * ) Notice: Subject to any disclaimer, the term of this patent is extended or adjusted under 35 U.S.C. 154(b) by 86 days.

(21) Appl. No.: 16/644,764

(22) PCT Filed: Sep. 10, 2018

(86) PCT No.: PCT/KR2018/010559
§ 371 (c)(1),
(2) Date: Mar. 5, 2020

(87) PCT Pub. No.: WO2019/050362
PCT Pub. Date: Mar. 14, 2019

(65) Prior Publication Data
US 2021/0214432 A1    Jul. 15, 2021

(30) Foreign Application Priority Data
Sep. 8, 2017    (KR) .................. 10-2017-0115263

(51) Int. Cl.
C07K 16/28    (2006.01)
A61K 47/68    (2017.01)
A61P 35/00    (2006.01)
C07K 14/705   (2006.01)

(52) U.S. Cl.
CPC .......... *C07K 16/28* (2013.01); *A61K 47/6801* (2017.08); *A61P 35/00* (2018.01); *C07K 14/705* (2013.01)

(58) Field of Classification Search
CPC .. C07K 16/28; C07K 14/705; A61K 47/6801; A61P 35/00
See application file for complete search history.

(56) References Cited

U.S. PATENT DOCUMENTS

| 8,017,118 B2 | 9/2011 | Nakamura et al. |
| 2014/0072558 A1 | 3/2014 | Park et al. |
| 2015/0030595 A1 | 1/2015 | Lee et al. |

FOREIGN PATENT DOCUMENTS

| JP | 2012513775 A | 6/2012 |
| KR | 10-2009-0088893 A | 8/2009 |
| KR | 10-0982170 B1 | 9/2010 |
| KR | 10-2012-0113175 A | 10/2012 |
| KR | 10-20120113174 A | 10/2012 |
| KR | 10-2017-0051579 A | 5/2017 |
| WO | 2008056833 A1 | 5/2008 |
| WO | 2009116670 A1 | 9/2009 |
| WO | 2012138102 A2 | 10/2012 |
| WO | 2014054820 A1 | 4/2014 |

OTHER PUBLICATIONS

Vajdos et al, Comprehensive Functional Maps of the Antigen-binding Site of an Anti-ErbB2 Antibody Obtained with Shotgun Scanning Mutagenesis. J. Mol. Biol. 320:415-428, 2002.*
Wu, C. et al., "In vivo far-red luminescence imaging of a biomarker based on BRET from Cypridina bioluminescence to an organic dye", PNAS, vol. 106(37), Sep. 15, 2009, 15599-15603.
Yanai, H. et al., "Dlk-1, a cell surface antigen on foetal hepatic stem/progenitor cells, is expressed in hepatocellular, colon, pancreas and breast carcinomas at a high frequency", J. Biochem., 148(1), doi:10.1093/jb/mvq034, Mar. 30, 2010, 85-92.
English Translation of Office Action dated Apr. 20, 2021 for JP Application No. 2020-514200.
Begum, A., et al., "DLK1, delta-like 1 homolog (Drosophila), regulates tumor cell differentiation in vivo," Cancer Letters, 318:26-33 (2012).
EESR dated Sep. 15, 2021 in EP Application No. 18853205.5.
Bujak, E. et al., "A Monoclonal Antibody to Human DLK1 Reveals Differential Expression in Cancer and Absence in Healthy Tissues", Antibodies, 4, doi:10.3390/antib4020071, Apr. 16, 2015, 71-87.

* cited by examiner

*Primary Examiner* — Ruixiang Li
(74) *Attorney, Agent, or Firm* — Elmore Patent Law Group, P.C.; Joseph C. Zucchero; Carolyn S. Elmore

(57) ABSTRACT

The present invention relates to an antibody against delta-like 1 homolog (*Drosophila*) (DLK1) or an antigen-binding fragment thereof, a nucleic acid encoding the same, a vector comprising the nucleic acid, a cell transformed with the vector, a method for producing the antibody or an antigen-binding fragment thereof, an antibody drug conjugate (ADC) comprising the same, a pharmaceutical composition for treating cancer, a composition for diagnosing cancer, and a chimeric antigen receptor (CAR) and a T-cell engager comprising the same.

17 Claims, 20 Drawing Sheets

Specification includes a Sequence Listing.

```
                          SEQUENCE LISTING

<160> NUMBER OF SEQ ID NOS: 128

<210> SEQ ID NO 1
<211> LENGTH: 25
<212> TYPE: PRT
<213> ORGANISM: Artificial Sequence
<220> FEATURE:
<223> OTHER INFORMATION: Human anti-DLK1 antibody framework

<400> SEQUENCE: 1

Gln Val Gln Leu Val Glu Ser Gly Gly Thr Leu Val Gln Pro Gly Gly
1               5                   10                  15

Ser Leu Arg Leu Ser Cys Ala Ala Ser
            20                  25

<210> SEQ ID NO 2
<211> LENGTH: 8
<212> TYPE: PRT
<213> ORGANISM: Artificial Sequence
<220> FEATURE:
<223> OTHER INFORMATION: Human anti-DLK1 antibody CDR

<400> SEQUENCE: 2

Gly Phe Thr Phe Ser Ser His Ala
1               5

<210> SEQ ID NO 3
<211> LENGTH: 17
<212> TYPE: PRT
<213> ORGANISM: Artificial Sequence
<220> FEATURE:
<223> OTHER INFORMATION: Human anti-DLK1 antibody framework

<400> SEQUENCE: 3

Met Ser Trp Val Arg Gln Thr Pro Gly Lys Gly Leu Glu Trp Val Ser
1               5                   10                  15

Ser

<210> SEQ ID NO 4
<211> LENGTH: 8
<212> TYPE: PRT
<213> ORGANISM: Artificial Sequence
<220> FEATURE:
<223> OTHER INFORMATION: Human anti-DLK1 antibody CDR

<400> SEQUENCE: 4

Ile Thr Lys Ser Gly Ser Gly Thr
1               5

<210> SEQ ID NO 5
<211> LENGTH: 38
<212> TYPE: PRT
<213> ORGANISM: Artificial Sequence
<220> FEATURE:
<223> OTHER INFORMATION: Human anti-DLK1 antibody framework

<400> SEQUENCE: 5

Tyr Ser Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
```

<210> SEQ ID NO 6
<211> LENGTH: 13
<212> TYPE: PRT
<213> ORGANISM: Artificial Sequence
<220> FEATURE:
<223> OTHER INFORMATION: Human anti-DLK1 antibody CDR

<400> SEQUENCE: 6

Thr Arg Glu Gly Leu Gly Tyr Tyr Tyr Gly Met Asp Val
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Human anti-DLK1 antibody framework

<400> SEQUENCE: 7

Trp Gly Gln Gly Thr Thr Val Thr Val Ser Ser
1               5                   10

<210> SEQ ID NO 8
<211> LENGTH: 25
<212> TYPE: PRT
<213> ORGANISM: Artificial Sequence
<220> FEATURE:
<223> OTHER INFORMATION: Human anti-DLK1 antibody framework

<400> SEQUENCE: 8

Gln Leu Val Leu Thr Gln Pro Pro Ser Val Ser Gly Ala Pro Gly Gln
1               5                   10                  15

Arg Val Ile Ile Ser Cys Thr Gly Ser
            20                  25

<210> SEQ ID NO 9
<211> LENGTH: 9
<212> TYPE: PRT
<213> ORGANISM: Artificial Sequence
<220> FEATURE:
<223> OTHER INFORMATION: Human anti-DLK1 antibody CDR

<400> SEQUENCE: 9

Ser Ser Asn Ile Gly Ala Gly Tyr Asp
1               5

<210> SEQ ID NO 10
<211> LENGTH: 17
<212> TYPE: PRT
<213> ORGANISM: Artificial Sequence
<220> FEATURE:
<223> OTHER INFORMATION: Human anti-DLK1 antibody framework

<400> SEQUENCE: 10

Val His Trp Tyr Gln Gln Leu Pro Gly Thr Ala Pro Arg Leu Leu Ile
1               5                   10                  15

Tyr

<210> SEQ ID NO 11
<211> LENGTH: 3
<212> TYPE: PRT
<213> ORGANISM: Artificial Sequence
<220> FEATURE:
<223> OTHER INFORMATION: Human anti-DLK1 antibody CDR -continued

<400> SEQUENCE: 11

Gly Ser Thr
1

<210> SEQ ID NO 12
<211> LENGTH: 36
<212> TYPE: PRT
<213> ORGANISM: Artificial Sequence
<220> FEATURE:
<223> OTHER INFORMATION: Human anti-DLK1 antibody framework

<400> SEQUENCE: 12

Asn Arg Pro Ser Gly Val Pro Asp Arg Phe Ser Gly Ser Lys Ser Gly
1               5                   10                  15

Thr Ser Ala Ser Leu Ala Ile Thr Gly Leu Gln Ala Glu Asp Glu Ala
            20                  25                  30

Asp Tyr Tyr Cys
        35

<210> SEQ ID NO 13
<211> LENGTH: 12
<212> TYPE: PRT
<213> ORGANISM: Artificial Sequence
<220> FEATURE:
<223> OTHER INFORMATION: Human anti-DLK1 antibody CDR

<400> SEQUENCE: 13

Gln Ser Tyr Asp Asn Ser Leu Ser Ala His Tyr Val
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Human anti-DLK1 antibody framework

<400> SEQUENCE: 14

Phe Gly Thr Gly Thr Lys Val Thr Val Leu
1               5                   10

<210> SEQ ID NO 15
<211> LENGTH: 25
<212> TYPE: PRT
<213> ORGANISM: Artificial Sequence
<220> FEATURE:
<223> OTHER INFORMATION: Human anti-DLK1 antibody framework

<400> SEQUENCE: 15

Gln Val Gln Leu Val Gln Ser Gly Gly Ala Val Val Gln Pro Gly His
1               5                   10                  15

Ser Leu Arg Leu Ser Cys Glu Ala Ser
            20                  25

<210> SEQ ID NO 16
<211> LENGTH: 8
<212> TYPE: PRT
<213> ORGANISM: Artificial Sequence
<220> FEATURE:
<223> OTHER INFORMATION: Human anti-DLK1 antibody CDR

<400> SEQUENCE: 16

Gly Phe Lys Phe Lys Asp Tyr Gly
1               5

<210> SEQ ID NO 17
<211> LENGTH: 17
<212> TYPE: PRT
<213> ORGANISM: Artificial Sequence
<220> FEATURE:
<223> OTHER INFORMATION: Human anti-DLK1 antibody framework

<400> SEQUENCE: 17

Met His Trp Val Arg Gln Ala Pro Gly Lys Gly Leu Glu Trp Leu Ala
1               5                   10                  15

Val

<210> SEQ ID NO 18
<211> LENGTH: 8
<212> TYPE: PRT
<213> ORGANISM: Artificial Sequence
<220> FEATURE:
<223> OTHER INFORMATION: Human anti-DLK1 antibody CDR

<400> SEQUENCE: 18

Ile Ser His Asp Gly Arg Asn Lys
1               5

<210> SEQ ID NO 19
<211> LENGTH: 38
<212> TYPE: PRT
<213> ORGANISM: Artificial Sequence
<220> FEATURE:
<223> OTHER INFORMATION: Human anti-DLK1 antibody framework

<400> SEQUENCE: 19

Asn Tyr Ala Asp Ser Val Lys Gly Arg Leu Thr Ile Ser Arg Asp Asn
1               5                   10                  15

Ser Lys Asn Thr Leu Ser Phe Gln Met Asn Ser Leu Arg Ala Glu Asp
            20                  25                  30

Thr Ala Val Tyr Tyr Cys
        35

<210> SEQ ID NO 20
<211> LENGTH: 10
<212> TYPE: PRT
<213> ORGANISM: Artificial Sequence
<220> FEATURE:
<223> OTHER INFORMATION: Human anti-DLK1 antibody CDR

<400> SEQUENCE: 20

Val Arg Asp Trp Ser Tyr Ala Phe Asp Ile
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Human anti-DLK1 antibody framework

<400> SEQUENCE: 21

Trp Gly Gln Gly Thr Leu Val Thr Val Ser Ser
1               5                   10

<210> SEQ ID NO 22
<211> LENGTH: 26
<212> TYPE: PRT
<213> ORGANISM: Artificial Sequence

```
<220> FEATURE:
<223> OTHER INFORMATION: Human anti-DLK1 antibody framework

<400> SEQUENCE: 22

Asp Ile Gln Met Thr Gln Ser Pro Ser Phe Leu Ser Ala Ser Val Gly
1               5                   10                  15

Asp Arg Val Asn Ile Thr Cys Arg Ala Ser
            20                  25

<210> SEQ ID NO 23
<211> LENGTH: 6
<212> TYPE: PRT
<213> ORGANISM: Artificial Sequence
<220> FEATURE:
<223> OTHER INFORMATION: Human anti-DLK1 antibody CDR

<400> SEQUENCE: 23

Gln Asp Ile Ser Arg Arg
1               5

<210> SEQ ID NO 24
<211> LENGTH: 17
<212> TYPE: PRT
<213> ORGANISM: Artificial Sequence
<220> FEATURE:
<223> OTHER INFORMATION: Human anti-DLK1 antibody framework

<400> SEQUENCE: 24

Leu Ala Trp Tyr Gln Gln Lys Pro Gly Lys Ala Pro Lys Leu Leu Ile
1               5                   10                  15

Tyr

<210> SEQ ID NO 25
<211> LENGTH: 3
<212> TYPE: PRT
<213> ORGANISM: Artificial Sequence
<220> FEATURE:
<223> OTHER INFORMATION: Human anti-DLK1 antibody CDR

<400> SEQUENCE: 25

Gly Ala Ala
1

<210> SEQ ID NO 26
<211> LENGTH: 36
<212> TYPE: PRT
<213> ORGANISM: Artificial Sequence
<220> FEATURE:
<223> OTHER INFORMATION: Human anti-DLK1 antibody framework

<400> SEQUENCE: 26

Ser Leu Gln Ser Ala Val Ala Ser Arg Phe Ser Gly Ser Gly Ser Gly
1               5                   10                  15

Thr Glu Phe Thr Leu Thr Ile Ser Ser Leu Gln Pro Glu Asp Phe Ala
            20                  25                  30

Asn Tyr Tyr Cys
            35

<210> SEQ ID NO 27
<211> LENGTH: 9
<212> TYPE: PRT
<213> ORGANISM: Artificial Sequence
<220> FEATURE:
<223> OTHER INFORMATION: Human anti-DLK1 antibody CDR
```

<400> SEQUENCE: 27

Gln Gln Ile Tyr Thr Thr Pro Leu Thr
1               5

<210> SEQ ID NO 28
<211> LENGTH: 10
<212> TYPE: PRT
<213> ORGANISM: Artificial Sequence
<220> FEATURE:
<223> OTHER INFORMATION: Human anti-DLK1 antibody framework

<400> SEQUENCE: 28

Phe Gly Gly Gly Thr Lys Val Glu Ile Lys
1               5                   10

<210> SEQ ID NO 29
<211> LENGTH: 25
<212> TYPE: PRT
<213> ORGANISM: Artificial Sequence
<220> FEATURE:
<223> OTHER INFORMATION: Human anti-DLK1 antibody framework

<400> SEQUENCE: 29

Gln Met Gln Leu Val Gln Ser Gly Gly Gly Leu Val Gln Pro Gly Arg
1               5                   10                  15

Ser Leu Arg Leu Ser Cys Ala Ala Ser
            20                  25

<210> SEQ ID NO 30
<211> LENGTH: 8
<212> TYPE: PRT
<213> ORGANISM: Artificial Sequence
<220> FEATURE:
<223> OTHER INFORMATION: Human anti-DLK1 antibody CDR

<400> SEQUENCE: 30

Gly Phe Thr Phe Asp Asp Tyr Ala
1               5

<210> SEQ ID NO 31
<211> LENGTH: 17
<212> TYPE: PRT
<213> ORGANISM: Artificial Sequence
<220> FEATURE:
<223> OTHER INFORMATION: Human anti-DLK1 antibody framework

<400> SEQUENCE: 31

Met His Trp Val Arg Gln Ala Pro Gly Lys Gly Leu Glu Trp Val Ser
1               5                   10                  15

Gly

<210> SEQ ID NO 32
<211> LENGTH: 8
<212> TYPE: PRT
<213> ORGANISM: Artificial Sequence
<220> FEATURE:
<223> OTHER INFORMATION: Human anti-DLK1 antibody CDR

<400> SEQUENCE: 32

Ile Ser Trp Asn Ser Gly Ser Ile
1               5

<210> SEQ ID NO 33
<211> LENGTH: 38
<212> TYPE: PRT

```
<213> ORGANISM: Artificial Sequence
<220> FEATURE:
<223> OTHER INFORMATION: Human anti-DLK1 antibody framework

<400> SEQUENCE: 33

Gly Tyr Ala Asp Ser Val Lys Gly Arg Phe Thr Ile Ser Arg Asp Asn
1               5                   10                  15

Ala Lys Asn Ser Leu Tyr Leu Gln Met Asn Ser Leu Arg Ala Glu Asp
            20                  25                  30

Thr Ala Val Tyr Tyr Cys
        35

<210> SEQ ID NO 34
<211> LENGTH: 15
<212> TYPE: PRT
<213> ORGANISM: Artificial Sequence
<220> FEATURE:
<223> OTHER INFORMATION: Human anti-DLK1 antibody CDR

<400> SEQUENCE: 34

Thr Lys Gly Pro Gly Leu Ala Thr Gly Lys Val Tyr Phe Asn Ser
1               5                   10                  15

<210> SEQ ID NO 35
<211> LENGTH: 11
<212> TYPE: PRT
<213> ORGANISM: Artificial Sequence
<220> FEATURE:
<223> OTHER INFORMATION: Human anti-DLK1 antibody framework

<400> SEQUENCE: 35

Trp Gly Gln Gly Thr Gln Val Thr Val Ser Ser
1               5                   10

<210> SEQ ID NO 36
<211> LENGTH: 26
<212> TYPE: PRT
<213> ORGANISM: Artificial Sequence
<220> FEATURE:
<223> OTHER INFORMATION: Human anti-DLK1 antibody framework

<400> SEQUENCE: 36

Asp Ile Gln Met Thr Gln Ser Pro Ser Ser Val Ser Ala Ser Val Gly
1               5                   10                  15

Asp Arg Val Thr Ile Thr Cys Arg Ala Ser
            20                  25

<210> SEQ ID NO 37
<211> LENGTH: 6
<212> TYPE: PRT
<213> ORGANISM: Artificial Sequence
<220> FEATURE:
<223> OTHER INFORMATION: Human anti-DLK1 antibody CDR

<400> SEQUENCE: 37

Gln Arg Ile Ser Ser Trp
1               5

<210> SEQ ID NO 38
<211> LENGTH: 17
<212> TYPE: PRT
<213> ORGANISM: Artificial Sequence
<220> FEATURE:
<223> OTHER INFORMATION: Human anti-DLK1 antibody framework

<400> SEQUENCE: 38
```

Leu Ala Trp Tyr Gln Gln Lys Pro Gly Arg Ala Pro Lys Leu Leu Ile
1               5                   10                  15

His

<210> SEQ ID NO 39
<211> LENGTH: 3
<212> TYPE: PRT
<213> ORGANISM: Artificial Sequence
<220> FEATURE:
<223> OTHER INFORMATION: Human anti-DLK1 antibody CDR

<400> SEQUENCE: 39

Ser Ala Ser
1

<210> SEQ ID NO 40
<211> LENGTH: 36
<212> TYPE: PRT
<213> ORGANISM: Artificial Sequence
<220> FEATURE:
<223> OTHER INFORMATION: Human anti-DLK1 antibody framework

<400> SEQUENCE: 40

Thr Leu His Asn Gly Val Pro Ser Arg Phe Ser Gly Ser Ala Ser Gly
1               5                   10                  15

Thr Asp Phe Thr Leu Thr Ile Ser Ser Leu Gln Pro Glu Asp Phe Ala
            20                  25                  30

Ile Tyr Tyr Cys
        35

<210> SEQ ID NO 41
<211> LENGTH: 9
<212> TYPE: PRT
<213> ORGANISM: Artificial Sequence
<220> FEATURE:
<223> OTHER INFORMATION: Human anti-DLK1 antibody CDR

<400> SEQUENCE: 41

Gln Gln Gly His Ser Phe Pro Tyr Thr
1               5

<210> SEQ ID NO 42
<211> LENGTH: 10
<212> TYPE: PRT
<213> ORGANISM: Artificial Sequence
<220> FEATURE:
<223> OTHER INFORMATION: Human anti-DLK1 antibody framework

<400> SEQUENCE: 42

Phe Gly Gln Gly Thr Lys Leu Asp Ile Lys
1               5                   10

<210> SEQ ID NO 43
<211> LENGTH: 25
<212> TYPE: PRT
<213> ORGANISM: Artificial Sequence
<220> FEATURE:
<223> OTHER INFORMATION: Human anti-DLK1 antibody framework

<400> SEQUENCE: 43

Gln Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 44
<211> LENGTH: 8
<212> TYPE: PRT
<213> ORGANISM: Artificial Sequence
<220> FEATURE:
<223> OTHER INFORMATION: Human anti-DLK1 antibody CDR

<400> SEQUENCE: 44

Gly Phe Thr Phe Ser Ser Tyr Trp
1               5

<210> SEQ ID NO 45
<211> LENGTH: 17
<212> TYPE: PRT
<213> ORGANISM: Artificial Sequence
<220> FEATURE:
<223> OTHER INFORMATION: Human anti-DLK1 antibody framework

<400> SEQUENCE: 45

Met Asn Trp Val Arg Gln Ala Pro Gly Lys Gly Leu Val Trp Val Ser
1               5                   10                  15

Arg

<210> SEQ ID NO 46
<211> LENGTH: 8
<212> TYPE: PRT
<213> ORGANISM: Artificial Sequence
<220> FEATURE:
<223> OTHER INFORMATION: Human anti-DLK1 antibody CDR

<400> SEQUENCE: 46

Ile Ser Pro Asp Gly Ser Ser Thr
1               5

<210> SEQ ID NO 47
<211> LENGTH: 38
<212> TYPE: PRT
<213> ORGANISM: Artificial Sequence
<220> FEATURE:
<223> OTHER INFORMATION: Human anti-DLK1 antibody framework

<400> SEQUENCE: 47

Thr Tyr Ala Asp Ser Val Lys Gly Arg Phe Thr Ile Ser Arg Asp Asn
1               5                   10                  15

Ala Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 48
<211> LENGTH: 15
<212> TYPE: PRT
<213> ORGANISM: Artificial Sequence
<220> FEATURE:
<223> OTHER INFORMATION: Human anti-DLK1 antibody CDR

<400> SEQUENCE: 48

Ala Arg Gly Tyr Ser Pro Lys Tyr Pro Thr Val Gly Leu Asp Val
1               5                   10                  15

<210> SEQ ID NO 49
<211> LENGTH: 11
<212> TYPE: PRT
<213> ORGANISM: Artificial Sequence
<220> FEATURE:
<223> OTHER INFORMATION: Human anti-DLK1 antibody framework

<400> SEQUENCE: 49

Trp Gly Gln Gly Thr Thr Ile Thr Val Ser Ser
1               5                   10

<210> SEQ ID NO 50
<211> LENGTH: 26
<212> TYPE: PRT
<213> ORGANISM: Artificial Sequence
<220> FEATURE:
<223> OTHER INFORMATION: Human anti-DLK1 antibody framework

<400> SEQUENCE: 50

Asp Ile Val Met Thr Gln Ser Pro Leu Ser Ser Pro Val Thr Leu Gly
1               5                   10                  15

Gln Pro Ala Ser Ile Ser Cys Arg Ser Ser
            20                  25

<210> SEQ ID NO 51
<211> LENGTH: 11
<212> TYPE: PRT
<213> ORGANISM: Artificial Sequence
<220> FEATURE:
<223> OTHER INFORMATION: Human anti-DLK1 antibody CDR

<400> SEQUENCE: 51

Glu Ser Leu Leu His Ser Asn Gly Asn Thr Tyr
1               5                   10

<210> SEQ ID NO 52
<211> LENGTH: 17
<212> TYPE: PRT
<213> ORGANISM: Artificial Sequence
<220> FEATURE:
<223> OTHER INFORMATION: Human anti-DLK1 antibody framework

<400> SEQUENCE: 52

Leu Thr Trp Leu Gln Gln Arg Pro Gly Gln Pro Pro Arg Leu Leu Ile
1               5                   10                  15

His

<210> SEQ ID NO 53
<211> LENGTH: 3
<212> TYPE: PRT
<213> ORGANISM: Artificial Sequence
<220> FEATURE:
<223> OTHER INFORMATION: Human anti-DLK1 antibody CDR

<400> SEQUENCE: 53

Lys Ile Ser
1

<210> SEQ ID NO 54
<211> LENGTH: 36
<212> TYPE: PRT
<213> ORGANISM: Artificial Sequence
<220> FEATURE:
<223> OTHER INFORMATION: Human anti-DLK1 antibody framework

<400> SEQUENCE: 54

Asn Arg Phe Ser Gly Val Pro Asp Arg Phe Ser Gly Ser Gly Ala Gly
1               5                   10                  15

Thr Asp Phe Thr Leu Gln Ile Thr Arg Val Glu Thr Glu Asp Val Gly

```
                    20                  25                  30

Val Tyr Tyr Cys
        35

<210> SEQ ID NO 55
<211> LENGTH: 9
<212> TYPE: PRT
<213> ORGANISM: Artificial Sequence
<220> FEATURE:
<223> OTHER INFORMATION: Human anti-DLK1 antibody CDR

<400> SEQUENCE: 55

Val Gln Thr Thr Gln Trp Pro Trp Thr
1               5

<210> SEQ ID NO 56
<211> LENGTH: 10
<212> TYPE: PRT
<213> ORGANISM: Artificial Sequence
<220> FEATURE:
<223> OTHER INFORMATION: Human anti-DLK1 antibody framework

<400> SEQUENCE: 56

Phe Gly Gln Gly Thr Lys Val Glu Ile Lys
1               5                   10

<210> SEQ ID NO 57
<211> LENGTH: 25
<212> TYPE: PRT
<213> ORGANISM: Artificial Sequence
<220> FEATURE:
<223> OTHER INFORMATION: Human anti-DLK1 antibody framework

<400> SEQUENCE: 57

Gln Val Gln Leu Val Gln Ser Gly Ala Glu Val Lys Lys Pro Gly Ala
1               5                   10                  15

Ser Val Arg Val Ser Cys Lys Val Ser
            20                  25

<210> SEQ ID NO 58
<211> LENGTH: 8
<212> TYPE: PRT
<213> ORGANISM: Artificial Sequence
<220> FEATURE:
<223> OTHER INFORMATION: Human anti-DLK1 antibody CDR

<400> SEQUENCE: 58

Gly Tyr Ser Leu Ser Glu Phe Pro
1               5

<210> SEQ ID NO 59
<211> LENGTH: 17
<212> TYPE: PRT
<213> ORGANISM: Artificial Sequence
<220> FEATURE:
<223> OTHER INFORMATION: Human anti-DLK1 antibody framework

<400> SEQUENCE: 59

Ile His Trp Val Arg Gln Ala Pro Arg Met Gly Leu Glu Trp Met Gly
1               5                   10                  15

Gly

<210> SEQ ID NO 60
<211> LENGTH: 8
<212> TYPE: PRT
```

<213> ORGANISM: Artificial Sequence
<220> FEATURE:
<223> OTHER INFORMATION: Human anti-DLK1 antibody CDR

<400> SEQUENCE: 60

Ser Tyr Pro Glu Asp Gly Glu Thr
1               5

<210> SEQ ID NO 61
<211> LENGTH: 38
<212> TYPE: PRT
<213> ORGANISM: Artificial Sequence
<220> FEATURE:
<223> OTHER INFORMATION: Human anti-DLK1 antibody framework

<400> SEQUENCE: 61

Leu Tyr Ala Gln Lys Phe Gln Gly Arg Val Thr Met Thr Glu Asp Thr
1               5                   10                  15

Ser Thr Asp Thr Ala Tyr Met Glu Leu Ser Ser Leu Arg Ser Glu Asp
                20                  25                  30

Thr Ala Val Tyr Tyr Cys
                35

<210> SEQ ID NO 62
<211> LENGTH: 18
<212> TYPE: PRT
<213> ORGANISM: Artificial Sequence
<220> FEATURE:
<223> OTHER INFORMATION: Human anti-DLK1 antibody CDR

<400> SEQUENCE: 62

Ala Arg Leu Asn Tyr Phe Glu Ser Thr Asp Tyr Trp Val Asp Ala Phe
1               5                   10                  15

Asp Ile

<210> SEQ ID NO 63
<211> LENGTH: 11
<212> TYPE: PRT
<213> ORGANISM: Artificial Sequence
<220> FEATURE:
<223> OTHER INFORMATION: Human anti-DLK1 antibody framework

<400> SEQUENCE: 63

Trp Gly Gln Gly Thr Met Val Thr Val Ser Ser
1               5                   10

<210> SEQ ID NO 64
<211> LENGTH: 25
<212> TYPE: PRT
<213> ORGANISM: Artificial Sequence
<220> FEATURE:
<223> OTHER INFORMATION: Human anti-DLK1 antibody framework

<400> SEQUENCE: 64

Gln Leu Val Leu Thr Gln Pro Tyr Ser Val Ser Glu Ser Pro Gly Lys
1               5                   10                  15

Thr Ile Thr Ile Ser Cys Thr Arg Ser
                20                  25

<210> SEQ ID NO 65
<211> LENGTH: 8
<212> TYPE: PRT
<213> ORGANISM: Artificial Sequence
<220> FEATURE:
<223> OTHER INFORMATION: Human anti-DLK1 antibody CDR

<400> SEQUENCE: 65

Ser Gly Ser Ile Ala Ser Asn Phe
1               5

<210> SEQ ID NO 66
<211> LENGTH: 17
<212> TYPE: PRT
<213> ORGANISM: Artificial Sequence
<220> FEATURE:
<223> OTHER INFORMATION: Human anti-DLK1 antibody framework

<400> SEQUENCE: 66

Val Gln Trp Tyr Gln Gln Arg Pro Gly Ser Ala Pro Thr Pro Val Ile
1               5                   10                  15

Tyr

<210> SEQ ID NO 67
<211> LENGTH: 3
<212> TYPE: PRT
<213> ORGANISM: Artificial Sequence
<220> FEATURE:
<223> OTHER INFORMATION: Human anti-DLK1 antibody CDR

<400> SEQUENCE: 67

Glu Asp Asn
1

<210> SEQ ID NO 68
<211> LENGTH: 38
<212> TYPE: PRT
<213> ORGANISM: Artificial Sequence
<220> FEATURE:
<223> OTHER INFORMATION: Human anti-DLK1 antibody framework

<400> SEQUENCE: 68

Gln Arg Pro Ser Gly Val Pro Asp Arg Phe Ser Gly Ser Ile Asp Ser
1               5                   10                  15

Ser Ser Asn Ser Ala Ser Leu Thr Ile Ser Gly Val Met Thr Glu Asp
                20                  25                  30

Glu Ala Asp Tyr Tyr Cys
                35

<210> SEQ ID NO 69
<211> LENGTH: 10
<212> TYPE: PRT
<213> ORGANISM: Artificial Sequence
<220> FEATURE:
<223> OTHER INFORMATION: Human anti-DLK1 antibody CDR

<400> SEQUENCE: 69

Gln Ser Tyr Asp Ser Gly Ser Ser Trp Val
1               5                   10

<210> SEQ ID NO 70
<211> LENGTH: 10
<212> TYPE: PRT
<213> ORGANISM: Artificial Sequence
<220> FEATURE:
<223> OTHER INFORMATION: Human anti-DLK1 antibody framework

<400> SEQUENCE: 70

Phe Gly Gly Gly Thr Lys Leu Thr Val Leu
1               5                   10

<210> SEQ ID NO 71
<211> LENGTH: 25
<212> TYPE: PRT
<213> ORGANISM: Artificial Sequence
<220> FEATURE:
<223> OTHER INFORMATION: Human anti-DLK1 antibody framework

<400> SEQUENCE: 71

Gln Met Gln Leu Val Glu Ser Gly Gly Gly Leu Val Lys Pro Gly Gly
1               5                   10                  15

Ser Leu Thr Leu Ser Cys Asp Ala Thr
            20                  25

<210> SEQ ID NO 72
<211> LENGTH: 8
<212> TYPE: PRT
<213> ORGANISM: Artificial Sequence
<220> FEATURE:
<223> OTHER INFORMATION: Human anti-DLK1 antibody CDR

<400> SEQUENCE: 72

Gly Phe Asn Phe Gly Ser Tyr Tyr
1               5

<210> SEQ ID NO 73
<211> LENGTH: 17
<212> TYPE: PRT
<213> ORGANISM: Artificial Sequence
<220> FEATURE:
<223> OTHER INFORMATION: Human anti-DLK1 antibody framework

<400> SEQUENCE: 73

Met Asn Trp Val Arg Gln Ala Pro Gly Lys Gly Leu Glu Trp Leu Ala
1               5                   10                  15

His

<210> SEQ ID NO 74
<211> LENGTH: 8
<212> TYPE: PRT
<213> ORGANISM: Artificial Sequence
<220> FEATURE:
<223> OTHER INFORMATION: Human anti-DLK1 antibody CDR

<400> SEQUENCE: 74

Ile Ser Ser Thr Gly Arg Thr Ile
1               5

<210> SEQ ID NO 75
<211> LENGTH: 38
<212> TYPE: PRT
<213> ORGANISM: Artificial Sequence
<220> FEATURE:
<223> OTHER INFORMATION: Human anti-DLK1 antibody framework

<400> SEQUENCE: 75

Tyr Tyr Ala Asp Ser Val Lys Gly Arg Phe Thr Ile Ser Arg Asp Asn
1               5                   10                  15

Ala Lys Ser Ser Leu Asp Leu Gln Met Asn Ser Leu Arg Ala Glu Asp
            20                  25                  30

Thr Ala Val Tyr Tyr Cys
                35

<210> SEQ ID NO 76
<211> LENGTH: 12

```
<212> TYPE: PRT
<213> ORGANISM: Artificial Sequence
<220> FEATURE:
<223> OTHER INFORMATION: Human anti-DLK1 antibody CDR

<400> SEQUENCE: 76

Ala Arg Asp Gln Gly Tyr Pro Phe Gly Met Asp Val
1               5                   10

<210> SEQ ID NO 77
<211> LENGTH: 11
<212> TYPE: PRT
<213> ORGANISM: Artificial Sequence
<220> FEATURE:
<223> OTHER INFORMATION: Human anti-DLK1 antibody framework

<400> SEQUENCE: 77

Trp Gly His Gly Thr Thr Val Thr Val Ser Ser
1               5                   10

<210> SEQ ID NO 78
<211> LENGTH: 25
<212> TYPE: PRT
<213> ORGANISM: Artificial Sequence
<220> FEATURE:
<223> OTHER INFORMATION: Human anti-DLK1 antibody framework

<400> SEQUENCE: 78

Gln Leu Val Leu Thr Gln Pro Ser Ser Val Ser Gly Ala Pro Gly Gln
1               5                   10                  15

Arg Val Thr Ile Ser Cys Thr Gly Ser
            20                  25

<210> SEQ ID NO 79
<211> LENGTH: 9
<212> TYPE: PRT
<213> ORGANISM: Artificial Sequence
<220> FEATURE:
<223> OTHER INFORMATION: Human anti-DLK1 antibody CDR

<400> SEQUENCE: 79

Ser Ser Asn Ile Gly Ala Gly Tyr Asp
1               5

<210> SEQ ID NO 80
<211> LENGTH: 17
<212> TYPE: PRT
<213> ORGANISM: Artificial Sequence
<220> FEATURE:
<223> OTHER INFORMATION: Human anti-DLK1 antibody framework

<400> SEQUENCE: 80

Val Asp Trp Tyr Gln Gln Leu Pro Gly Thr Ala Pro Lys Leu Leu Ile
1               5                   10                  15

Tyr

<210> SEQ ID NO 81
<211> LENGTH: 3
<212> TYPE: PRT
<213> ORGANISM: Artificial Sequence
<220> FEATURE:
<223> OTHER INFORMATION: Human anti-DLK1 antibody CDR

<400> SEQUENCE: 81

Gly Asn Thr
1
```

```
<210> SEQ ID NO 82
<211> LENGTH: 36
<212> TYPE: PRT
<213> ORGANISM: Artificial Sequence
<220> FEATURE:
<223> OTHER INFORMATION: Human anti-DLK1 antibody framework

<400> SEQUENCE: 82

Asn Arg Pro Ser Gly Val Pro Asp Arg Phe Ser Gly Ser Lys Ser Gly
1               5                   10                  15

Thr Ser Ala Ser Leu Ala Ile Thr Gly Leu Gln Ala Glu Asp Asp Ser
            20                  25                  30

Asp Tyr Tyr Cys
        35

<210> SEQ ID NO 83
<211> LENGTH: 11
<212> TYPE: PRT
<213> ORGANISM: Artificial Sequence
<220> FEATURE:
<223> OTHER INFORMATION: Human anti-DLK1 antibody CDR

<400> SEQUENCE: 83

Gln Ser Tyr Asp Ser Ser Leu Ser Ala Trp Val
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Human anti-DLK1 antibody framework

<400> SEQUENCE: 84

Phe Gly Gly Gly Thr Lys Leu Thr Val Leu
1               5                   10

<210> SEQ ID NO 85
<211> LENGTH: 25
<212> TYPE: PRT
<213> ORGANISM: Artificial Sequence
<220> FEATURE:
<223> OTHER INFORMATION: Human anti-DLK1 antibody framework

<400> SEQUENCE: 85

Gln Val Gln Leu Val Glu Ser Gly Gly Gly Val Val Gln Pro Gly Arg
1               5                   10                  15

Ser Leu Arg Leu Ser Cys Ala Ala Ser
            20                  25

<210> SEQ ID NO 86
<211> LENGTH: 8
<212> TYPE: PRT
<213> ORGANISM: Artificial Sequence
<220> FEATURE:
<223> OTHER INFORMATION: Human anti-DLK1 antibody CDR

<400> SEQUENCE: 86

Gly Phe Thr Phe Ser Ser Tyr Ala
1               5

<210> SEQ ID NO 87
<211> LENGTH: 17
<212> TYPE: PRT
```

<213> ORGANISM: Artificial Sequence
<220> FEATURE:
<223> OTHER INFORMATION: Human anti-DLK1 antibody framework

<400> SEQUENCE: 87

Met His Trp Val Arg Gln Ala Pro Gly Lys Gly Leu Glu Trp Val Ala
1               5                   10                  15

Val

<210> SEQ ID NO 88
<211> LENGTH: 7
<212> TYPE: PRT
<213> ORGANISM: Artificial Sequence
<220> FEATURE:
<223> OTHER INFORMATION: Human anti-DLK1 antibody CDR

<400> SEQUENCE: 88

Ile Tyr Ser Gly Gly Ser Thr
1               5

<210> SEQ ID NO 89
<211> LENGTH: 38
<212> TYPE: PRT
<213> ORGANISM: Artificial Sequence
<220> FEATURE:
<223> OTHER INFORMATION: Human anti-DLK1 antibody framework

<400> SEQUENCE: 89

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 90
<211> LENGTH: 20
<212> TYPE: PRT
<213> ORGANISM: Artificial Sequence
<220> FEATURE:
<223> OTHER INFORMATION: Human anti-DLK1 antibody CDR

<400> SEQUENCE: 90

Ala Arg Glu Gly Ser Tyr Asp Val Met Thr Tyr Thr Arg Ile Gly Gly
1               5                   10                  15

Tyr Phe Asp Tyr
            20

<210> SEQ ID NO 91
<211> LENGTH: 11
<212> TYPE: PRT
<213> ORGANISM: Artificial Sequence
<220> FEATURE:
<223> OTHER INFORMATION: Human anti-DLK1 antibody framework

<400> SEQUENCE: 91

Trp Gly Gln Gly Ala Leu Val Thr Val Ser Ser
1               5                   10

<210> SEQ ID NO 92
<211> LENGTH: 26
<212> TYPE: PRT
<213> ORGANISM: Artificial Sequence
<220> FEATURE:
<223> OTHER INFORMATION: Human anti-DLK1 antibody framework

<400> SEQUENCE: 92

Asp Ile Gln Met Thr Gln Ser Pro Ser Ser Val Ser Ala Ser Val Gly
1               5                   10                  15

Asp Arg Val Thr Ile Thr Cys Arg Ala Ser
            20                  25

<210> SEQ ID NO 93
<211> LENGTH: 6
<212> TYPE: PRT
<213> ORGANISM: Artificial Sequence
<220> FEATURE:
<223> OTHER INFORMATION: Human anti-DLK1 antibody CDR

<400> SEQUENCE: 93

Gln Gly Ile Ser Asp Trp
1               5

<210> SEQ ID NO 94
<211> LENGTH: 17
<212> TYPE: PRT
<213> ORGANISM: Artificial Sequence
<220> FEATURE:
<223> OTHER INFORMATION: Human anti-DLK1 antibody framework

<400> SEQUENCE: 94

Val Ala Trp Tyr Gln Gln Lys Pro Gly Lys Ala Pro Lys Leu Leu Ile
1               5                   10                  15

Tyr

<210> SEQ ID NO 95
<211> LENGTH: 3
<212> TYPE: PRT
<213> ORGANISM: Artificial Sequence
<220> FEATURE:
<223> OTHER INFORMATION: Human anti-DLK1 antibody CDR

<400> SEQUENCE: 95

Ala Ala Ser
1

<210> SEQ ID NO 96
<211> LENGTH: 36
<212> TYPE: PRT
<213> ORGANISM: Artificial Sequence
<220> FEATURE:
<223> OTHER INFORMATION: Human anti-DLK1 antibody framework

<400> SEQUENCE: 96

Ser Leu Gln Ser Gly Val Pro Ser Arg Phe Ser Gly Ser Gly Ser Gly
1               5                   10                  15

Thr Glu Phe Ser Leu Thr Ile Ser Asn Leu Gln Pro Glu Asp Phe Ala
            20                  25                  30

Thr Tyr Tyr Cys
        35

<210> SEQ ID NO 97
<211> LENGTH: 9
<212> TYPE: PRT
<213> ORGANISM: Artificial Sequence
<220> FEATURE:
<223> OTHER INFORMATION: Human anti-DLK1 antibody CDR

<400> SEQUENCE: 97

Gln Gln Ala Asn Ser Phe Pro Leu Thr
1               5

<210> SEQ ID NO 98
<211> LENGTH: 10
<212> TYPE: PRT
<213> ORGANISM: Artificial Sequence
<220> FEATURE:
<223> OTHER INFORMATION: Human anti-DLK1 antibody framework

<400> SEQUENCE: 98

Phe Gly Pro Gly Thr Lys Val Glu Ile Lys
1               5                   10

<210> SEQ ID NO 99
<211> LENGTH: 120
<212> TYPE: PRT
<213> ORGANISM: Artificial Sequence
<220> FEATURE:
<223> OTHER INFORMATION: DLK1 VH Sequence

<400> SEQUENCE: 99

Gln Val Gln Leu Val Glu Ser Gly Gly Thr Leu Val Gln Pro Gly Gly
1               5                   10                  15

Ser Leu Arg Leu Ser Cys Ala Ala Ser Gly Phe Thr Phe Ser Ser His
            20                  25                  30

Ala Met Ser Trp Val Arg Gln Thr Pro Gly Lys Gly Leu Glu Trp Val
        35                  40                  45

Ser Ser Ile Thr Lys Ser Gly Ser Gly Thr Tyr Ser Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Glu Gly Leu Gly Tyr Tyr Tyr Gly Met Asp Val Trp Gly Gln
            100                 105                 110

Gly Thr Thr Val Thr Val Ser Ser
        115                 120

<210> SEQ ID NO 100
<211> LENGTH: 112
<212> TYPE: PRT
<213> ORGANISM: Artificial Sequence
<220> FEATURE:
<223> OTHER INFORMATION: DLK1 VL Sequence

<400> SEQUENCE: 100

Gln Leu Val Leu Thr Gln Pro Pro Ser Val Ser Gly Ala Pro Gly Gln
1               5                   10                  15

Arg Val Ile Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Arg Leu
        35                  40                  45

Leu Ile Tyr Gly Ser Thr Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Asn Ser
                85                  90                  95

Leu Ser Ala His Tyr Val Phe Gly Thr Gly Thr Lys Val Thr Val Leu

<210> SEQ ID NO 101
<211> LENGTH: 117
<212> TYPE: PRT
<213> ORGANISM: Artificial Sequence
<220> FEATURE:
<223> OTHER INFORMATION: DLK1 VH Sequence

<400> SEQUENCE: 101

```
Gln Val Gln Leu Val Gln Ser Gly Gly Ala Val Val Gln Pro Gly His
1               5                   10                  15
Ser Leu Arg Leu Ser Cys Glu Ala Ser Gly Phe Lys Phe Lys Asp Tyr
            20                  25                  30
Gly Met His Trp Val Arg Gln Ala Pro Gly Lys Gly Leu Glu Trp Leu
        35                  40                  45
Ala Val Ile Ser His Asp Gly Arg Asn Lys Asn Tyr Ala Asp Ser Val
    50                  55                  60
Lys Gly Arg Leu Thr Ile Ser Arg Asp Asn Ser Lys Asn Thr Leu Ser
65                  70                  75                  80
Phe Gln Met Asn Ser Leu Arg Ala Glu Asp Thr Ala Val Tyr Tyr Cys
                85                  90                  95
Val Arg Asp Trp Ser Tyr Ala Phe Asp Ile Trp Gly Gln Gly Thr Leu
            100                 105                 110
Val Thr Val Ser Ser
        115
```

<210> SEQ ID NO 102
<211> LENGTH: 107
<212> TYPE: PRT
<213> ORGANISM: Artificial Sequence
<220> FEATURE:
<223> OTHER INFORMATION: DLK1 VL Sequence

<400> SEQUENCE: 102

```
Asp Ile Gln Met Thr Gln Ser Pro Ser Phe Leu Ser Ala Ser Val Gly
1               5                   10                  15
Asp Arg Val Asn Ile Thr Cys Arg Ala Ser Gln Asp Ile Ser Arg Arg
            20                  25                  30
Leu Ala Trp Tyr Gln Gln Lys Pro Gly Lys Ala Pro Lys Leu Leu Ile
        35                  40                  45
Tyr Gly Ala Ala Ser Leu Gln Ser Ala Val Ala Ser Arg Phe Ser Gly
    50                  55                  60
Ser Gly Ser Gly Thr Glu Phe Thr Leu Thr Ile Ser Ser Leu Gln Pro
65                  70                  75                  80
Glu Asp Phe Ala Asn Tyr Tyr Cys Gln Gln Ile Tyr Thr Thr Pro Leu
                85                  90                  95
Thr Phe Gly Gly Gly Thr Lys Val Glu Ile Lys
            100                 105
```

<210> SEQ ID NO 103
<211> LENGTH: 122
<212> TYPE: PRT
<213> ORGANISM: Artificial Sequence
<220> FEATURE:
<223> OTHER INFORMATION: DLK1 VH Sequence

<400> SEQUENCE: 103

```
Gln Met Gln Leu Val Gln Ser Gly Gly Gly Leu Val Gln Pro Gly Arg
1               5                   10                  15
```

```
Ser Leu Arg Leu Ser Cys Ala Ala Ser Gly Phe Thr Phe Asp Asp Tyr
        20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Lys Gly Pro Gly Leu Ala Thr Gly Lys Val Tyr Phe Asn Ser Trp
            100                 105                 110

Gly Gln Gly Thr Gln Val Thr Val Ser Ser
            115                 120
```

<210> SEQ ID NO 104
<211> LENGTH: 107
<212> TYPE: PRT
<213> ORGANISM: Artificial Sequence
<220> FEATURE:
<223> OTHER INFORMATION: DLK1 VL Sequence

<400> SEQUENCE: 104

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Arg Ile Ser Ser Trp
            20                  25                  30

Leu Ala Trp Tyr Gln Gln Lys Pro Gly Arg Ala Pro Lys Leu Leu Ile
        35                  40                  45

His Ser Ala Ser Thr Leu His Asn Gly Val Pro Ser Arg Phe Ser Gly
50                  55                  60

Ser Ala Ser Gly Thr Asp Phe Thr Leu Thr Ile Ser Ser Leu Gln Pro
65                  70                  75                  80

Glu Asp Phe Ala Ile Tyr Tyr Cys Gln Gln Gly His Ser Phe Pro Tyr
                85                  90                  95

Thr Phe Gly Gln Gly Thr Lys Leu Asp Ile Lys
            100                 105
```

<210> SEQ ID NO 105
<211> LENGTH: 122
<212> TYPE: PRT
<213> ORGANISM: Artificial Sequence
<220> FEATURE:
<223> OTHER INFORMATION: DLK1 VH Sequence

<400> SEQUENCE: 105

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Asn Trp Val Arg Gln Ala Pro Gly Lys Gly Leu Val Trp Val
        35                  40                  45

Ser Arg Ile Ser Pro Asp Gly Ser Thr Thr Tyr Ala Asp Ser Val
50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
```

```
                    85                  90                  95
Ala Arg Gly Tyr Ser Pro Lys Tyr Pro Thr Val Gly Leu Asp Val Trp
                100                 105                 110

Gly Gln Gly Thr Thr Ile Thr Val Ser Ser
        115                 120

<210> SEQ ID NO 106
<211> LENGTH: 112
<212> TYPE: PRT
<213> ORGANISM: Artificial Sequence
<220> FEATURE:
<223> OTHER INFORMATION: DLK1 VL Sequence

<400> SEQUENCE: 106

Asp Ile Val Met Thr Gln Ser Pro Leu Ser Ser Pro Val Thr Leu Gly
1               5                   10                  15

Gln Pro Ala Ser Ile Ser Cys Arg Ser Ser Glu Ser Leu Leu His Ser
            20                  25                  30

Asn Gly Asn Thr Tyr Leu Thr Trp Leu Gln Gln Arg Pro Gly Gln Pro
        35                  40                  45

Pro Arg Leu Leu Ile His Lys Ile Ser Asn Arg Phe Ser Gly Val Pro
    50                  55                  60

Asp Arg Phe Ser Gly Ser Gly Ala Gly Thr Asp Phe Thr Leu Gln Ile
65                  70                  75                  80

Thr Arg Val Glu Thr Glu Asp Val Gly Val Tyr Tyr Cys Val Gln Thr
                85                  90                  95

Thr Gln Trp Pro Trp Thr Phe Gly Gln Gly Thr Lys Val Glu Ile Lys
                100                 105                 110

<210> SEQ ID NO 107
<211> LENGTH: 125
<212> TYPE: PRT
<213> ORGANISM: Artificial Sequence
<220> FEATURE:
<223> OTHER INFORMATION: DLK1 VH Sequence

<400> SEQUENCE: 107

Gln Val Gln Leu Val Gln Ser Gly Ala Glu Val Lys Lys Pro Gly Ala
1               5                   10                  15

Ser Val Arg Val Ser Cys Lys Val Ser Gly Tyr Ser Leu Ser Glu Phe
            20                  25                  30

Pro Ile His Trp Val Arg Gln Ala Pro Arg Met Gly Leu Glu Trp Met
        35                  40                  45

Gly Gly Ser Tyr Pro Glu Asp Gly Glu Thr Leu Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Asn Tyr Phe Glu Ser Thr Asp Tyr Trp Val Asp Ala Phe
                100                 105                 110

Asp Ile Trp Gly Gln Gly Thr Met Val Thr Val Ser Ser
        115                 120                 125

<210> SEQ ID NO 108
<211> LENGTH: 111
<212> TYPE: PRT
<213> ORGANISM: Artificial Sequence
<220> FEATURE:
```

<223> OTHER INFORMATION: DLK1 VL Sequence

<400> SEQUENCE: 108

```
Gln Leu Val Leu Thr Gln Pro Tyr Ser Val Ser Glu Ser Pro Gly Lys
1               5                   10                  15

Thr Ile Thr Ile Ser Cys Thr Arg Ser Ser Gly Ser Ile Ala Ser Asn
            20                  25                  30

Phe Val Gln Trp Tyr Gln Gln Arg Pro Gly Ser Ala Pro Thr Pro Val
        35                  40                  45

Ile Tyr Glu Asp Asn Gln Arg Pro Ser Gly Val Pro Asp Arg Phe Ser
50                  55                  60

Gly Ser Ile Asp Ser Ser Ser Asn Ser Ala Leu Thr Ile Ser Gly
65                  70                  75                  80

Val Met Thr Glu Asp Glu Ala Asp Tyr Tyr Cys Gln Ser Tyr Asp Ser
                85                  90                  95

Ser Ser Ser Trp Val Phe Gly Gly Gly Thr Lys Leu Thr Val Leu
            100                 105                 110
```

<210> SEQ ID NO 109
<211> LENGTH: 119
<212> TYPE: PRT
<213> ORGANISM: Artificial Sequence
<220> FEATURE:
<223> OTHER INFORMATION: DLK1 VH Sequence

<400> SEQUENCE: 109

```
Gln Met Gln Leu Val Glu Ser Gly Gly Gly Leu Val Lys Pro Gly Gly
1               5                   10                  15

Ser Leu Thr Leu Ser Cys Asp Ala Thr Gly Phe Asn Phe Gly Ser Tyr
            20                  25                  30

Tyr Met Asn Trp Val Arg Gln Ala Pro Gly Lys Gly Leu Glu Trp Leu
        35                  40                  45

Ala His Ile Ser Ser Thr Gly Arg Thr Ile Tyr Tyr Ala Asp Ser Val
50                  55                  60

Lys Gly Arg Phe Thr Ile Ser Arg Asp Asn Ala Lys Ser Ser Leu Asp
65                  70                  75                  80

Leu Gln Met Asn Ser Leu Arg Ala Glu Asp Thr Ala Val Tyr Tyr Cys
                85                  90                  95

Ala Arg Asp Gln Gly Tyr Pro Phe Gly Met Asp Val Trp Gly His Gly
            100                 105                 110

Thr Thr Val Thr Val Ser Ser
        115
```

<210> SEQ ID NO 110
<211> LENGTH: 111
<212> TYPE: PRT
<213> ORGANISM: Artificial Sequence
<220> FEATURE:
<223> OTHER INFORMATION: DLK1 VL Sequence

<400> SEQUENCE: 110

```
Gln Leu Val Leu Thr Gln Pro Ser Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val Asp Trp Tyr Gln Gln Leu Pro Gly Thr Ala Pro Lys Leu
        35                  40                  45

Leu Ile Tyr Gly Asn Thr Asn Arg Pro Ser Gly Val Pro Asp Arg Phe
```

```
                    50                  55                  60
Ser Gly Ser Lys Ser Gly Thr Ser Ala Ser Leu Ala Ile Thr Gly Leu
 65                  70                  75                  80

Gln Ala Glu Asp Asp Ser Asp Tyr Tyr Cys Gln Ser Tyr Asp Ser Ser
                 85                  90                  95

Leu Ser Ala Trp Val Phe Gly Gly Gly Thr Lys Leu Thr Val Leu
            100                 105                 110
```

<210> SEQ ID NO 111
<211> LENGTH: 126
<212> TYPE: PRT
<213> ORGANISM: Artificial Sequence
<220> FEATURE:
<223> OTHER INFORMATION: DLK1 VH Sequence

<400> SEQUENCE: 111

```
Gln Val Gln Leu Val Glu Ser Gly Gly Gly Val Val Gln Pro Gly Arg
 1                5                  10                  15

Ser Leu Arg Leu Ser Cys Ala Ala Ser Gly Phe Thr Phe Ser Ser Tyr
                 20                  25                  30

Ala Met His Trp Val Arg Gln Ala Pro Gly Lys Gly Leu Glu Trp Val
             35                  40                  45

Ala Val Ile Tyr Ser Gly Gly Ser Thr Tyr Tyr Ala Asp Ser Val Lys
         50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Glu Gly Ser Tyr Asp Val Met Thr Tyr Thr Arg Ile Gly Gly Tyr
            100                 105                 110

Phe Asp Tyr Trp Gly Gln Gly Ala Leu Val Thr Val Ser Ser
            115                 120                 125
```

<210> SEQ ID NO 112
<211> LENGTH: 107
<212> TYPE: PRT
<213> ORGANISM: Artificial Sequence
<220> FEATURE:
<223> OTHER INFORMATION: DLK1 VL Sequence

<400> SEQUENCE: 112

```
Asp Ile Gln Met Thr Gln Ser Pro Ser Ser Val Ser Ala Ser Val Gly
 1                5                  10                  15

Asp Arg Val Thr Ile Thr Cys Arg Ala Ser Gln Gly Ile Ser Asp Trp
                 20                  25                  30

Val Ala Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
         50                  55                  60

Ser Gly Ser Gly Thr Glu Phe Ser Leu Thr Ile Ser Asn Leu Gln Pro
 65                  70                  75                  80

Glu Asp Phe Ala Thr Tyr Tyr Cys Gln Gln Ala Asn Ser Phe Pro Leu
                 85                  90                  95

Thr Phe Gly Pro Gly Thr Lys Val Glu Ile Lys
            100                 105
```

<210> SEQ ID NO 113
<211> LENGTH: 38

```
<212> TYPE: DNA
<213> ORGANISM: Artificial Sequence
<220> FEATURE:
<223> OTHER INFORMATION: synthetic oligonucleotide

<400> SEQUENCE: 113 aggggggccgt gggggccgct gaatgcttcc cggcctgc                              38

<210> SEQ ID NO 114
<211> LENGTH: 40
<212> TYPE: DNA
<213> ORGANISM: Artificial Sequence
<220> FEATURE:
<223> OTHER INFORMATION: synthetic oligonucleotide

<400> SEQUENCE: 114
tagcggccga cgcggccaac tggccctcgg tgaggagagg                             40

<210> SEQ ID NO 115
<211> LENGTH: 6
<212> TYPE: PRT
<213> ORGANISM: Artificial Sequence
<220> FEATURE:
<223> OTHER INFORMATION: Human anti-DLK1 antibody CDR

<400> SEQUENCE: 115

Gln Gly Ile Ser Ser Ala
1               5

<210> SEQ ID NO 116
<211> LENGTH: 9
<212> TYPE: PRT
<213> ORGANISM: Artificial Sequence
<220> FEATURE:
<223> OTHER INFORMATION: Human anti-DLK1 antibody CDR

<400> SEQUENCE: 116

Gln Gln Ser Tyr Thr Thr Pro Leu Thr
1               5

<210> SEQ ID NO 117
<211> LENGTH: 26
<212> TYPE: PRT
<213> ORGANISM: Artificial Sequence
<220> FEATURE:
<223> OTHER INFORMATION: Human anti-DLK1 antibody framework

<400> SEQUENCE: 117

Asp Ile Gln Met Thr Gln Ser Pro Ser Ser Leu Ser Ala Ser Leu Gly
1               5                   10                  15
Asp Arg Val Thr Ile Thr Cys Arg Ala Ser
            20                  25

<210> SEQ ID NO 118
<211> LENGTH: 36
<212> TYPE: PRT
<213> ORGANISM: Artificial Sequence
<220> FEATURE:
<223> OTHER INFORMATION: Human anti-DLK1 antibody framework

<400> SEQUENCE: 118

Ser Leu Gln Ser Gly Val Pro Ser Arg Phe Ser Gly Ser Gly Ser Gly
1               5                   10                  15
Thr Asp Phe Thr Leu Thr Ile Asn Ser Leu Gln Pro Glu Asp Phe Ala
            20                  25                  30
```

```
Thr Tyr Tyr Cys
        35

<210> SEQ ID NO 119
<211> LENGTH: 25
<212> TYPE: PRT
<213> ORGANISM: Artificial Sequence
<220> FEATURE:
<223> OTHER INFORMATION: Human anti-DLK1 antibody framework

<400> SEQUENCE: 119

Gln Val Gln Leu Val Gln Ser Gly Gly Gly Val Val Gln Pro Gly Gly
1               5                   10                  15

Ser Leu Arg Leu Ser Cys Ala Ala Ser
            20                  25

<210> SEQ ID NO 120
<211> LENGTH: 26
<212> TYPE: PRT
<213> ORGANISM: Artificial Sequence
<220> FEATURE:
<223> OTHER INFORMATION: Human anti-DLK1 antibody framework

<400> SEQUENCE: 120

Asp Ile Gln Met Thr Gln Ser Pro Ser Phe Leu Ser Ala Ser Val Gly
1               5                   10                  15

Asp Arg Val Thr Ile Thr Cys Arg Ala Ser
            20                  25

<210> SEQ ID NO 121
<211> LENGTH: 6
<212> TYPE: PRT
<213> ORGANISM: Artificial Sequence
<220> FEATURE:
<223> OTHER INFORMATION: Human anti-DLK1 antibody CDR

<400> SEQUENCE: 121

His Asp Ile Ser Ser Ser
1               5

<210> SEQ ID NO 122
<211> LENGTH: 17
<212> TYPE: PRT
<213> ORGANISM: Artificial Sequence
<220> FEATURE:
<223> OTHER INFORMATION: Human anti-DLK1 antibody framework

<400> SEQUENCE: 122

Leu Ala Trp Tyr Gln Gln Lys Ser Gly Lys Ala Pro Lys Leu Leu Ile
1               5                   10                  15

Tyr

<210> SEQ ID NO 123
<211> LENGTH: 36
<212> TYPE: PRT
<213> ORGANISM: Artificial Sequence
<220> FEATURE:
<223> OTHER INFORMATION: Human anti-DLK1 antibody framework

<400> SEQUENCE: 123

Asn Leu Lys Ser Gly Val Pro Ser Arg Phe Ser Gly Ser Gly Ser Gly
1               5                   10                  15

Thr Asp Phe Ser Leu Thr Ile Ser Ser Leu Gln Pro Glu Asp Phe Ala
            20                  25                  30
```

Thr Tyr Tyr Cys
         35

<210> SEQ ID NO 124
<211> LENGTH: 9
<212> TYPE: PRT
<213> ORGANISM: Artificial Sequence
<220> FEATURE:
<223> OTHER INFORMATION: Human anti-DLK1 antibody CDR

<400> SEQUENCE: 124

Gln Gln Ser Tyr Thr Thr Val Leu Thr
1               5

<210> SEQ ID NO 125
<211> LENGTH: 10
<212> TYPE: PRT
<213> ORGANISM: Artificial Sequence
<220> FEATURE:
<223> OTHER INFORMATION: Human anti-DLK1 antibody framework

<400> SEQUENCE: 125

Phe Gly Gly Gly Thr Lys Leu Glu Ile Lys
1               5                   10

<210> SEQ ID NO 126
<211> LENGTH: 107
<212> TYPE: PRT
<213> ORGANISM: Artificial Sequence
<220> FEATURE:
<223> OTHER INFORMATION: DLK1 VL Sequence

<400> SEQUENCE: 126

Asp Ile Gln Met Thr Gln Ser Pro Ser Ser Leu Ser Ala Ser Leu Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Ser Tyr Thr Thr Pro Leu
                85                  90                  95

Thr Phe Gly Gly Gly Thr Lys Val Glu Ile Lys
            100                 105

<210> SEQ ID NO 127
<211> LENGTH: 117
<212> TYPE: PRT
<213> ORGANISM: Artificial Sequence
<220> FEATURE:
<223> OTHER INFORMATION: DLK1 VH Sequence

<400> SEQUENCE: 127

Gln Val Gln Leu Val Gln Ser Gly Gly Val Val Gln Pro Gly Gly
1               5                   10                  15

Ser Leu Arg Leu Ser Cys Ala Ala Ser Gly Phe Lys Phe Lys Asp Tyr
            20                  25                  30

Gly Met His Trp Val Arg Gln Ala Pro Gly Lys Gly Leu Glu Trp Leu
        35                  40                  45

```
Ala Val Ile Ser His Asp Gly Arg Asn Lys Asn Tyr Ala Asp Ser Val
        50                  55                  60

Lys Gly Arg Leu Thr Ile Ser Arg Asp Asn Ser Lys Asn Thr Leu Ser
65                      70                  75                  80

Phe Gln Met Asn Ser Leu Arg Ala Glu Asp Thr Ala Val Tyr Tyr Cys
                85                  90                  95

Val Arg Asp Trp Ser Tyr Ala Phe Asp Ile Trp Gly Gln Gly Thr Leu
                100                 105                 110

Val Thr Val Ser Ser
            115

<210> SEQ ID NO 128
<211> LENGTH: 107
<212> TYPE: PRT
<213> ORGANISM: Artificial Sequence
<220> FEATURE:
<223> OTHER INFORMATION: DLK1 VL Sequence

<400> SEQUENCE: 128

Asp Ile Gln Met Thr Gln Ser Pro Ser Phe Leu Ser Ala Ser Val Gly
1               5                   10                  15

Asp Arg Val Thr Ile Thr Cys Arg Ala Ser His Asp Ile Ser Ser Ser
            20                  25                  30

Leu Ala Trp Tyr Gln Gln Lys Ser Gly Lys Ala Pro Lys Leu Leu Ile
            35                  40                  45

Tyr Ser Ala Ser Asn Leu Lys Ser Gly Val Pro Ser Arg Phe Ser Gly
        50                  55                  60

Ser Gly Ser Gly Thr Asp Phe Ser Leu Thr Ile Ser Ser Leu Gln Pro
65                  70                  75                  80

Glu Asp Phe Ala Thr Tyr Tyr Cys Gln Gln Ser Tyr Thr Thr Val Leu
                85                  90                  95

Thr Phe Gly Gly Gly Thr Lys Leu Glu Ile Lys
            100                 105
```

ANTIBODY AGAINST HUMAN DLK1 AND USE THEREOF

TECHNICAL FIELD

The present invention relates to an antibody against delta-like 1 homolog (*Drosophila*) (DLK1) or an antigen-binding fragment thereof, a nucleic acid encoding the same, a vector including the nucleic acid, a cell transformed with the vector, a method of producing the antibody or an antigen-binding fragment thereof, an antibody-drug conjugate (ADC) including the same, a pharmaceutical composition for treating cancer, a composition for diagnosing cancer, and a chimeric antigen receptor (CAR) and a T-cell engager including the same.

BACKGROUND ART

Human-derived delta-like 1 homolog (*Drosophila*) (DLK1) is a single-pass transmembrane protein including 383 amino acids in total and having six epidermal growth factor-like repeat domains in the extracellular domain. DLK1 is commonly referred to as a "DLK1" gene due to the homology of the amino acid sequence with Delta, the ligand of the Notch receptor which is a factor that regulates cell differentiation, and is also called "Pref-1", "pG2", "SCP-1" and "ZOG". DLK1 is a membrane protein, but is also well-known as a protein having separate functionality, which is generated through the shedding from the cell membrane of the extracellular domain thereof by a tumor necrosis factor alpha converting enzyme (TACE).

DLK1 is highly expressed in fetal cells, which are undifferentiated and thus proliferate readily. In particular, DLK1 is highly expressed in fetal liver, kidneys, skeletal muscle, brain and the like, but after birth, expression of DLK1 is not found in most tissues and DLK1 is expressed only in certain cells such as preadipocytes, pancreatic islet cells, thymic stromal cells and adrenal gland cells.

DLK1 is known as preadipocyte factor-1 (Pref-1), which is a factor of inhibiting the differentiation of adipocytes, and functional studies on DLK1 have been most actively conducted in this regard. In addition to the ability to inhibit differentiation of adipocytes, DLK1 is known to be involved in functions of inhibiting the differentiation of hematopoietic stem cells, of regulating the differentiation of lymphoid progenitor cells and of facilitating wound healing.

DLK1 has also been reported to be expressed at high frequency in a variety of kinds of cancers and tumors. Examples of cancer in which expression thereof has been found to date include, as solid cancer, neuroendocrine tumors, neuroblastomas, glioma, type 1 neurofibromatosis, small-cell lung cancer, liver cancer, kidney cancer, ovarian cancer, colorectal cancer, breast cancer and pancreatic cancer and, as blood cancer, myelodysplastic syndrome and acute myeloid leukemia. Studies have been conducted on the relationship between DLK1 and cancer. For example, it has been reported that DLK1 is overexpressed in brain cancer cells (glioma), and overexpression of cDNA of DLK1 in glioma enhances the proliferation of glioma, thus facilitating migration. It has been reported that the expression level of DLK1 in liver cancer is higher than that in normal hepatocytes and that the size of tumors decreased when the expression of DLK1 was reduced by siRNA experiments.

Meanwhile, although cancer is a serious disease that is one of the most common causes of death, demand for treatment therefor has not yet been satisfied. Recently, in order to solve the problem in which conventional chemotherapy also causes damage to normal cells, cancer treatment with molecularly targeted drugs, which are designed to target and treat specific molecules that are specifically expressed in cancer cells, has been actively researched.

The molecularly targeted drugs targeting specific antigens are already widely available as antibody drugs, and most examples thereof have antibody-dependent cellular cytotoxicity (ADCC) as a major mechanism of action. However, the efficacy of the drugs does not meet requirements, and the development of technologies aiming at more potent anticancer activity is also in progress.

One effective means of enhancing the anticancer activity of antibodies is the linking of antibodies with substances (toxins) having strong toxicity. Toxins, when administered alone to patients, also cause damage to normal tissues and cannot be an effective treatment means. However, by linking toxins with antibodies that bind to cancer-cell-specific antigens, it is possible to realize the ability to kill only cancer cells without adversely affecting normal tissues. Such drugs are called antibody-drug conjugates (ADCs). After ADCs binding to specific target receptors present on the surface of cancer cells are incorporated into cells through endocytosis, antibodies are degraded in the lysosomes and toxins are released out of the lysosomes, so that toxicity is expressed only inside certain cells and the cells are killed due to the effects thereof.

Only a limited number of antibodies for ADCs have been developed to date, a representative example of which is Herceptin (Genentech Inc.), which is an anti-Her2 antibody, and other examples include respective antibodies against CD33, CD30, CD22, CD138, PMSA, EphA2 and the like from other international multinational pharmaceutical companies, which are in the phase of clinical trials or the early stage of new drug development. In Korea, efforts to develop new antibodies for ADC have been insignificant to date.

Under this technical background, the present inventors have endeavored to develop an antibody that binds specifically to DLK1. As a result, the present inventors have completed the present invention by developing an anti-DLK1 antibody exhibiting excellent binding affinity to DLK1 and confirming that target cancers can be treated or diagnosed by using the same.

DISCLOSURE

Technical Problem

It is one object of the present invention to provide a novel antibody against a delta-like 1 homolog (DLK1) or an antigen-binding fragment thereof.

It is another object of the present invention to provide a nucleic acid encoding the antibody or an antigen-binding fragment thereof.

It is another object of the present invention to provide a vector including the nucleic acid, a cell transformed with the vector, and a method of producing the antibody or an antigen-binding fragment thereof.

It is another object of the present invention to provide an antibody-drug conjugate (ADC) including the antibody or an antigen-binding fragment thereof.

It is another object of the present invention to provide a pharmaceutical composition for preventing or treating cancer including the antibody or an antigen-binding fragment thereof.

It is another object of the present invention to provide a composition for diagnosing cancer including the antibody or an antigen-binding fragment thereof.

It is another object of the present invention to provide a chimeric antigen receptor (CAR) including the antibody or an antigen-binding fragment thereof.

It is another object of the present invention to provide a T-cell engager including the antibody or an antigen-binding fragment thereof.

Technical Solution

To achieve the above objects, in accordance with one aspect of the present invention, provided is an antibody or an antigen-binding fragment thereof that specifically binds to a human delta-like 1 homolog (*Drosophila*) (DLK1) including the following heavy and light-chain variable regions: a heavy-chain variable region including at least one heavy-chain CDR1 selected from the group consisting of SEQ ID. NOS: 2, 16, 30, 44, 58, 72 and 86, at least one heavy-chain CDR2 selected from the group consisting of SEQ ID. NOS: 4, 18, 32, 46, 60, 74 and 88, and at least one heavy-chain CDR3 selected from the group consisting of SEQ ID NOS: 6, 20, 34, 48, 62, 76 and 90; and a light-chain variable region including at least one light-chain CDR1 selected from the group consisting of SEQ ID NOS: 9, 23, 37, 51, 65, 79, 93, 115 and 121, at least one light-chain CDR2 selected from the group consisting of SEQ ID NOS: 11, 25, 39, 53, 67, 81 and 95, and at least one light-chain CDR3 selected from the group consisting of SEQ ID NOS: 13, 27, 41, 55, 69, 83, 97, 116 and 125.

In another aspect of the present invention, provided is a nucleic acid encoding the antibody or an antigen-binding fragment thereof.

In another aspect of the present invention, provided is a vector including the nucleic acid.

In another aspect of the present invention, provided is a cell transformed with the vector.

In another aspect of the present invention, provided is a method of producing the antibody or an antigen-binding fragment thereof including the following steps: (a) culturing cells; and (b) recovering an antibody or an antigen-binding fragment thereof from the cultured cells.

In another aspect of the present invention, provided is an antibody-drug conjugate (ADC) including the antibody or an antigen-binding fragment thereof, and a drug.

In another aspect of the present invention, provided is a bispecific antibody including the antibody or an antigen-binding fragment thereof.

In another aspect of the present invention, provided is a pharmaceutical composition for preventing or treating cancer including, as an active ingredient, the antibody or an antigen-binding fragment thereof, the antibody-drug conjugate or the bispecific antibody.

In another aspect of the present invention, provided is a composition for diagnosing cancer including the antibody or an antigen-binding fragment thereof.

In another aspect of the present invention, provided is a chimeric antigen receptor (CAR) including the antibody or an antigen-binding fragment thereof.

In another aspect of the present invention, provided is a T-cell engager including the antibody or an antigen-binding fragment thereof, specifically binding to human DLK1 expressed in tumor cells.

BEST MODE

Figure 1:
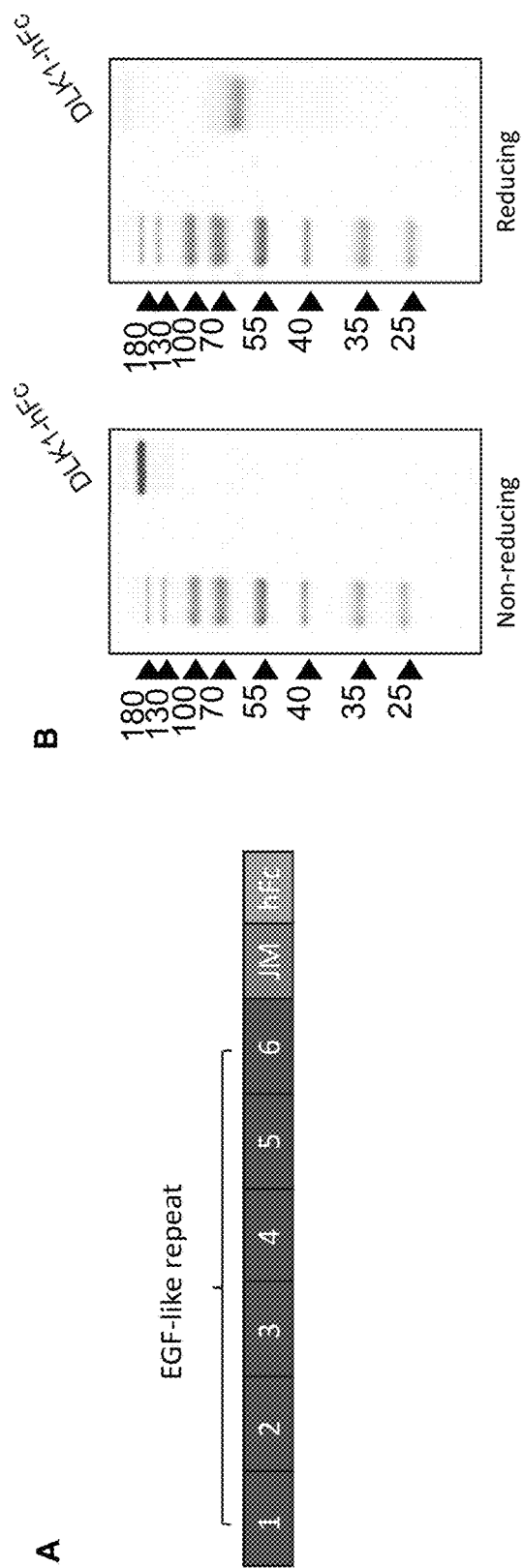
FIG. 1 shows a schematic diagram (A) showing a DLK1-hFc fusion protein, a conjugate between an extracellular region of a human DLK1 protein including six EGF-like repeat domains and a human antibody Fc (hFc) region, produced for use as an antigen in the present invention; and a purification result (B) of the DLK1-hFc fusion protein, wherein in A, 1 to 6 represent EGF-like repeat domains 1 to 6, respectively, and JM represents a juxtamembrane domain, and in B, "Reducing" represents reducing conditions and "Non-reducing" represents non-reducing conditions.

Unless defined otherwise, all technical and scientific terms used herein have the same meanings as appreciated by those skilled in the field to which the present invention pertains. In general, the nomenclature used herein is well-known in the art and is ordinarily used.

In one aspect, the present invention is directed to an antibody or an antigen-binding fragment thereof that specifically binds to human delta-like 1 homolog (*Drosophila*) (DLK1) including the following heavy- and light-chain variable regions:

a heavy-chain variable region including at least one heavy-chain CDR1 selected from the group consisting of SEQ ID. NOS: 2, 16, 30, 44, 58, 72, and 86, at least one heavy-chain CDR2 selected from the group consisting of SEQ ID. NOS: 4, 18, 32, 46, 60, 74, and 88, and at least one heavy-chain CDR3 selected from the group consisting of SEQ ID NOS: 6, 20, 34, 48, 62, 76, and 90; and a light-chain variable region including at least one light-chain CDR1 selected from the group consisting of SEQ ID NOS: 9, 23, 37, 51, 65, 79, 93, 115, and 121, at least one light-chain CDR2 selected from the group consisting of SEQ ID NOS: 11, 25, 39, 53, 67, 81, and 95, and at least one light-chain CDR3 selected from the group consisting of SEQ ID NOS: 13, 27, 41, 55, 69, 83, 97, 116, and 125.

For example, the antibody according to the invention can specifically bind to the extracellular domain of human DLK1.

The present inventors selected two kinds of DLK1 antibodies (18A5, 27F7) through analysis of antibody characteristics such as affinity, determination of binding sites, cross-linking between interspecies antigens and specific binding to DLK1 on the cell surface by screening seven kinds of novel human anti-DLK1 monoclonal antibodies with high affinity to the extracellular domain of human DLK1 proteins using a phage display method, and identified that the two antibodies bound to antigens and were then internalized into the cells, and identified an cytotoxic effect through a Fab ZAP assay.

In addition, the present inventors further selected two kinds of 18A5 antibody variants (18A5_LS_1A10 and 18A5_AM_1A12) through affinity maturation and the characterization of the antibodies as described above.

The present inventors completed the present invention by identifying that the selected human anti-DLK1 monoclonal antibody can be used as an antibody-drug conjugate (ADC).

As used herein, the term "antibody" refers to an anti-DLK1 antibody that specifically binds to DLK1, in particular, the extracellular domain of human DLK1 protein. The scope of the present invention includes not only a complete antibody specifically binding to DLK1, but also an antigen-binding fragment of the antibody molecule.

The complete antibody refers to a structure having two full-length light chains and two full-length heavy chains, wherein each light chain is linked to a corresponding heavy chain by a disulfide bond. The heavy-chain constant region has gamma (γ), mu (μ), alpha (α), delta (δ), and epsilon (ε) types and is subclassified into gamma 1 (γ1), gamma 2 (γ2), gamma 3 (γ3), gamma 4 (γ4), alpha 1 (α1) and alpha 2 (α2). The constant region of the light chain has kappa (κ) and lambda (λ) types.

The antigen-binding fragment of an antibody or antibody fragment refers to a fragment that at least has antigen-binding capacity and includes Fab, F(ab'), F(ab')2, and Fv. Among the antibody fragments, Fab refers to a structure including a variable region of each of the heavy chain and the light chain, the constant domain of the light chain, and the first constant domain (CH1) of the heavy chain, each having one antigen-binding site. Fab' is different from Fab in that it further includes a hinge region including at least one cysteine residue at the C-terminus of the CH1 domain of the heavy chain.

F(ab')2 is created by a disulfide bond between cysteine residues in the hinge region of Fab'. Fv is the minimal antibody fragment having only a heavy-chain variable region and a light-chain variable region, and recombinant technology for producing Fv is disclosed in PCT International Publications such as WO 88/10649, WO 88/106630, WO 88/07085, WO 88/07086 and WO 88/09344. Two-chain Fv is a fragment wherein the variable region of the heavy chain and the variable region of the light chain are linked by a non-covalent bond, and single-chain Fv is a fragment wherein the variable region of the heavy chain and the variable region of the light chain are generally linked by a covalent bond via a peptide linker therebetween, or are directly linked at the C-terminal, forming a dimer-shaped structure, like the two-chain Fv. Such antibody fragments may be obtained using proteases (e.g., Fabs can be obtained by restriction-cleaving the whole antibody with papain, and the F(ab')2 fragment can be obtained by restriction-cleaving the whole antibody with pepsin), and may be prepared by genetic recombination techniques.

In one embodiment, the antibody of the present invention is an Fv form (for example, scFv), or a complete antibody form. In addition, the heavy-chain constant region may be selected from gamma (γ), mu (u), alpha (α), delta (δ) and epsilon (ε) isotypes. For example, the constant region may be gamma 1 (IgG1), gamma 3 (IgG3) or gamma 4 (IgG4). The light-chain constant region may be kappa or lambda.

As used herein, the term "heavy chain" encompasses both a full-length heavy chain, which includes a variable domain (VH) containing an amino acid sequence having a sufficient variable region sequence for imparting specificity to an antigen and three constant domains (CH1, CH2 and CH3), and a fragment thereof. As used herein, the term "light chain" encompasses both a full-length light chain, which includes a variable domain (VL) containing an amino acid sequence having a sufficient variable region sequence for imparting specificity to an antigen and a constant domain (CL), and a fragment thereof.

The antibody of the present invention includes, but is not limited to, monoclonal antibodies, multispecific antibodies, human antibodies, humanized antibodies, chimeric antibodies, single chain Fvs (scFVs), single chain antibodies, Fab fragments, F(ab') fragments, disulfide-bond Fvs (sdFVs), anti-idiotypic (anti-Id) antibodies, epitope-binding fragments of such antibodies, or the like.

The monoclonal antibody refers to an identical antibody, excluding possible naturally occurring mutations where an antibody obtained from a population of substantially homogeneous antibodies, that is, each antibody constituting the population, may be present in a minor amount. Monoclonal antibodies are highly specific and are induced against a single antigenic site. In contrast to conventional (polyclonal) antibody preparations that typically include different antibodies directed against different determinants (epitopes), each monoclonal antibody is directed against a single determinant on the antigen.

For example, monoclonal antibodies useful in the present invention may be prepared by hybridoma methods, or may be prepared using recombinant DNA methods in bacterial, eukaryotic or plant cells (see U.S. Pat. No. 4,816,567). In addition, monoclonal antibodies may be isolated from phage antibody libraries.

In an embodiment of the present invention, seven monoclonal human antibodies specifically binding to DLK1 were produced by panning a native human single-chain Fv library using a phage display method.

"Phage display" is a technique for displaying a mutant polypeptide as a fusion protein with at least a part of a coat protein, for example, on the surface of the particle of a phage, for example, a fibrous phage. The usefulness of phage display is to rapidly and efficiently classify sequences that bind to target antigens with high affinity in large libraries of randomized protein mutants. Displaying peptides and protein libraries on phages has been used to screen millions of polypeptides in order to identify polypeptides with specific binding properties.

Phage display technology has offered a powerful tool for generating and screening novel proteins that bind to specific ligands (e.g., antigens). Using phage display technology, large libraries of protein mutants can be generated, and sequences binding with high affinity to target antigens can be rapidly classified. The nucleic acid encoding mutant polypeptides is fused with a nucleic acid sequence encoding a viral coat protein, e.g., a gene III or gene VIII protein. A monophasic phage display system, in which a nucleic acid sequence encoding a protein or polypeptide is fused with a nucleic acid sequence encoding a part of the gene III protein, has been developed. In the monophasic display system, a fused gene is expressed at a low level, a wild-type gene III protein is also expressed, and thus particle infectivity is maintained.

It is important to demonstrate the expression of peptides on the fibrous phage surface and the expression of functional antibody fragments in the peripheral cytoplasm of E. coli for the development of antibody phage display libraries. Libraries of antibody- or antigen-binding polypeptides are prepared by a number of methods, for example, methods of modifying a single gene by inserting a random DNA sequence or cloning a related gene sequence. The libraries can be screened for the expression of antibody- or antigen-binding proteins with desired characteristics.

Phage display technology has several advantages over conventional hybridomas and recombinant methods for producing antibodies having desired characteristics. This technique provides the generation of large antibody libraries with a variety of sequences within a short time without using animals. The production of hybridomas and the production of humanized antibodies may require a production time of several months. In addition, since no immunity is required, the phage antibody libraries can generate antibodies against antigens that are toxic or have low antigenicity. The phage antibody libraries can also be used to produce and identify novel therapeutic antibodies.

Techniques for generating human antibodies from immunized humans, non-immunized humans, germline sequences, or unsensitized B cell Ig repertoires using phage display libraries can be used. Various lymphatic tissues can be used to prepare unsensitized or non-immunogenic antigen-binding libraries.

Techniques for identifying and separating high-affinity antibodies from phage display libraries are important for the separation of new therapeutic antibodies. The separation of high-affinity antibodies from the libraries depends on the size of the libraries, the production efficiency in bacterial cells and the variety of libraries. The size of the libraries is reduced by inefficient folding of the antibody- or antigen-binding protein and inefficient production due to the presence of the stop codon. Expression in bacterial cells can be inhibited when the antibody- or antigen-binding domain is not properly folded. Expression can be improved by alternately mutating residues on the surface of the variable/constant interfaces or the selected CDR residues. The sequence of the framework region is an element to provide appropriate folding when generating antibody phage libraries in bacterial cells.

It is important to generate various libraries of antibody- or antigen-binding proteins in the separation of high-affinity antibodies. CDR3 regions have often been found to participate in antigen binding. Since the CDR3 region on the heavy chain varies considerably in terms of size, sequence and structurally dimensional morphology, various libraries can be prepared using the same.

Also, diversity can be created by randomizing the CDR regions of variable heavy and light chains using all 20 amino acids at each position. The use of all 20 amino acids results in antibody sequences with increased diversity and an increased chance of identifying new antibodies.

The term "epitope" refers to a protein determinant to which an antibody can specifically bind. Epitopes usually consist of a group of chemically active surface molecules, such as amino acids or sugar side chains, and generally have not only specific three-dimensional structural characteristics but also specific charge characteristics. Three-dimensional epitopes and non-three-dimensional epitopes are distinguished in that the binding to the former is lost in the presence of a denatured solvent, while the binding to the latter is not lost.

The non-human (e.g., murine) antibody of the "humanized" form is a chimeric antibody containing a minimal sequence derived from non-human immunoglobulin. In most cases, the humanized antibody is a human immunoglobulin (receptor antibody) in which a residue from the hypervariable region of a receptor is replaced with a residue from the hypervariable region of non-human species (donor antibody), such as a mouse, rat, rabbit, or non-human primate having the desired specificity, affinity, and ability.

The term "human antibody" as used herein refers to a molecule derived from human immunoglobulin, in which all the amino acid sequences constituting the antibody including a complementarity-determining region and a structural region are composed of human immunoglobulins.

The human antibody includes a fragment of the antibody that exhibits the desired biological activity as well as "chimeric" antibodies (immunoglobulins) in which the heavy and/or light-chain portions are derived from a certain species, or are identical or homologous to the corresponding sequences in an antibody belonging to a certain antibody class or subclass, but the remaining chain(s) are derived from another species or are identical or homologous to the corresponding sequences in an antibody belonging to another antibody class or subclass.

As used herein, the term "antibody variable domain" refers to light- and heavy-chain regions of an antibody molecule including the amino acid sequences of a complementarity-determining region (CDR; i.e., CDR1, CDR2, and CDR3) and a framework region (FR). VH refers to a variable domain of the heavy chain. VL refers to a variable domain of the light chain.

The term "complementarity-determining region" (CDR; i.e., CDR1, CDR2, and CDR3) refers to an amino acid residue of the antibody variable domain that is necessary for antigen binding. Each variable domain typically has three CDR regions, identified as CDR1, CDR2, and CDR3.

In the present invention, the antibody or antigen-binding fragment thereof that binds to DLK1 may specifically include the CDR sequences shown in Table 1 below. It was identified that, of these, two anti-DLK1 antibodies (18A5, 27F7) and two other 18A5 antibody variants (18A5_LS_1A10, 18A5_AM_1A12) can be developed as anti-DLK1 antibody-drug conjugates that are capable of binding to cells overexpressing DLK1 and killing cancer cells while targeting DLK1 expressed on the surface of cancer cells. (Examples 3, 4, 8 and 9).

TABLE 1

DLK1 monoclones and heavy-chain and light-chain variable domains of selected 18A5 antibody variants

| Clone | FR1 | CDR1 | FR2 | CDR2 | FR3 | CDR3 | FR4 | SEQ ID NO. |
|---|---|---|---|---|---|---|---|---|
| 17B11-HC | QVQLVE SGGTLV QPGGSLR LSCAAS | GFTFSS HA | MSWVRQ TPGKGLE WVSS | ITKSGS GT | YSADSVKGRF TISRDNSKNT LYLQMNSLR AEDTAVYYC | TREGLG YYYGM DV | WGQGT TVTVSS | 99 |
| SEQ ID NO. | 1 | 2 | 3 | 4 | 5 | 6 | 7 | |
| 17B11-LC | QLVLTQP PSVSGAP GQRVIIS CTGS | SSNIGA GYD | VHWYQQ LPGTAPR LLIY | GST | NRPSGVPDRF SGSKSGTSAS LAITGLQAED EADYYC | QSYDNS LSAHYV | FGTGTK VTVL | 100 |
| SEQ ID NO. | 8 | 9 | 10 | 11 | 12 | 13 | 14 | |
| 18A5-HC | QVQLVQ SGGAVV QPGHSLR LSCEAS | GFKFK DYG | MHWVRQ APGKGLE WLAV | ISHDGR NK | NYADSVKGR LTISRDNSKN TLSFQMNSLR AEDTAVYYC | VRDWSY AFDI | WGQGT LVTVSS | 101 |
| SEQ ID NO. | 15 | 16 | 17 | 18 | 19 | 20 | 21 | |
| 18A5-LC | DIQMTQS PSFLSAS VGDRVN ITCRAS | QDISR R | LAWYQQ KPGKAPK LLIY | GAA | SLQSAVASRF SGSGSGTEFT LTISSLQPEDF ANYYC | QQIYTTP KVEIK | FGGGT | 102 |

TABLE 1-continued

DLK1 monoclones and heavy-chain and light-chain variable domains of selected 18A5 antibody variants

| Clone | FR1 | CDR1 | FR2 | CDR2 | FR3 | CDR3 | FR4 | SEQ ID NO. |
|---|---|---|---|---|---|---|---|---|
| SEQ ID NO. | 22 | 23 | 24 | 25 | 26 | 27 | 28 | |
| 20D3-HC | QMQLVQSGGGLVQPGRSLRLSCAAS | GFTFDDYA | MHWVRQAPGKGLEWVSG | ISWNSGSI | GYADSVKGRFTISRDNAKNSLYLQMNSLRAEDTAVYYC | TKGPGLATGKVYFNS | WGQGTQVTVSS | 103 |
| SEQ ID NO. | 29 | 30 | 31 | 32 | 33 | 34 | 35 | |
| 20D3-LC | DIQMTQSPSSVSASVGDRVTITCRAS | QRISSW | LAWYQQKPGRAPKLLIH | SAS | TLHNGVPSRFSGSASGTDFTLTISSLQPEDFAIYYC | QQGHSFPYT | FGQGTKLDIK | 104 |
| SEQ ID NO. | 36 | 37 | 38 | 39 | 40 | 41 | 42 | |
| 21D8-HC | QVQLVESGGGLVQPGGSLRLSCAAS | GFTFSSYW | MNWVRQAPGKGLVWVSR | ISPDGST | TYADSVKGRFTISRDNAKNTLYLQMNSLRAEDTAVYYC | ARGYSPKYPTVGLDV | WGQGTTITVSS | 105 |
| SEQ ID NO. | 43 | 44 | 45 | 46 | 47 | 48 | 49 | |
| 21D8-LC | DIVMTQSPLSSPVTLGQPASISCRSS | ESLLHSNGNTY | LTWLQQRPGQPPRLLIH | KIS | NRFSGVPDRFSGSGAGTDFTLQITRVETEDVGVYYC | VQTTQWPWT | FGQGTKVEIK | 106 |
| SEQ ID NO. | 50 | 51 | 52 | 53 | 54 | 55 | 56 | |
| 21F9-HC | QVQLVQSGAEVKKPGASVRVSCKVS | GYSLSEFP | IHWVRQAPRMGLEWMGG | SYPEDGET | LYAQKFQGRVTMTEDTSTDTAYMELSSLRSEDTAVYYC | ARLNYFESTDYWVDAFDI | WGQGTMVTVSS | 107 |
| SEQ ID NO. | 57 | 58 | 59 | 60 | 61 | 62 | 63 | |
| 21F9-LC | QLVLTQPYSVSESPGKTITISCTRS | SGSIASNF | VQWYQQRPGSAPTPVIY | EDN | QRPSGVPDRFSGSIDSSSNSASLTISGVMTEDEADYYC | QSYDSGSSWV | FGGGTKLTVL | 108 |
| SEQ ID NO. | 64 | 65 | 66 | 67 | 68 | 69 | 70 | |
| 27F7-HC | QMQLVESGGGLVKPGGSLTLSCDAT | GFNFGSYY | MNWVRQAPGKGLEWLAH | ISSTGRTI | YYADSVKGRFTISRDNAKSSLDLQMNSLRAEDTAVYYC | ARDQGYPFGMDV | WGHGTTVTVSS | 109 |
| SEQ ID NO. | 71 | 72 | 73 | 74 | 75 | 76 | 77 | |
| 27F7-LC | QLVLTQPSSVSGAPGQRVTISCTGS | SSNIGAGYD | VDWYQQLPGTAPKLLIY | GNT | NRPSGVPDRFSGSKSGTSASLAITGLQAEDDSDYYC | QSYDSSLSAWV | FGGGTKLTVL | 110 |
| SEQ ID NO. | 78 | 79 | 80 | 81 | 82 | 83 | 84 | |
| 35E2-HC | QVQLVESGGGVVQPGRSLRLSCAAS | GFTFSSYA | MHWVRQAPGKGLEWVAV | IYSGGST | YYADSVKGRFTISRDNSKNTLYLQMNSLRAEDTAVYYC | AREGSYDVMTYTRIGGYFDY | WGQGALVTVSS | 111 |

TABLE 1-continued

DLK1 monoclones and heavy-chain and light-
chain variable domains of selected 18A5 antibody variants

| Clone | FR1 | CDR1 | FR2 | CDR2 | FR3 | CDR3 | FR4 | SEQ ID NO. |
|---|---|---|---|---|---|---|---|---|
| SEQ ID NO. | 85 | 86 | 87 | 88 | 89 | 90 | 91 | |
| 35E2-LC | DIQMTQS PSSVSAS VGDRVTI TCRAS | QGISD W | VAWYQQ KPGKAPK LLIY | AAS | SLQSGVPSRFS GSGSGTEFSL TISNLQPEDFA TYYC | QQANSF PLT | FGPGTK VEIK | 112 |
| SEQ ID NO. | 92 | 93 | 94 | 95 | 96 | 97 | 98 | |
| 18A5_LS_1A10-HC | QVQLVQ SGGAVV QPGHSLR LSCEAS | GFKFK DYG | MHWVRQ APGKGLE WLAV | ISHDGR NK | NYADSVKGR LTISRDNSKN TLSFQMNSLR AEDTAVYYC | VRDWSY AFDI | WGQGT LVTVSS | 101 |
| SEQ ID NO. | 15 | 16 | 17 | 18 | 19 | 20 | 21 | |
| 18A5_LS_1A10-LC | DIQMTQS PSSLSAS LGDRVTI TCRAS | QGISSA | LAWYQQ KPGKAPK LLIY | AAS | SLQSGVPSRFS GSGSGTDFTL TINSLQPEDFA TYYC | QQSYTT PLT | FGGGT KVEIK | 126 |
| SEQ ID NO. | 117 | 115 | 24 | 95 | 118 | 116 | 28 | |
| 18A5_AM_1A12-HC | QVQLVQ SGGGVV QPGGSLR LSCAAS | GFKFK DYG | MHWVRQ APGKGLE WLAV | ISHDGR NK | NYADSVKGR LTISRDNSKN TLSFQMNSLR AEDTAVYYC | VRDWSY AFDI | WGQGT LVTVSS | 127 |
| SEQ ID NO. | 119 | 16 | 17 | 18 | 19 | 20 | 21 | |
| 18A5 AM_1A12-LC | DIQMTQS PSFLSAS VGDRVTI TCRAS | HDISSS | LAWYQQ KSGKAPK LLIY | SAS | NLKSGVPSRF SGSGSGTDFS LTISSLQPEDF ATYYC | QQSYTT VLT | FGGGT KLEIK | 128 |
| SEQ ID NO. | 120 | 121 | 122 | 39 | 123 | 124 | 125 | |

The term "framework region" (FR) refers to a variable domain residue other than a CDR residue. Each variable domain typically has four FRs, identified as FR1, FR2, FR3, and FR4.

In one embodiment of the present invention, the FR may include at least one heavy chain FR1 selected from the group consisting of SEQ ID NOS: 1, 15, 29, 43, 57, 71, 85, and 119, at least one heavy chain FR2 selected from the group consisting of SEQ ID NOS: 3, 17, 31, 45, 59, 73, and 87, at least one heavy chain FR3 selected from the group consisting of SEQ ID NOS: 5, 19, 33, 47, 61, 75, and 89, at least one heavy chain FR4 selected from the group consisting of SEQ ID NOS: 7, 21, 35, 49, 63, 77, and 91, at least one light chain FR1 selected from the group consisting of SEQ ID NOS: 8, 22, 36, 50, 64, 78, 92, 117, and 120, at least one light chain FR2 selected from the group consisting of SEQ ID NOS: 10, 24, 38, 52, 66, 80, 94, and 122, at least one light chain FR3 selected from the group SEQ ID NOS: 12, 26, 40, 54, 68, 82, 96, 118, and 123, and at least one light chain FR4 selected from the group consisting of SEQ ID NO: 14, 28, 42, 56, 70, 84, 98, and 125.

The "Fv" fragment is an antibody fragment containing complete antibody recognition and binding sites. Such a region includes a dimer, for example, scFv, that consists of one heavy-chain variable domain and one light-chain variable domain substantially tightly covalently connected to each other.

A "Fab" fragment contains variable and constant domains of the light-chain and a variable domain and a first constant domain (CH1) of the heavy chain. A F(ab')2 antibody fragment generally includes a pair of Fab fragments covalently linked via a hinge cysteine located therebetween near the carboxyl end thereof.

The "single-chain Fv" or "scFv" antibody fragment includes VH and VL domains of the antibody, wherein these domains are present in a single polypeptide chain. The Fv polypeptide may further include a polypeptide linker between the VH domain and the VL domain in order that the scFv can form a target structure for antigen binding.

The antibody according to the present invention is monovalent or bivalent and includes single or double chains. Functionally, the binding affinity for the extracellular domain of DLK1 of the antibody is within the range of $10^{-3}$ M to $10^{-12}$ M. For example, the binding affinity is $10^{-6}$ M to $10^{-12}$ M, $10^{-7}$ M to $10^{-12}$ M, $10^{-8}$ M to $10^{-12}$ M, $10^{-9}$ M to $10^{-12}$ M, $10^{-5}$ M to $10^{-11}$ M, $10^{-6}$ M to $10^{-11}$ M, $10^{-7}$ M to $10^{-11}$ M, $10^{-8}$ M to $10^{-11}$ M, $10^{-9}$ M to $10^{-11}$ M, $10^{-10}$ M to $10^{-11}$ M, $10^{-3}$ M to $10^{-10}$ M, $10^{-6}$ M to $10^{-10}$ M, $10^{-7}$ M to $10^{-10}$ M, $10^{-8}$ M to $10^{-10}$ M, $10^{-9}$ M to $10^{-10}$ M, $10^{-3}$ M to $10^{-9}$ M, $10^{-6}$ M to $10^{-9}$ M, $10^{-7}$ M to $10^{-9}$ M, $10^{-8}$ M to $10^{-9}$ M, $10^{-3}$ M to $10^{-8}$ M, $10^{-6}$ M to $10^{-8}$ M, $10^{-7}$ M to $10^{-8}$ M, $10^{-3}$ M to $10^{-7}$ M, $10^{-6}$ M to $10^{-7}$ M, or $10^{-3}$ M to $10^{-6}$ M.

In addition, the antibody according to the present invention is an antibody having increased affinity for an antigen. The term "affinity" refers to the ability to specifically recognize and bind a specific site of an antigen, and high affinity as well as specificity of the antibody for the antigen are important factors in the immune response. Affinity can be determined using any of a variety of assays known in the art, such as radioimmunoassay (RIA) and ELISA, and may be expressed in various quantitative values. The affinity of an antibody for an antigen may be generally represented by a dissociation constant ($K_d$) of a particular antibody-antigen interaction. As the $K_d$ value decreases, the affinity of the antibody for the antigen increases. For example, regarding the $K_d$ value of the antibody of the present invention, the $K_d$ value for the 18A5 antibody is 0.52 and the $K_d$ value for the 27F7 antibody is 0.22, which means that the antibodies according to the present invention are high-affinity antibodies specifically bonding to human DLK1.

In addition, the antibody or antigen-binding fragment thereof that binds to the extracellular domain of DLK1 may include a heavy-chain variable region including a sequence having at least 90% homology with a sequence selected from the group consisting of SEQ ID NOS: 99, 101, 103, 105, 107, 109, 111, and 127. The antibody or antigen-binding fragment thereof that binds to the extracellular domain of DLK1 may include a light-chain variable region selected from the group consisting of SEQ ID NOS: 99, 101, 103, 105, 107, 109, 111, and 127.

In addition, the antibody or antigen-binding fragment thereof that binds to the extracellular domain of DLK1 may include a light-chain variable region including a sequence having at least 90% homology with a sequence selected from the group consisting of SEQ ID NOS: 100, 102, 104, 106, 108, 110, 112, 126, and 128. The antibody or antigen-binding fragment thereof that binds to the extracellular domain of DLK1 may include a light-chain variable region selected from the group consisting of SEQ ID NOS: 100, 102, 104, 106, 108, 110, 112, 126, and 128.

The antibody or antibody fragment of the present invention may include the sequence of the antibody mentioned herein as well as biological equivalents thereof, as long as it can specifically recognize the extracellular domain of DLK1. For example, additional changes can be made to the amino acid sequence of the antibody in order to further improve the binding affinity and/or other biological properties of the antibody. Such modifications include, for example, deletion, insertion, and/or substitution of the amino acid sequence residues of the antibody. Such amino acid variations are based on the relative similarity of amino acid side chain substituents, such as the hydrophobicity, hydrophilicity, charge, and size thereof. It can be seen through analysis of the size, shape, and type of amino acid side chain substituents that all of arginine, lysine, and histidine are positively charged residues; alanine, glycine, and serine have similar sizes; and phenylalanine, tryptophan, and tyrosine have similar shapes. Thus, based on these considerations, arginine, lysine, and histidine; alanine, glycine, and serine; and phenylalanine, tryptophan, and tyrosine may be considered as biologically functional equivalents.

When taking into consideration variations having biologically equivalent activity, the antibody or a nucleotide molecule encoding the same according to the present invention is interpreted to include a sequence having a substantial identity with the sequence set forth in the sequence number. The term "substantial identity" means that a sequence has a homology of at least 90%, most preferably a homology of at least 95%, at least 96%, at least 97%, at least 98%, and at least 99%, when aligning the sequence of the present invention with any other sequence so as to correspond to each other as much as possible and analyzing the aligned sequence using algorithms commonly used in the art. The alignment method for sequence comparison is well-known in the art. The NCBI Basic Local Alignment Search Tool (BLAST) is accessible through NCBI or the like and can be used in conjunction with sequence analysis programs such as BLASTP, BLASM, BLASTX, TBLASTN, and TBLASTX over the Internet. BLAST is available at www.ncbi.nlm.nih.gov/BLAST/. A method of comparing sequence homology using this program can be found at www.ncbi.nlm.nih.gov/BLAST/blast help.html.

Based on this, the antibody or antigen-binding fragment thereof according to the present invention can have a homology of 90%, 91%, 92%, 93%, 94%, 95%, 96%, 97%, 98%, or 99% or more. Such homology can be determined through sequence comparison and/or alignment by methods known in the art. For example, the percentage sequence homology of the nucleic acid or protein according to the present invention can be determined using a sequence comparison algorithm (i.e., BLAST or BLAST 2.0), manual alignment, or visual inspection.

In another aspect of the present invention, provided is a nucleic acid encoding the antibody or an antigen-binding fragment thereof.

By isolating the nucleic acid encoding the antibody or an antigen-binding fragment thereof according to the present invention, an antibody or antigen-binding fragment thereof can be produced recombinantly. The nucleic acid is isolated and inserted into a replicable vector, followed by further cloning (amplification of DNA) or further expression. Based on this, in another aspect, the present invention is directed to a vector including the nucleic acid.

The term "nucleic acid" is intended to encompass both DNA (gDNA and cDNA) and RNA molecules, and a nucleotide, which is a basic constituent unit of a nucleic acid, includes naturally derived nucleotides as well as analogues, wherein sugar or base moieties are modified. The sequence of the nucleic acid encoding heavy- and light-chain variable regions of the present invention can vary. Such variation includes addition, deletion, or non-conservative or conservative substitution of nucleotides.

The DNA encoding the antibody can be easily separated or synthesized using conventional procedures (for example, using an oligonucleotide probe capable of specifically binding to DNA encoding heavy and light chains of the antibody). A variety of vectors are obtainable. Vector components generally include, but are not limited to, one or more of the following components: signal sequences, replication origins, one or more marker genes, enhancer elements, promoters, and transcription termination sequences.

As used herein, the term "vector" refers to a means for expressing target genes in host cells and includes plasmid vectors, cosmid vectors, and viral vectors such as bacteriophage vectors, adenovirus vectors, retroviral vectors, and adeno-associated viral vectors. The polynucleotide encoding the antibody in the vector is operably linked to a promoter.

The term "operably linked" means a functional linkage between a nucleic acid expression regulation sequence (e.g., promoter, signal sequence, or array of transcription regulator binding sites) and other nucleic acid sequence, and enables the regulation sequence to regulate the transcription and/or translation of the other nucleic acid sequence.

When a prokaryotic cell is used as a host, it generally includes a potent promoter capable of conducting transcription (such as a tac promoter, lac promoter, lacUV5 promoter, 1pp promoter, pLλ promoter, pRλ promoter, racy promoter, amp promoter, recA promoter, SP6 promoter, trp promoter, or T7 promoter), a ribosome-binding site for initiation of translation, and a transcription/translation termination sequence. In addition, for example, when a eukaryotic cell is used as a host, it includes a promoter (e.g., a metallothionein promoter, a β-actin promoter, a human hemoglobin promoter, and a human muscle creatine promoter) derived from the genome of mammalian cells, or a promoter derived from a mammalian virus such as an adenovirus late promoter, vaccinia virus 7.5K promoter, SV40 promoter, cytomegalovirus (CMV) promoter, HSV tk promoter, mouse mammary tumor virus (MMTV) promoter, HIV LTR promoter, Moloney virus promoter, Epstein-Barr virus (EBV) promoter, and Rous sarcoma virus (RSV) promoter, and generally has a polyadenylation sequence as a transcription termination sequence.

Optionally, the vector may be fused with another sequence in order to facilitate purification of the antibody expressed therefrom. The sequence to be fused includes, for example, glutathione S-transferase (Pharmacia, USA), maltose-binding protein (NEB, USA), FLAG (IBI, USA), 6×His (hexahistidine; Qiagen, USA), and the like.

The vector includes antibiotic-resistant genes commonly used in the art as selectable markers, and examples thereof include genes conferring resistance to ampicillin, gentamycin, carbenicillin, chloramphenicol, streptomycin, kanamycin, geneticin, neomycin, and tetracycline.

In another aspect, the present invention is directed to a cell transformed with the above-mentioned vector. The cell used to produce the antibody of the present invention may be a prokaryote, yeast, or higher eukaryotic cell, but is not limited thereto.

Prokaryotic host cells such as *Escherichia coli*, the genus *Bacillus*, such as *Bacillus subtilis* and *Bacillus thuringiensis*, *Streptomyces* spp., *Pseudomonas* spp. (for example, *Pseudomonas putida*), *Proteus mirabilis*, and *Staphylococcus* spp. (for example, *Staphylococcus carnosus*) can be used.

Interest in animal cells is the greatest, and examples of useful host cell lines include, but are not limited to, COS-7, BHK, CHO, CHOK1, DXB-11, DG-44, CHO/-DHFR, CV1, COS-7, HEK293, BHK, TM4, VERO, HELA, MDCK, BRL 3A, W138, Hep G2, SK-Hep, MMT, TRI, MRC 5, FS4, 3T3, RIN, A549, PC12, K562, PER.C6, SP2/0, NS-0, U20S, and HT1080.

In another aspect, the present invention is directed to a method of producing the antibody or an antigen-binding fragment thereof including the following steps: (α) culturing the cells; and (b) recovering an antibody or an antigen-binding fragment thereof from the cultured cells.

The cells can be cultured in various media. Any commercially available medium can be used as a culture medium without limitation. All other essential supplements well-known to those skilled in the art may be included in appropriate concentrations. Culture conditions such as temperature and pH are conventionally used with host cells selected for expression, as will be apparent to those skilled in the art.

The recovery of the antibody or antigen-binding fragment thereof can be carried out, for example, by centrifugation or ultrafiltration to remove impurities and purification of the resulting product using, for example, affinity chromatography. Other additional purification techniques such as anion or cation exchange chromatography, hydrophobic interaction chromatography, and hydroxyapatite (HA) chromatography may be used.

In another aspect, the present invention is directed to an antibody-drug conjugate (ADC) including the antibody or an antigen-binding fragment thereof and a drug.

With regard to the antibody-drug conjugate, the anticancer drug should be stably bound to the antigen until the anticancer drug is delivered to the target cancer cell. The drug delivered to the target should be released from the antibody and induce the death of the target cell. For this purpose, the drug should be stably bound to the antibody, and at the same time, should exhibit sufficient cytotoxicity to induce the death of the target cell when released into the target cell. According to the present invention, when the antibody or the antigen-binding fragment thereof is conjugated with the drug, the drug can be effectively, specifically, and selectively delivered by specifically binding to cells expressing human DLK1.

The drug, which is an agent exhibiting a pharmacological effect, means a compound that can be bound to an antibody or fragment thereof specific to DLK1 of the present invention, can be separated from the antibody or fragment thereof under acidic conditions, and can exhibit a therapeutic effect on a target cell. The drug may include, but is not limited to, cytotoxins, radioisotopes, antiproliferative agents, pro-apoptotic agents, chemotherapeutic agents, and therapeutic nucleic acids.

The antibody-drug conjugate can be internalized into DLK1-expressing cells and can mediate antibody-dependent cytotoxicity.

The term "cytotoxic activity" refers to a cell-killing effect, a cell-proliferation-inhibiting effect, or a cell-growth-inhibiting effect of an antibody-drug conjugate or an intracellular metabolite of an antibody-drug conjugate. Cytotoxic activity may be expressed as an $IC_{50}$ value, indicating a concentration (molar or mass) per unit volume at which ½ of cells survive.

The term "cytotoxin" generally refers to an agent that inhibits or prevents the function of cells and/or destroys the cells. Representative cytotoxins include antibiotics, tubulin polymerization inhibitors, alkylating agents that bind to and destroy DNA, and agents that destroy the functions or protein synthesis of essential cellular proteins such as protein kinases, phosphatase, topoisomerase, enzymes, and cyclins. Examples of cytotoxins include, but are not limited to, taxol, cytochalasin B, gramicidin D, ethidium bromide, emetine, mitomycin, etoposide, tenofoside, vincristine, vinblastine, colchicine, doxorubicin, daunorubicin, dihydroxy anthracene dione, mitoxantrone, mithramycin, actinomycin D, 1-dehydrotestosterone, glucocorticoids, procaine, tetracaine, lidocaine, propranolol, and puromycin and analogs or homologs thereof.

For radiotherapy applications, the anti-DLK1 antibodies according to the present invention may include high-energy radioisotopes. The radioisotopes can be directly bound to the antibody, e.g., at cysteine residues present in the antibody, or chelates can be used to mediate the binding of the antibody to the radioisotope. Radioisotopes suitable for radiotherapy include, but are not limited to, α-emitters, β-emitters, and auger electrons. Radioisotopes useful for diagnostic applications include positron emitters and γ-emitters.

Antiproliferative and apoptosis promoters include PPAR-gamma (e.g., cyclopentenone prostaglandins (cyPGs)), retinoids, triterpenoids (e.g., cycloartanes, lupanes, uric acids, oleananes, friedelanes, dammarane, cucurbitacin and limonoid triterpenoids), inhibitors of EGF receptors (e.g., HERO), rapamycin, calcitriol (1,25-dihydroxycholecalciferol (vitamin D)), aromatase inhibitors (FEMARA® (letrozole)), telomerase inhibitors, iron-chelating agents (e.g., 3-aminopyridine-2-carboxaldehyde thiosemicarbazone (Triapine)), apoptin (viral protein 3 (VP3) from chicken anemia virus), inhibitors of Bcl-2 and Bcl-X (L), TNF-alpha, FAS ligands, TNF-associated apoptosis-inducing ligands (TRAIL/Apo2L), activators of TNF-alpha/FAS ligand/TNF-associated apoptosis-inducing ligand (TRAIL/Apo2L) signaling, and inhibitors of PI3K-Akt survival pathway signaling (e.g., UCN-01 and geldanamycin).

A "chemotherapeutic agent" is a chemical compound useful for the treatment of cancer, regardless of the mechanism of action thereof. The class of chemotherapeutic agents includes, but is not limited to, alkylating agents, metabolic antagonists, spindle toxic plant alkaloids, cytotoxic/antitumor antibiotics, topical isomerase inhibitors, antibodies, photosensitizers, and kinase inhibitors. Chemotherapeutic agents include compounds used in "targeted therapies" and traditional chemotherapy.

For diagnostic methods using anti-DLK1 antibodies, the drug may include a detectable label used to detect the presence of DLK1-expressing cells in vitro or in vivo. Radioisotopes that are detectable in vivo can be used for clinical diagnostic applications such as scintillation, magnetic resonance imaging or labels that can be detected using ultrasound. Useful scintillation labels include positron emitters and γ-emitters. Representative contrast agents for magnetic source imaging include paramagnetic or superparamagnetic ions (e.g., iron, copper, manganese, chromium, erbium, europium, dysprosium, holmium, and gadolinium), iron oxide particles, and water-soluble contrast agents. For ultrasonic detection, a gas or liquid can be trapped in the porous inorganic particles released as a microbubble contrast agent. Detectable labels useful for in-vitro detection include fluorophores, detectable epitopes or binders, and radiolabels.

The conjugates can be produced in a known manner by combining a drug with an antibody or functional equivalent. The antibody and the drug can be bound directly through their own linking groups or indirectly through linkers or other materials. The main mechanisms by which drugs are cleaved from antibodies include hydrolysis at the acidic pH of lysosomes (hydrazone, acetal and cis-aconate-like amides), peptide cleavage and disulfide reduction by lysosomal enzymes (cathepsin and other lysosomal enzymes). As a result of these various cleavage mechanisms, the mechanisms by which drugs are linked to antibodies are diverse, and any suitable linker can be used.

Suitable linking groups for binding the antibody and the drug are well known in the art, and examples thereof include disulfide groups, thioether groups, acid-degradable groups, photodegradable groups, peptidase-degradable groups, and esterase-degradable groups.

When the drug is directly bonded, the linking group may be, for example, a disulfide bond using an SH group or a bond through a maleimide. For example, the intramolecular disulfide bond of the antibody Fc region and the disulfide bond of a drug are reduced, and both are linked by a disulfide bond. There are also a method using maleimide and a method of genetically introducing cysteine into an antibody.

Antibodies and drugs may be indirectly bound through other substances (linkers). Such a linker preferably has one or more types of functional groups that react with an antibody, a drug, or both. Examples of the functional groups include amino groups, carboxyl groups, mercapto groups, maleimide groups, pyridinyl groups, and the like.

In another aspect, the present invention is directed to a bispecific antibody including the antibody or an antigen-binding fragment thereof. The bispecific antibody means an antibody capable of binding two different kinds of antigens (target proteins), and is prepared by genetic engineering or any method.

In another aspect, the present invention is directed to a pharmaceutical composition for preventing or treating cancer containing the antibody, antigen-binding fragment thereof, or antibody-drug conjugate as an active ingredient.

The present invention provides, for example, a composition for preventing or treating cancer containing: (a) a pharmaceutically effective amount of the antibody or an antigen-binding fragment thereof specifically binding to DLK1 according to the present invention; and (b) a pharmaceutically acceptable carrier. The present invention also relates to a method of preventing or treating cancer including administering an antibody or an antigen-binding fragment thereof specifically binding to DLK1 according to the present invention in an effective amount required for a patient.

Since the composition uses the aforementioned anti-DLK1 antibody or antigen-binding fragment thereof according to the present invention as an active ingredient, the description common between the two is omitted.

As used herein, the term "prevention" means any action that inhibits or delays the progress of cancer or an infectious disease by administration of a composition. As used herein, the term "treatment" means inhibition of the progress, alleviation, or removal of cancer, or inhibition of the progress, alleviation, or removal of an infectious disease.

The terms "cancer" and "cancerous" refer to or describe the physiological condition in mammals characterized in that a population of cells are growth in an uncontrolled manner.

The term "tumor" refers to any tissue mass caused by excessive cell growth or proliferation that is benign (non-cancerous) or malignant (cancerous), including pre-cancerous lesions.

The terms "cancer cell", "tumor cell", and grammatical equivalents thereof refer to a total population of cells derived from tumors and pre-cancerous lesions, including both non-tumorigenic cells including the bulk of the tumor cell population, and tumorigenic stem cells (cancer stem cells).

Antibodies of the present invention may be usefully employed both in vitro and in vivo for applications associated with DLK1-expressing cells. The monoclonal antibody, fragment thereof, or antibody-drug conjugate is as described above.

In the present invention, "cancer" includes any kind of cancer in which DLK1 is expressed. The cancer in which DLK1 is expressed is preferably selected from the group consisting of skin cancer, breast cancer, uterine cancer, colorectal cancer, kidney cancer, liver cancer, lung cancer, ovarian cancer, pancreatic cancer, gastric cancer, sarcoma, neuroblastoma, and recurring cancer, but is not limited thereto.

The pharmaceutical composition of the present invention may include a monoclonal antibody specific for DLK1, a fragment thereof, or an antibody-drug conjugate, and may further include a pharmaceutically acceptable carrier, in addition to the ingredient. The term "pharmaceutically acceptable carrier" as used herein refers to a carrier or diluent that does not impair the biological activities or properties of the administered compound and does not stimulate an organism. Pharmaceutically acceptable carriers for compositions, which are formulated into liquid solutions, are sterilized and biocompatible, and examples thereof include saline, sterile water, buffered saline, albumin injection solutions, dextrose solutions, maltodextrin solutions, glycerol, and mixtures of one or more thereof. If necessary, other conventional additives such as antioxidants, buffers and bacteriostatic agents may be added. In addition, diluents, dispersants, surfactants, binders and lubricants can be additionally added to formulate injectable solutions such as aqueous solutions, suspensions and emulsions, pills, capsules, granules, or tablets.

The pharmaceutical composition according to the present invention may be any one of various oral or parenteral formulations. In this regard, the pharmaceutical composition may be formulated using an ordinary diluent or excipient such as a filler, a thickener, a binder, a wetting agent, a disintegrant, a surfactant, or the like. Solid formulations for oral administration may include tablets, pills, powders, granules, capsules, and the like. Such a solid formulation is prepared by mixing at least one compound with at least one excipient such as starch, calcium carbonate, sucrose, lactose, or gelatin. In addition to a simple excipient, a lubricant such as magnesium stearate or talc may be further used. Liquid formulations for oral administration may include suspensions, solutions for internal use, emulsions, syrups, and the like. In addition to a simple diluent such as water or liquid paraffin, various excipients such as wetting agents, sweeteners, aromatics and preservatives may be incorporated in the liquid formulations. In addition, formulations for parenteral administration include sterile aqueous solutions, non-aqueous solvents, suspensions, emulsions, lyophilizates, suppositories, and the like. Useful non-aqueous solvents and suspensions include propylene glycol, polyethylene glycol, vegetable oils such as olive oil and injectable esters such as ethyl oleate. The basic ingredients of suppositories include Witepsol, macrogol, Tween 61, cacao butter, laurin butter, and glycerogelatin.

In another aspect, the present invention is directed to a method of inhibiting the growth of DLK1-expressing tumor cells, including bring the antibody or an antigen-binding fragment thereof or the antibody-drug conjugate into contact with the cells.

In the present invention, the tumor cell includes any kind of tumor cell in which DLK1 is expressed. The tumor cell in which DLK1 is expressed is preferably selected from the group consisting of skin cancer, breast cancer, uterine cancer, colorectal cancer, kidney cancer, liver cancer, lung cancer, ovarian cancer, pancreatic cancer, gastric cancer, sarcoma, neuroblastoma, and recurring cancer cells, but is not limited thereto.

In one embodiment of the method of inhibiting tumor cell growth, the antibody or antigen-binding fragment thereof is conjugated to a drug, such as a cytotoxin, radioisotope, or chemotherapeutic agent. In other embodiments, the antibody or antigen-binding fragment thereof is administered in combination with one or more additional anti-tumor agents. Antibodies can be used in combination with other cancer therapies such as surgery and/or radiation, and/or other anti-neoplastic agents discussed and described above.

In another aspect, the present invention is directed to a method of treating cancer including administering, to a subject, a pharmaceutically effective amount of the antibody, antigen-binding fragment thereof, or antibody-drug conjugate.

The treatment method using the antibody, antigen-binding fragment thereof, or antibody-drug conjugate includes administering a pharmaceutically effective amount of the antibody, antigen-binding fragment thereof, or antibody-drug conjugate. It will be apparent to those skilled in the art that an appropriate total daily dose can be determined by a medical specialist's suitable judgment. In addition, the antibody, antigen-binding fragment thereof, or antibody-drug conjugate may be administered in a single dose or divided into multiple doses. However, in consideration of the objects of the present invention, the specific therapeutically effective amount for a particular patient is preferably determined depending upon a variety of factors, including the type and extent of the response to be achieved, as well as the presence of other agents used, the specific composition, and age, body weight, general health conditions, gender, and diet of the patient, administration time, administration route, treatment period, and drugs used in conjunction with or concurrently with the specific composition, and other similar factors well-known in the pharmaceutical field.

The subject to which the composition of the present invention is administered includes mammals including humans without limitation.

As used herein, the term "administration" refers to an action of supplying a predetermined substance to a patient by any appropriate method, and the composition according to the present invention may be orally or parenterally administered through any general route enabling the composition to be delivered to a target tissue.

In another aspect, the present invention is directed to a composition for diagnosing cancer including the antibody or an antigen-binding fragment thereof. The diagnostic composition including an antibody specific for DLK1 or an antigen-binding fragment thereof according to the present invention can be used to diagnose a disease, such as cancer, related to the expression and degree of expression of DLK1.

In another aspect, the present invention is directed to a kit for diagnosing cancer containing the composition for diagnosing cancer.

The composition and the cancer are as described above. In addition, the kit for diagnosing cancer may further include a composition, solution, or device having one or more other components suitable for the analysis method.

In one embodiment, the kit may include a bottle, vial, bag, needle, or syringe. The container may be made from various materials, such as glass, plastic, or metal. The label on the container may provide instructions for use. The kit may further include other materials desirable from commercial and usage perspectives, such as other buffers, diluents, filters, needles, and syringes.

In another aspect, the present invention is directed to a chimeric antigen receptor (CAR) including an antibody or an antigen-binding fragment thereof that specifically binds to DLK1 as an antigen-binding domain.

The CAR may include an extracellular domain including an antigen-binding domain, a transmembrane domain and an intracellular signaling domain. The extracellular domain can be linked to the transmembrane domain by a linker. The extracellular domain may also include a signal peptide.

The CAR includes a single-chain variable fragment (scFv) of an antibody specific for a tumor-associated antigen (TAA) coupled to the cytoplasmic domain of a T-cell signaling molecule via a hinge and transmembrane region. Most conventional lymphocyte activating moieties include T-cell costimulatory (e.g., CD28, CD137, OX40, ICOS, and CD27) domains in tandem having T-cell triggering (e.g., CD3) moieties. CAR-mediated adoptive immunotherapy allows CAR-transplanted cells to directly recognize TAA on target tumor cells in a non-HLA-limited manner.

The present invention includes cells genetically modified to express the CAR. The cells may be immune cells, preferably T cells or NK cells.

In another aspect, the present invention is directed to a T-cell engager including the antibody or an antigen-binding fragment thereof that specifically binds to DLK1 expressed in tumor cells.

The T-cell engager can be, for example, a bispecific T-cell engager)(BiTE®). The BiTE is a class of artificial bispecific monoclonal antibodies, and is a fusion protein consisting of amino acid sequences from four different genes or two single-chain variable fragments (scFv) of different antibodies on a single peptide chain of about 55 kilodaltons. One of the scFvs binds to T cells via the CD3 receptor and the other binds to tumor cells via tumor-specific molecules. Similar to other bispecific antibodies, and unlike ordinary monoclonal antibodies, BiTE® forms a link between T cells and tumor cells. It produces proteins such as perforin and granzyme, allowing T cells to exhibit cytotoxic activity on tumor cells independent of the presence of MHC I or costimulatory molecules. These proteins enter tumor cells and initiate cell death.

EXAMPLE

Hereinafter, the present invention will be described in more detail with reference to examples. However, it will be obvious to those skilled in the art that these examples are provided only for illustration of the present invention and should not be construed as limiting the scope of the present invention.

Example 1. Production and Purification of Antigen (DLK1)

For the cloning of DLK1 gene, polymerase chain reaction (PCR) amplification was carried out by employing cDNA libraries produced from human placenta and primers (Table 2) containing restriction enzyme SfiI sites at 5' and 3' to obtain the product coding for the extracellular region of DLK1. The amplified PCR product was cloned into pYK602 vector so that the extracellular region can be fused with human Fc at the carboxy-terminus thereof (FIG. 1A).

TABLE 2

PCR primers for DLK1 cloning

| Primer name | Sequence information (5'→3') |
|---|---|
| DLK1 forward | AGGGGGCCGTGGGGCCGCTGAATGCTTCCCGGCCTGC (SEQ ID NO: 113) |
| DLK1 reverse | TAGCGGCCGACGCGGCCAACTGGCCCTCGGTGAGGAGAGG (SEQ ID NO: 114) |

The DLK1 plasmid cloned into the pYK602 vector was transfected into HEK293E cells (Invitrogen, USA) using PEI (polyethylene imine) and then the cells were cultured in a serum-free medium. On the $7^{th}$ day of culture, the cell culture medium was collected, centrifuged (6,000 rpm, 30 minutes, 44° C.), and filtered through 0.22 μm Top-filter (Millipore, USA) to remove cells and suspended solids, and then the supernatant was collected and purified with protein A beads (GE Healthcare, UK). The purity of the obtained protein was analyzed using SDS-PAGE gel under non-reducing and reducing conditions (FIG. 1B).

Example 2. Screening and Production of Human Anti-DLK1 Monoclonal Antibody

Example 2-1. Panning Through Phage Display

Bacteria were infected with a human scFv phage display library having a variety of $2.7 \times 10^{10}$ as a human antibody library phage, incubated at 30° C. for 16 hours, and then centrifuged (5,000 rpm, 10 minutes, 4° C.), and the resulting supernatant was concentrated with polyethylene glycol (PEG) and dissolved in PBS buffer to prepare a human scFv phage display library.

Figure 2:
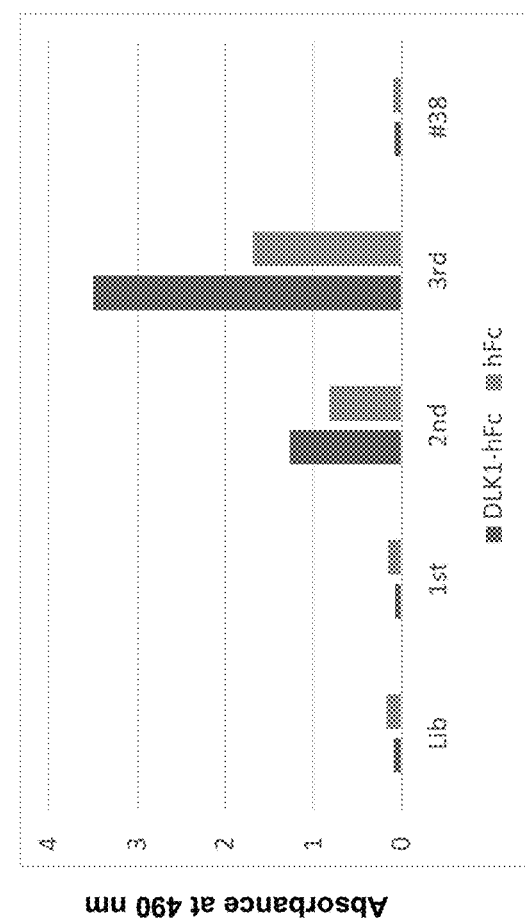
FIG. 2 is a graph showing the results of ELISA on polyclonal phage antibodies to DLK1, wherein #38 represents an antibody control group.

DLK1-hFc (100 μg/3 ml) contained in a coating buffer (15 mM $Na_2CO_3$, 35 mM $NaHCO_3$, 3 mM sodium azide, pH 9.6) was fixed on the surface of an immunosorbent tube (Nunc, USA) at 4° C. overnight and blocked at room temperature for 2 hours with skim milk (BD Biosciences, USA) dissolved in 4% PBS. Meanwhile, phages were infected with a human scFv phage display library having a variety of $2.7 \times 10^{10}$, the library phages were placed in an immunosorbent tube and then reacted at room temperature for 2 hours, and washed 20 times with 5 ml of PBS-T (0.05% Tween-20 in PBS), and only the scFv phages specifically bound to the antigen were eluted with 100 mM triethylamine. *Escherichia coli* were infected again with the eluted phage and amplified, followed by secondary and tertiary panning in a similar manner. The colony counts of the phages against the antigens after the tertiary panning were enriched more than 100-fold and had increased binding capacity to the antigen (FIG. 2) compared to the results of the primary and secondary panning, as shown in Table 3.

TABLE 3

Comparison of titer of antibodies according to panning

| Number of times panning is performed | Number of input phages | Number of bound phages |
|---|---|---|
| 1 | $2.1 \times 10^{13}$ | $3.6 \times 10^7$ |
| 2 | $1.2 \times 10^{13}$ | $7.3 \times 10^7$ |
| 3 | $2.5 \times 10^{13}$ | $2.2 \times 10^9$ |

Example 2-2. Monoclonal Selection

*Escherichia coli* were infected with phages obtained from tertiary panning with high binding capacity, and each monoclone was then incubated in a 96-deep well plate (Bionia), and a monoclonal scFv phage present in the supernatant was subjected to phage-ELISA to select monoclones. First, 100 ng of DLK1 protein per well was seeded into an immuno-96 microwell plate using a coating buffer and surface-fixed at 4° C. overnight, PBS-T containing 200 μl of 4% skim milk powder was added to all wells, and then reacted for 1 hour at 37° C. to prevent nonspecific protein binding. Then, 200 μl of each cultured single scFv phage was added and reacted at 37° C. for 2 hours, washed three times with 200 µl of PBS-T, diluted at 1:2000 with mouse anti-M13-HPR antibody (GE healthcare, UK) conjugated with HRP (horseradish peroxidase), and reacted at 37° C. for 1 hour. The resulting product was washed three times with PBS-T again, and 10 µl of 30% hydrogen peroxide ($H_2O_2$) and a tablet of 4 mg OPD (o-phenylenediamine dihydrochloride, Sigma, USA) were added to 10 ml of PC buffer (0.1M $Na_2HPO_4$, 0.005M Na-citrate, pH 5.0) and reacted in the absence of light for 10 minutes. Then, the reaction was stopped with 50 µl of 2.5M sulfuric acid ($H_2SO_4$), and absorbance was measured at 490 nm using a spectrophotometer (SpectraMax M5 spectrophotometer, Molecular Devices, USA).

Figure 3:
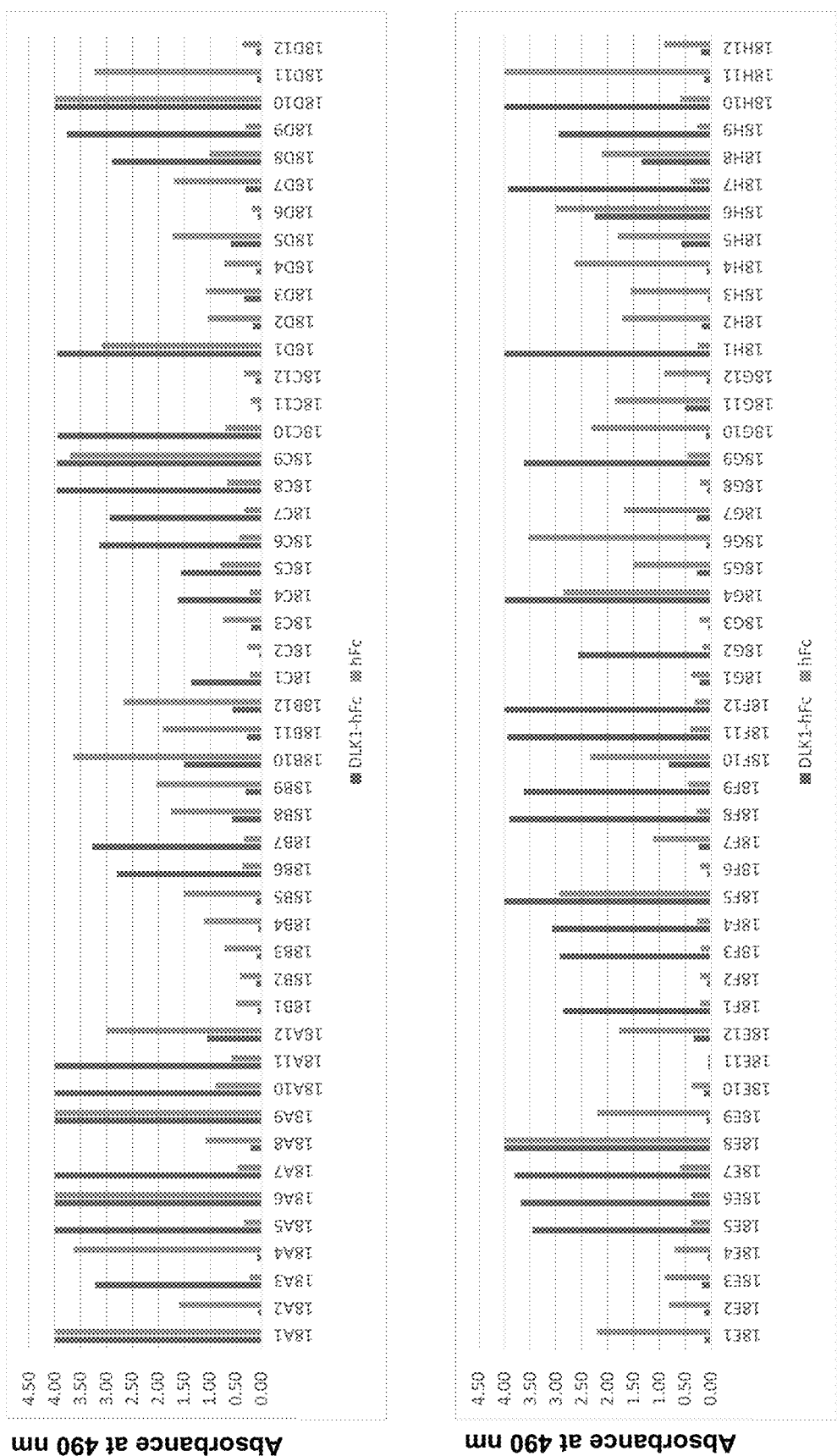
FIG. 3 shows the results of ELISA on clones expressing monoclonal scFv of DLK1.

As a result, dozens of mono-phage clones with strong binding capacity to DLK1 proteins were selected, and FIG. 3 is a diagram illustrating a representative clone among the several mono-phage clones.

Phagemid DNA was isolated from the selected monoclones using a DNA purification kit (Qiagen, Germany) and was subjected to DNA sequencing. The CDR3 site sequences of the heavy and light chains were analyzed using the Ig BLAST program, available from the NCBI website at ncbi.nlm.nih.gov/igblast. The result identified seven different clones (17B11, 18A5, 20D3, 21D8, 21F9, 27F7, 35E2) (Table 4). The sequences for the seven clones are shown in Table 5.

TABLE 4

Characteristics of seven monoclones specific to DLK1

| Clone | VH (Germ line) | Similarity | VL (Germ line) | Similarity | Group |
|---|---|---|---|---|---|
| 17B11 | IGHV3-23 | 85.7% | IGLV1-40 | 91.9% | 1 |
| 18A5 | IGHV3-30 | 82.7% | IGKV1-39 | 84.2% | 2 |
| 20D3 | IGHV3-9 | 92.9% | IGKV1-12 | 87.4% | 3 |
| 21D8 | IGHV3-74 | 93.9% | IGKV2-24 | 87.0% | 4 |
| 21F9 | IGHV1-24 | 86.7% | IGLV6-57 | 87.8% | 5 |
| 27F7 | IGHV3-11 | 82.7% | IGLV1-40 | 91.9% | 6 |
| 35E2 | IGHV3-66 | 90.7% | IGKV1-12 | 93.7% | 7 |

TABLE 5

Characteristics of heavy-chain variable region and light-chain variable region of seven monoclones specific to DLK1

| Clone | FR1 | CDR1 | FR2 | CDR2 | FR3 | CDR3 | FR4 | SEQ ID NO |
|---|---|---|---|---|---|---|---|---|
| 17B11-HC | QVQLVESGGTLVQPGGSLRLSCAAS | GFTFSSHA | MSWVRQTPGKGLEWVSS | ITKSGSGT | YSADSVKGRFTISRDNSKNTLYLQMNSLRAEDTAVYYC | TREGLGYYYGMDV | WGQGTTVTVSS | 99 |
| SEQ ID NO | 1 | 2 | 3 | 4 | 5 | 6 | 7 | |
| 17B11-LC | QLVLTQPPSVSGAPGQRVIISCTGS | SSNIGAGYD | VHWYQQLPGTAPRLLIY | GST | NRPSGVPDRFSGSKSGTSASLAITGLQAEDEADYYC | QSYDNSLSAHYV | FGTGTKVTVL | 100 |
| SEQ ID NO | 8 | 9 | 10 | 11 | 12 | 13 | 14 | |
| 18A5-HC | QVQLVQSGGAVVQPGHSLRLSCEAS | GFKFKDYG | MHWVRQAPGKGLEWLAV | ISHDGRNK | NYADSVKGRLTISRDNSKNTLSFQMNSLRAEDTAVYC | VRDWSYAFDI | WGQGTLVTVSS | 101 |
| SEQ ID NO | 15 | 16 | 17 | 18 | 19 | 20 | 21 | |
| 18A5-LC | DIQMTQSPSFLSASVGDRVNITCRAS | QDISRR | LAWYQQKPGKAPKLLIY | GAA | SLQSAVASRFSGSGSGTEFTLTISSLQPEDFANYYC | QQIYTTPLT | FGGGTKVEIK | 102 |
| SEQ ID NO | 22 | 23 | 24 | 25 | 26 | 27 | 28 | |
| 20D3-HC | QMQLVQSGGGLVQPGRSLRLSCAAS | GFTFDDYA | MHWVRQAPGKGLEWVSG | ISWNSGSI | GYADSVKGRFTISRDNAKNSLYLQMNSLRAEDTAVYC | TKGPGLATGKVYFNS | WGQGTQVTVSS | 103 |
| SEQ ID NO | 29 | 30 | 31 | 32 | 33 | 34 | 35 | |
| 20D3-LC | DIQMTQSPSSVSASVGDRVTITCRAS | QRISSW | LAWYQQKPGRAPKLLIH | SAS | TLHNGVPSRFSGSASGTDFTLTISSLQPEDFAIYYC | QQGHSFPYT | FGQGTKLDIK | 104 |

TABLE 5-continued

Characteristics of heavy-chain variable region and light-chain variable region of seven monoclones specific to DLK1

| Clone | FR1 | CDR1 | FR2 | CDR2 | FR3 | CDR3 | FR4 | SEQ ID NO |
|---|---|---|---|---|---|---|---|---|
| SEQ ID NO | 36 | 37 | 38 | 39 | 40 | 41 | 42 | |
| 21D8-HC | QVQLVESGGGLVQPGGSLRLSCAAS | GFTFSSYW | MNWVRQAPGKGLVWVSR | ISPDGSST | TYADSVKGRFTISRDNAKNTLYLQMNSLRAEDTAVYYC | ARGYSPKYPTVGLDV | WGQGTTITVSS | 105 |
| SEQ ID NO | 43 | 44 | 45 | 46 | 47 | 48 | 49 | |
| 21D8-LC | DIVMTQSPLSSPVTLGQPASISCRSS | ESLLHSNGNTY | LTWLQQRPGQPPRLLIH | KIS | NRFSGVPDRFSGSGAGTDFTLQITRVETEDVGVYYC | VQTTQWPWT | FGQGTKVEIK | 106 |
| SEQ ID NO | 50 | 51 | 52 | 53 | 54 | 55 | 56 | |
| 21F9-HC | QVQLVQSGAEVKKPGASVRVSCKVS | GYSLSEFP | IHWVRQAPRMGLEWMGG | SYPEDGET | LYAQKFQGRVTMTEDTSTDTAYMELSSLRSEDTAVYYC | ARLNYFESTDYWVDAFDI | WGQGTMVTVSS | 107 |
| SEQ ID NO | 57 | 58 | 59 | 60 | 61 | 62 | 63 | |
| 21F9-LC | QLVLTQPYSVSESPGKTITISCTRS | SGSIASNF | VQWYQQRPGSAPTPVIY | EDN | QRPSGVPDRFSGSIDSSSNSASLTISGVMTEDEADYYC | QSYDSGSSWV | FGGGTKLTVL | 108 |
| SEQ ID NO | 64 | 65 | 66 | 67 | 68 | 69 | 70 | |
| 27F7-HC | QMQLVESGGGLVKPGGSLTLSCDAT | GFNFGSYY | MNWVRQAPGKGLEWLAH | ISSTGRTI | YYADSVKGRFTISRDNAKSSLDLQMNSLRAEDTAVYYC | ARDQGYPFGMDV | WGHGTTVTVSS | 109 |
| SEQ ID NO | 71 | 72 | 73 | 74 | 75 | 76 | 77 | |
| 27F7-LC | QLVLTQPSSVSGAPGQRVTISCTGS | SSNIGAGYD | VDWYQQLPGTAPKLLIY | GNT | NRPSGVPDRFSGSKSGTSASLAITGLQAEDDSDYYC | QSYDSSLSAWV | FGGGTKLTVL | 110 |
| SEQ ID NO | 78 | 79 | 80 | 81 | 82 | 83 | 84 | |
| 35E2-HC | QVQLVESGGGVVQPGRSLRLSCAAS | GFTFSSYA | MHWVRQAPGKGLEWVAV | IYSGGST | YYADSVKGRFTISRDNSKNTLYLQMNSLRAEDTAVYYC | AREGSYDVMTYTRIGGYFDY | WGQGALVTVSS | 111 |
| SEQ ID NO | 85 | 86 | 87 | 88 | 89 | 90 | 91 | |
| 35E2-LC | DIQMTQSPSSVSASVGDRVTITCRAS | QGISDW | VAWYQQKPGKAPKLLIY | AAS | SLQSGVPSRFSGSGSGTEFSLTISNLQPEDFATYYC | QQANSFPLT | FGPGTKVEIK | 112 |
| SEQ ID NO | 92 | 93 | 94 | 95 | 96 | 97 | 98 | |

Example 2-3. Conversion of scFv Form to IgG Form

Figure 4:
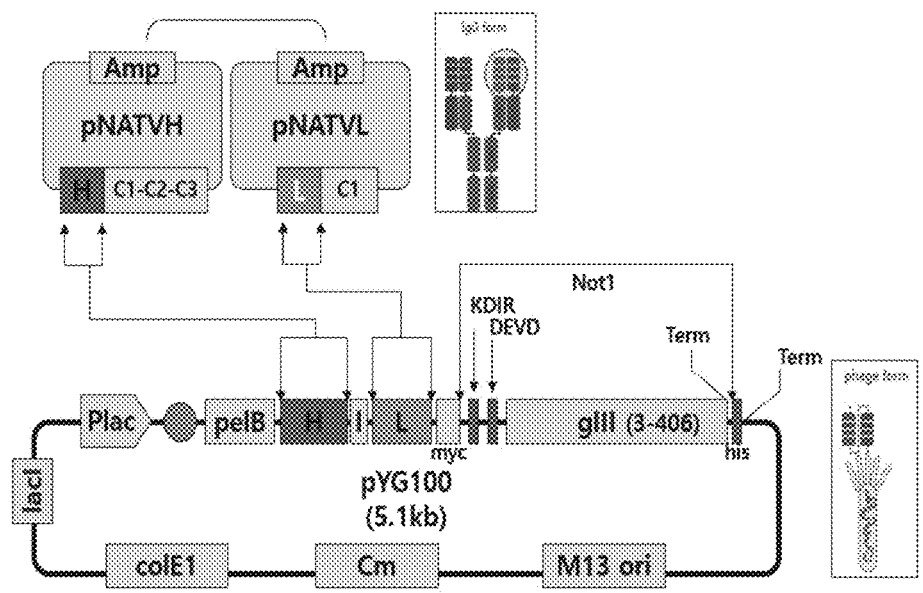
FIG. 4 shows a vector map (A) of an expression vector to convert seven kinds of monoclonal phage antibodies (17B11, 18A5, 20D3, 21D8, 21F9, 27F7, 35E2) from scFv to IgG, and results of SDS-PAGE (B) to determine the purity of the antibody converted to IgG after purification.
Figure 4:
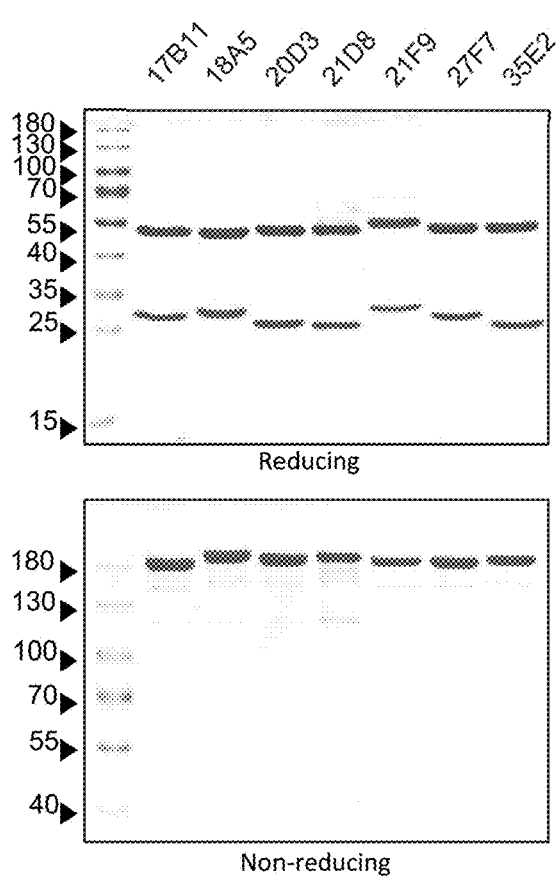

In order to convert the selected 7 monoclonal phage antibodies from scFv to IgG, the nucleotide sequences of the heavy- and light-chain variable regions were cloned into pNATVH using restriction enzyme SfiI/NheI sites, respectively, and were cloned into pNATVL using a restriction enzyme SfiI/BglII site (FIG. 4A).

The cloned pNATVH and pNATVL vectors were co-transfected into HEK293E cells at a ratio of 6:4, the supernatant was collected on the $7^{th}$ day, and cells and suspended solids were removed through centrifugation and a 0.22 μm Top-filter. The supernatant was collected and purified with protein A beads, and the purity of the purified antibodies was analyzed using SDS-PAGE under both non-reducing and reducing conditions (FIG. 4B).

Example 3. Characteristics of DLK1 Monoclonal Antibodies

Example 3-1. Determination of Affinity for DLK1 Antigen

Figure 5:
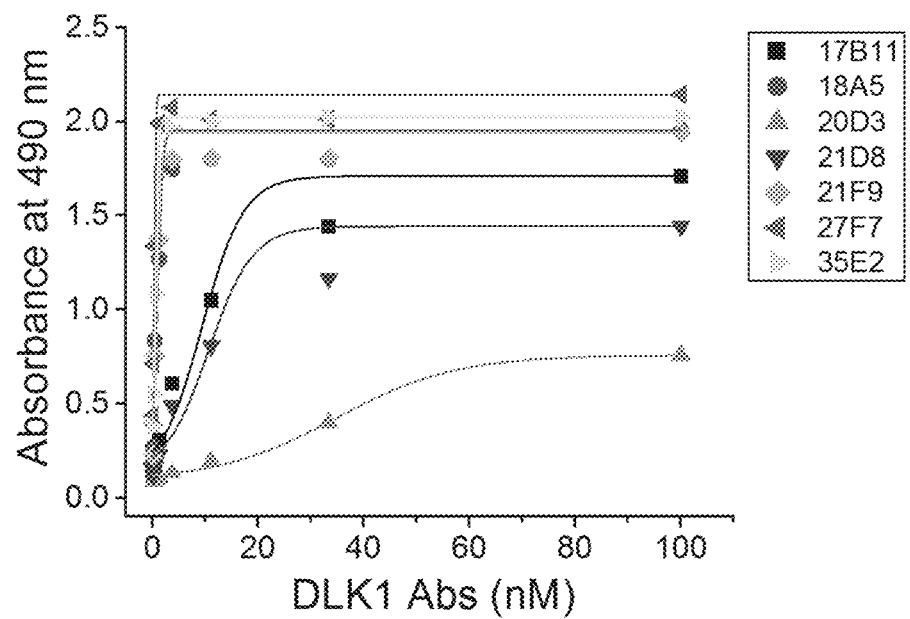
FIG. 5 shows the result of ELISA to determine the binding affinity of seven kinds of human anti-DLK1 monoclonal antibodies (17B11, 18A5, 20D3, 21D8, 21F9, 27F7, 35E2) to the DLK1 antigen.

The binding affinity of the seven human anti-DLK1 monoclonal antibodies to the antigen was measured using the ELISA method, which was the same as the phage-ELISA method described in Example 2-2 above, except that, instead of phage, seven human anti-DLK1 monoclonal antibodies were serially diluted by one-third from 100 nM to 0.046 nM and was each added in an amount of 100 μl to each well column. The measurement results were analyzed using GraphPad Prism 6 software (graphpad.com/scientific-software/prism/). The affinity dissociation constants (Kd) for the antigens of human anti-DLK1 monoclonal antibodies 17B11, 18A5, 20D3, 21D8, 21F19, 27F7 and 35E2 were 7.19, 0.52, 53.95, 8.40, 0.53, 0.22 and 0.33 nM, respectively (FIG. 5).

Example 3-2. Determination of Binding Sites (Epitopes) to DLK1 Antigen

Figure 6:
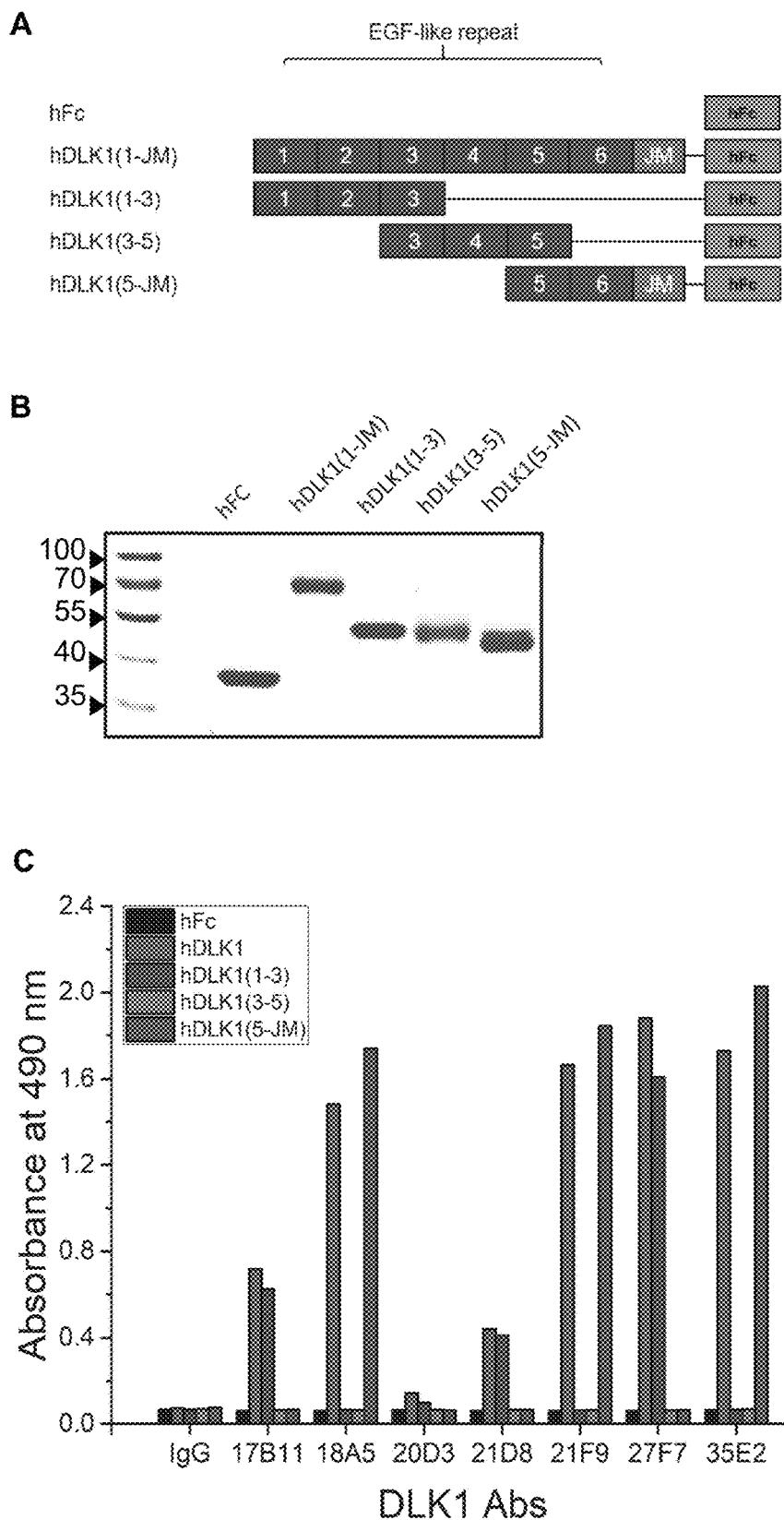
FIG. 6 shows the result (C) of ELISA to determine binding specificity of seven human anti-DLK1 monoclonal antibodies (17B11, 18A5, 20D3, 21D8, 21F9, 27F7, 35E2) to hFc protein (negative control group), and DLK1-hFc fusion proteins (A and B) including full-length or partial-length EGF-like repeat domains.

Four human-derived DLK1 recombinant proteins and hFc recombinant proteins were prepared, produced and purified in the same manner as described in Example 1 in order to determine the binding sites of the human anti-DLK1 monoclonal antibody to the antigen. (FIG. 6B). At this time, the purity of all the purified DLK1 recombinant proteins was 95% or more, and ELISA was performed on the 7 human anti-DLK1 antibodies (FIG. 6C).

The result identified that the anti-DLK1 antibodies 17B11, 20D3, 21D8 and 27F7 had the binding site in human-derived EGF-like repeat domain 1 and EGF-like repeat domain 2, and the anti-DLK1 antibodies 18A5, 21F9 and 35E2 had the binding site in the EGF-like repeat domain 6 and membrane-proximity domain (FIG. 6C).

Example 3-3. Determination of Cross-Reactivity to Other Species of DLK

Figure 7:
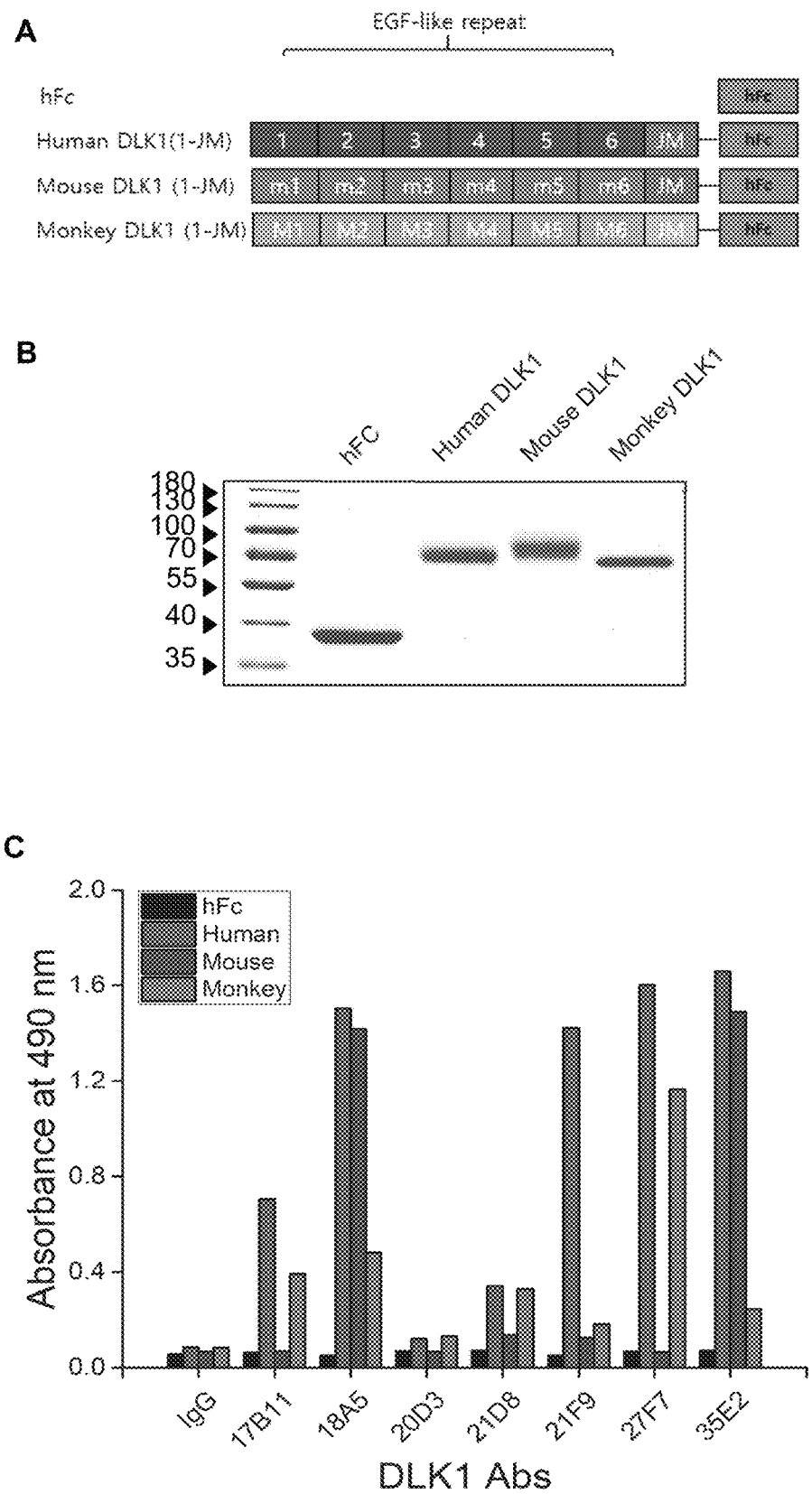
FIG. 7 shows the result of ELISA to determine the binding specificity of seven human anti-DLK1 monoclonal antibodies (17B11, 18A5, 20D3, 21D8, 21F9, 27F7, 35E2) to hFc protein (negative control group) and hFc fusion proteins (A and B) of human DLK1 (hDLK1), mouse DLK1 (mDLK1), or monkey DLK1 (MDLK1).

In order to determine the cross-reactivity of the human anti-DLK1 monoclonal antibody to DLK1 orthologues found in other species, mouse DLK1 and monkey DLK1 were prepared, produced and purified in the same manner described in Example 1, as shown in FIG. 7A. (FIG. 7B). At this time, the purity of all of the purified DLK1 recombinant proteins was 95% or more, as shown in FIG. 7B, and the binding of seven human anti-DLK1 antibodies was determined with these proteins through an ELISA method (FIG. 7C).

The result identified that the anti-DLK1 antibody 21F9 bound only to human DLK1, the anti-DLK1 antibodies 17B11, 20D3, 21D8 and 27F7 bound to human DLK1 and monkey DLK1, and the anti-DLK1 antibodies 18A5 and 35E2 bound to human DLK1, mouse DLK1 and monkey DLK1 (FIG. 7C).

Thus, based on the results of Examples 3-1 and 3-3, as human anti-DLK1 monoclonal antibodies, 20D3 having low binding affinity to human DLK1, and 21F9 and 35E2 having low binding affinity to monkey DLK1 were excluded from the human anti-DLK1 antibody selection process through characterization.

Example 3-4. Determination of Binding Specificity to DLK1 Present on Cell Surface Through FACS Analysis The binding specificity to DLK1 present on the cell surface of the human antibody according to the present invention was measured using SK-N-F1 cells, which are neuroblastoma cell lines that endogenously express MIA PaCa-2 and DLK1, which are human pancreatic cancer cell lines transformed (DLK1-overexpressing) so as to continuously express antigens. The expression of DLK1 was reduced through treatment with 20 nM of siRNA (Dharmacon, USA) for DLK1, and the antigen binding of the antibody according to the degree of expression of the antigen on the cell surface was measured through FACS analysis. Each cell was prepared in an amount of $5 \times 10^5$, and was reacted with, as primary antibodies, 2 μg/ml of human anti-DLK1 monoclonal antibodies 17B11, 18A5, 21D8 and 27F7 at 4° C. for 1 hour. Then, the cells were washed with cold PBS and then cultured at 4° C. for 1 hour using an anti-human IgG secondary antibody (Vector, USA) conjugated with fluorescein isothiocyanate (FITC, Vector, USA) fluorescence. Fluorescently stained cells were suspended in 500 μl of PBS containing 2% FBS (fetal bovine serum) and analyzed using a FACSCanto™ II flow cytometer (BD Biosciences, USA).

Figure 8:
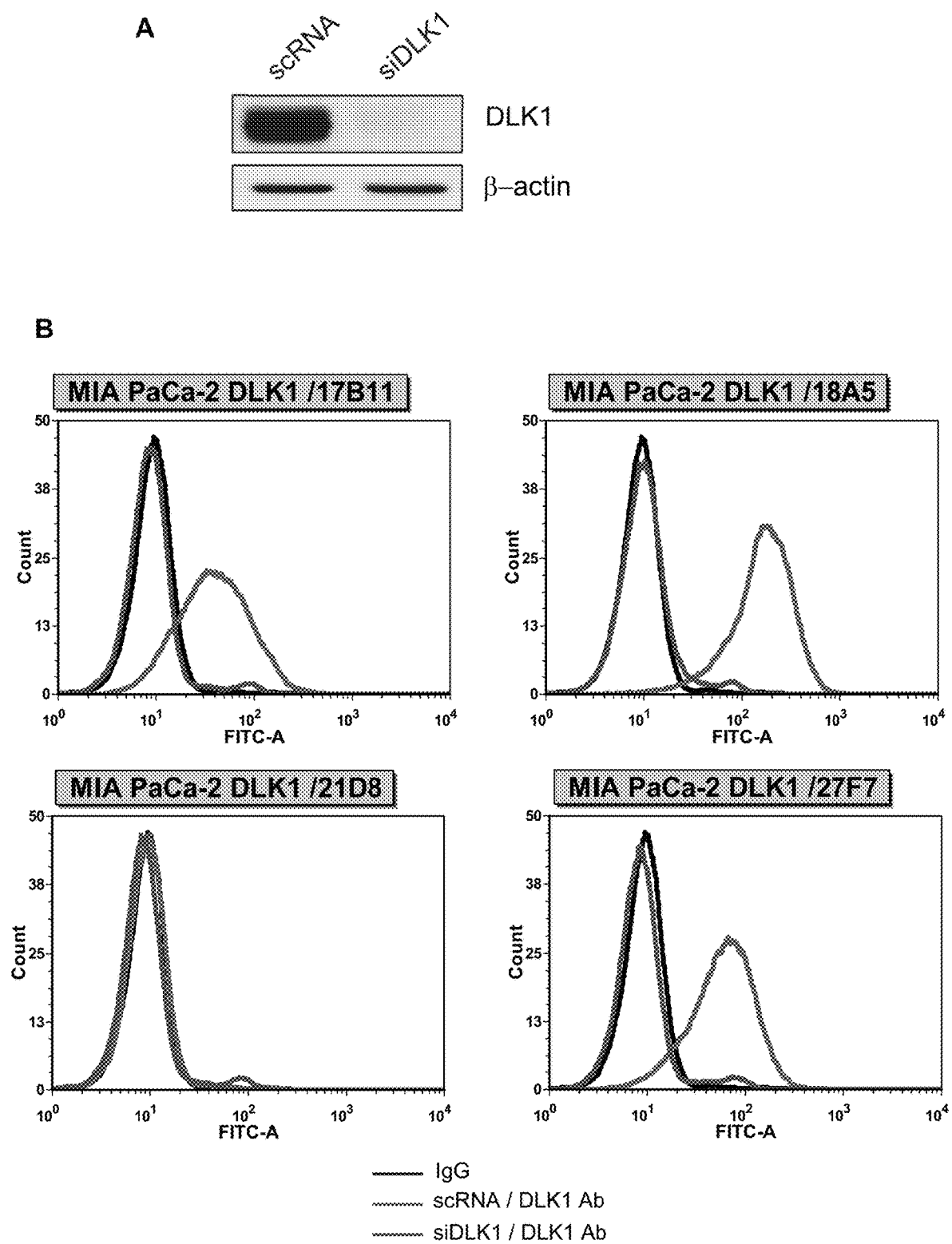
FIG. 8 shows the result of identification of the DLK1 protein expressed in MIA PaCa-2 cells overexpressing DLK1 and the decrease of DLK1 protein expression by siRNA treatment (A) and the result of fluorescence-activated cell sorting (FACS) to determine the binding capacity of human anti-DLK1 monoclonal antibodies (17B11, 18A5, 21D8, 27F7) to DLK1 present on the cell surface (B), wherein scRNA represents scrambled small interfering RNA (siRNA) and siDLK1 represents DLK1-specific siRNA.

The decrease in DLK1 expression rate due to DLK1 siRNA in MIA PaCa-2 cells overexpressing DLK1 was identified through Western blotting (FIG. 8A). The result identified that human anti-DLK1 monoclonal antibodies 17B11, 18A5 and 27F7 bound to MIA PaCa-2 cells overexpressing DLK1, and the binding thereof was removed when the expression level of DLK1 was decreased due to DLK1 siRNA (FIG. 8B). However, human anti-DLK1 monoclonal antibody 21D8 failed to bind even to MIA PaCa-2 cells overexpressing DLK1.

Figure 9:
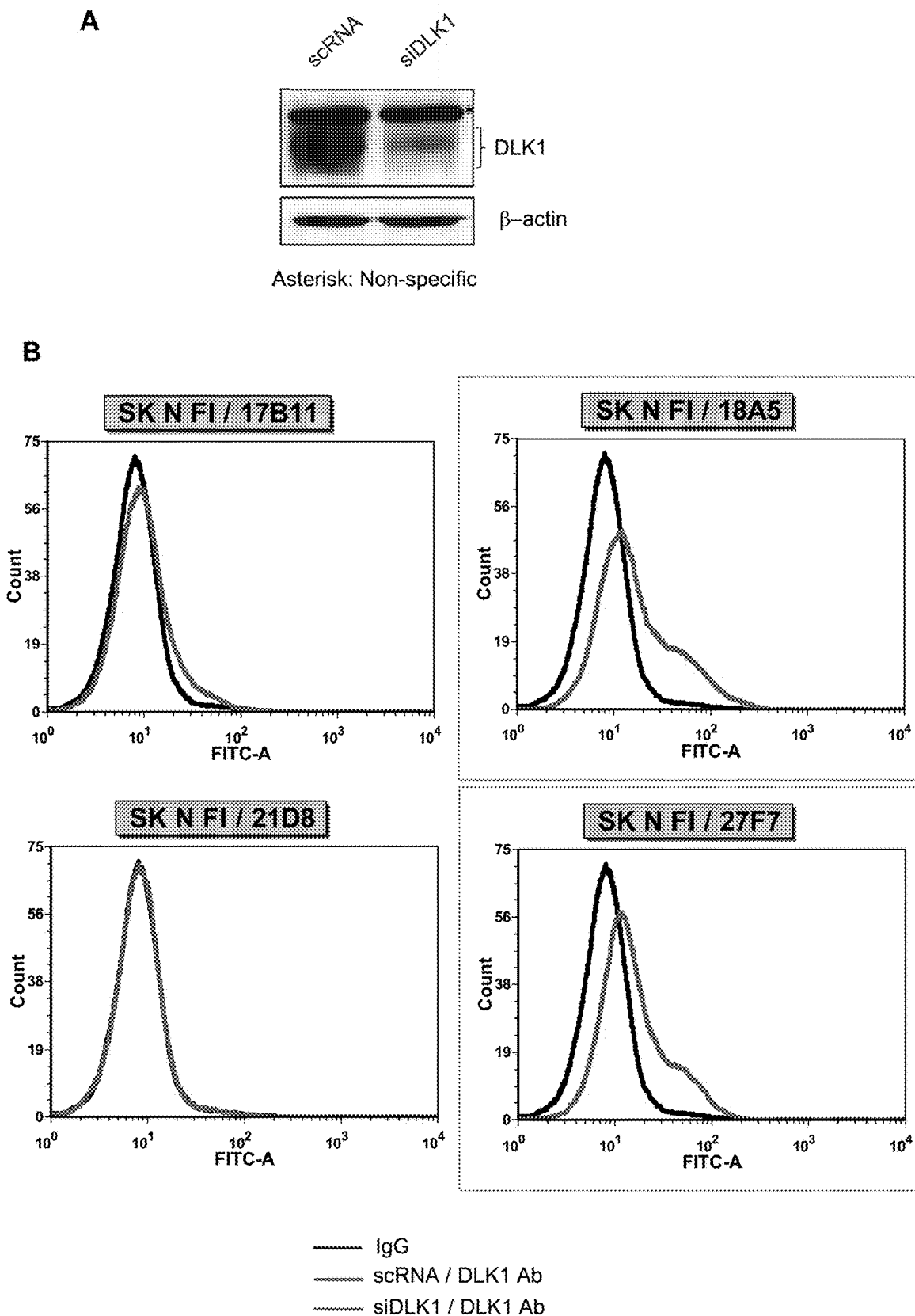
FIG. 9 shows the result of identification of the DLK1 protein endogenously expressed in SK-N-F1 cells and the decrease of DLK1 protein expression through siRNA treatment (A) and the result of use of a fluorescence-enabled cell sorter (FACS) to determine the binding of human anti-DLK1 monoclonal antibodies (17B11, 18A5, 21D8, 27F7) to DLK1 present on the cell surface (B).

In addition, in SK-N-F1 cells endogenously expressing DLK1 and in cells obtained by reducing DLK1 expression in these cells using DLK1 siRNA (FIG. 9A), human anti-DLK1 monoclonal antibodies 18A5 and 27F7 bound to SK-N-F1 cells endogenously expressing DLK1, and the binding thereof was removed when the amount of DLK1 expression was decreased due to DLK1 siRNA (FIG. 9B). However, human anti-DLK1 monoclonal antibodies 17B11 and 21D8 failed to bind even to SK-N-F1 cells endogenously expressing DLK1.

Thus, human anti-DLK1 monoclonal antibodies 17B11 and 21D8 were excluded from the human anti-DLK1 antibody selection process through characterization in Example 3-4.

Example 3-5. Determination of Cell Surface-Specific Binding Through Immunocytochemistry Analysis MIA PaCa-2 cells overexpressing DLK1 were seeded at a density of 2×10⁴ cells/well on an 8-well chamber slide (Nunc, USA) and grown in 10% FBS-containing complete DMEM (Dulbecco's Modified Eagle's Medium, GE Healthcare, USA) for two days. The next day, the medium was removed and cold DMEM containing 10 µg/ml of anti-human IgG, anti-DLK1 antibody 18A5 or 27F7 as a negative control was added and reacted at 1° C. for 1 hour such that the antibody bound to the cell surface. Antibodies that did not bind to the cells were removed by washing three times with PBS, and then the cells were fixed by reacting with PBS containing 4% paraformaldehyde at room temperature for 10 minutes. The fixed cells were washed with PBS containing 10% FBS, and then PBS containing a FITC-anti-human IgG (Vector, USA) secondary antibody at a ratio of 1:200 was added thereto and cultured in the dark for 1 hour at room temperature. Fluorescently stained cells were washed three times with PBST at three-minute intervals, and then a mounting solution containing DAPI (4',6-diamidino-2-phenylindole; Vector, USA) was dropped on the slide, the slide was covered with a cover glass to prevent the formation of bubbles, and then imaging was performed using a confocal laser scanning microscope (LSM510META, ZEISS, Germany).

Figure 10:
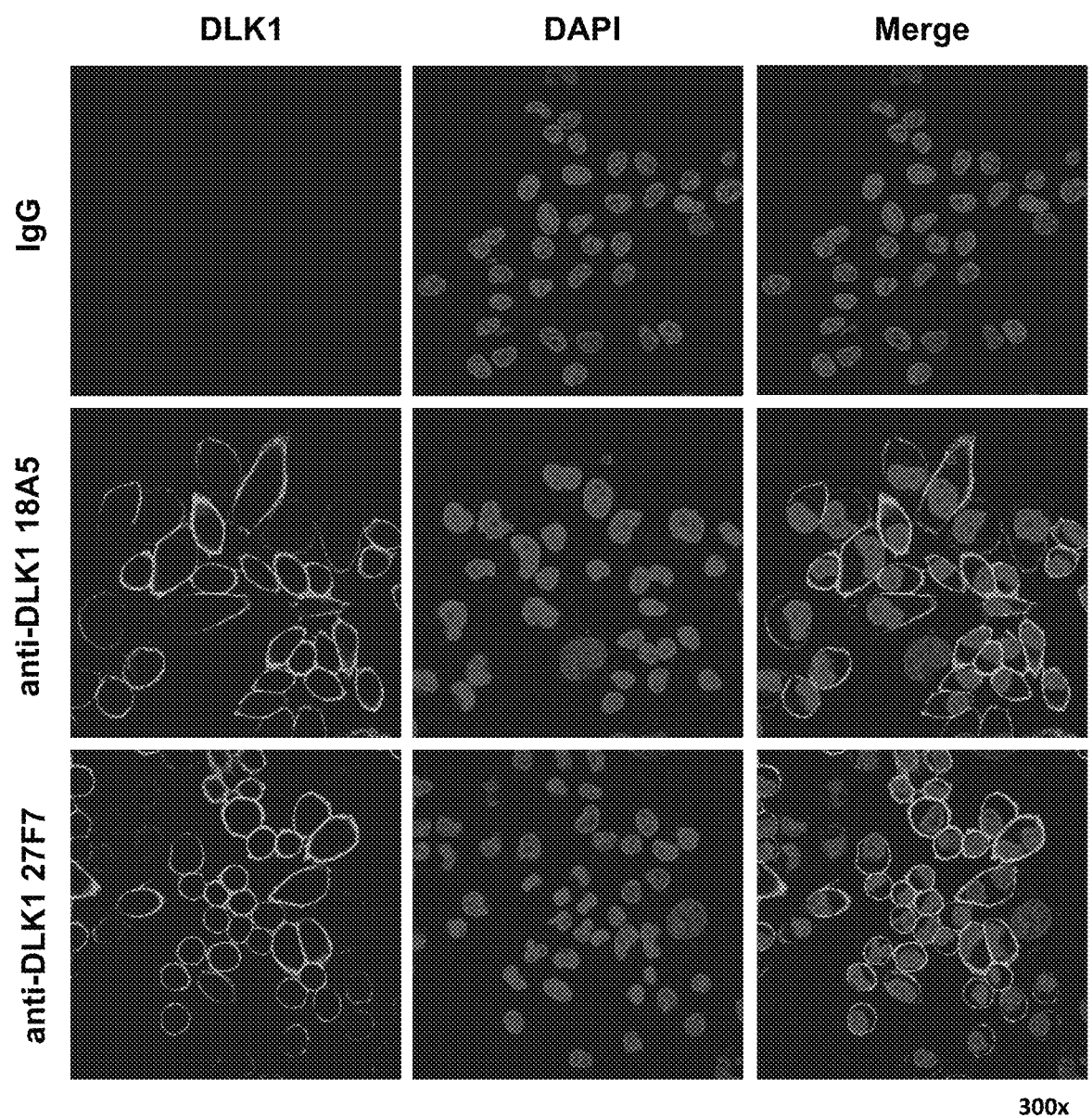
FIG. 10 shows the result of immunofluorescence to determine the cell surface-specific binding of human anti-DLK1 monoclonal antibodies (18A5, 27F7) in MIA PaCa-2 cells overexpressing DLK1.

As shown in FIG. 10, the result identified that both of the two human anti-DLK1 monoclonal antibodies (18A5, 27F7) bound to the cell membrane of MIA PaCa-2 overexpressing DLK1. Meanwhile, the anti-human IgG used as a negative control group did not bind to the cell membrane.

Example 3-6. Determination of Intracellular Internalization of Anti-DLK1 Antibodies in Human Pancreatic Cancer Cells In order to determine whether or not the anti-DLK1 antibodies 18A5 and 27F7 can be internalized into cells after binding to antigens present on the cell surface, an endocytosis assay was performed on MIA PaCa-2 cells overexpressing DLK1, and immunohistochemical staining was performed to determine the locations of the antibodies in the cells. The cells were seeded at a density of 2×10⁴ cells/well on an 8-well chamber slide, treated with 10 µg/ml of each of anti-DLK1 antibodies 18A5 and 27F7, and reacted at 4° C. for 1 hour in order to bind the antibody to the antigen present on the cell surface. Then, the cells were washed with cold PBS, the medium was replaced with complete medium pre-warmed at 37° C. to induce intracellular internalization of antibodies, and the cells were incubated under conditions of 37° C. and 5% $CO_2$ for 0.1, 0.5, 1, 2 or 4 hours. After the planned incubation time, the cells were washed three times with PBS to remove the medium and fixed with 4% paraformaldehyde. The fixed cells were washed three times with PBS, and then reacted for 1 hour at room temperature with each endosomal marker antibody diluted in PBS containing 0.2% saponin and 10% FBS. The endosomal markers used herein were anti-rabbit LAMP1 (Abcam, USA) as a late endosomal/lysosomal marker antibody, anti-mouse EEA1 (BD Biosciences, USA) as an early endosome marker antibody, and an anti-mouse transferrin receptor (TfR, BD Biosciences, USA) as an early/recycling endosome marker antibody. After binding to the marker antibody, the cells were washed three times at three-minute intervals with PBS containing 10% FBS, and then anti-human IgG (Vector, USA) conjugated with FITC as a secondary antibody of anti-DLK1 antibody, anti-rabbit IgG conjugated with Cy3 (Jackson ImmunoResearch, USA) as a secondary antibody of anti-rabbit LAMP1, and an anti-mouse IgG conjugated with Cy3 (Jackson ImmunoResearch, USA) as a secondary antibody of anti-mouse EEA1 or anti-mouse TfR were each diluted 1:200 in PBS containing 0.2% saponin and 10% FBS, and cultured in the dark at room temperature for 1 hour. Fluorescently stained cells were washed three times with PBS at intervals of three minutes, a mounting solution containing DAPI (Vector, USA) was dropped on the slide, covered with a cover glass to prevent the formation of bubbles, and then imaging was performed using a confocal laser microscope (LSM510META, ZEISS, Germany).

Figure 11:
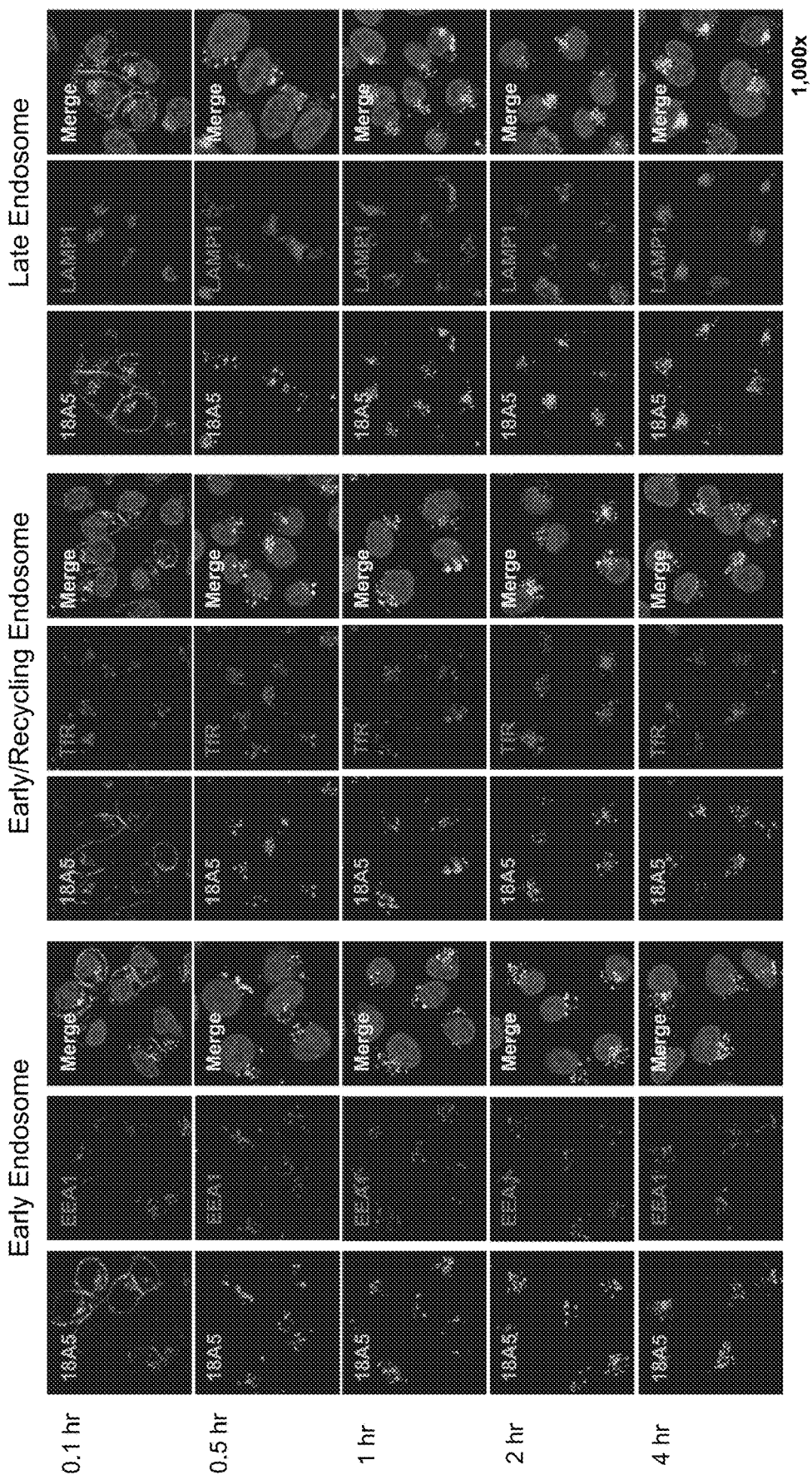
FIG. 11 shows the result of fluorescent staining identifying co-localization of human anti-DLK1 monoclonal antibody (18A5) with different endosomal markers in cells hourly in MIA PaCa-2 cells overexpressing DLK1, wherein EEA represents an early endosomal marker, TfR represents an early/recycling endosomal marker, and LAMP1 represents a late endosomal marker.
Figure 12:
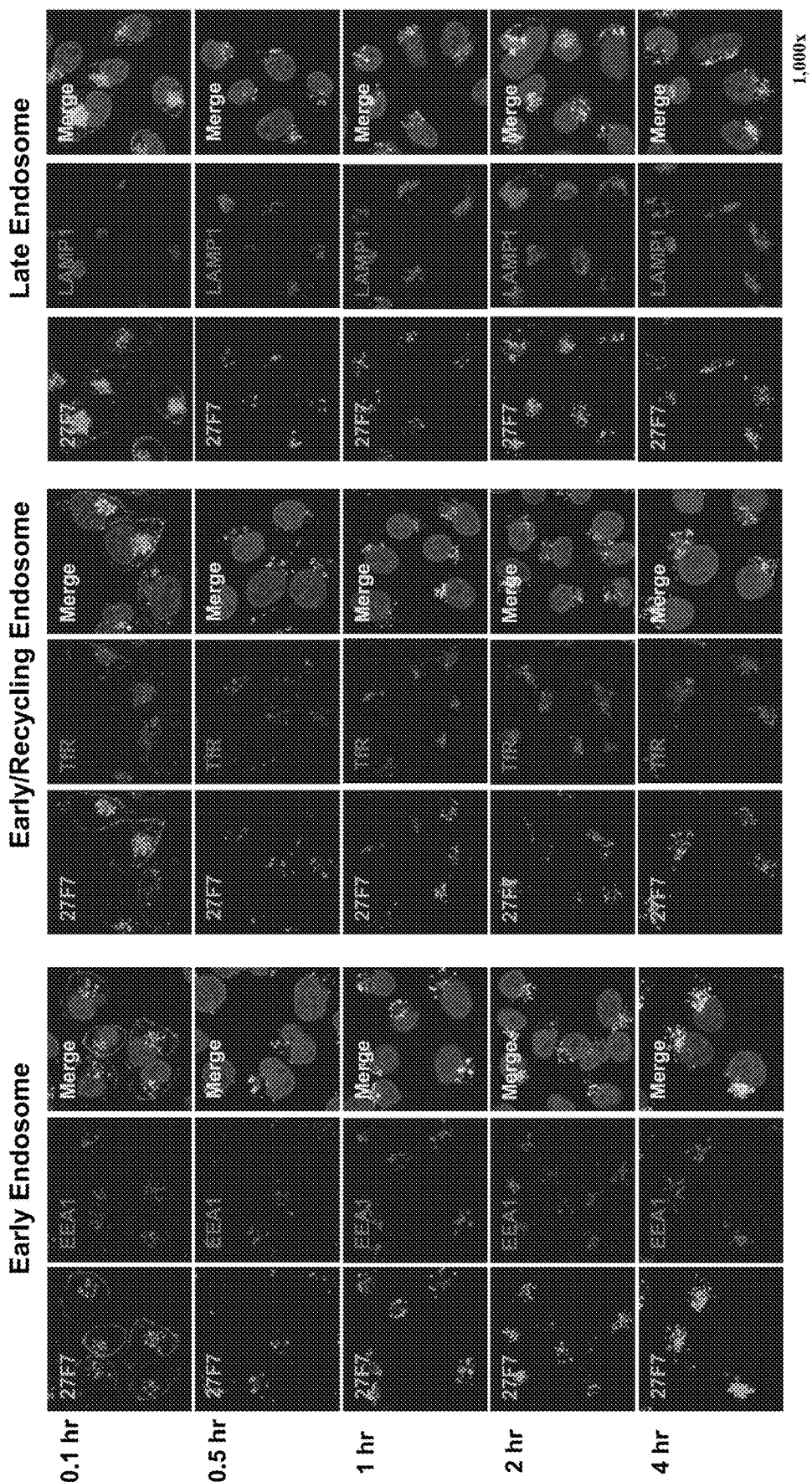
FIG. 12 shows the result of fluorescent staining identifying co-localization of human anti-DLK1 monoclonal antibody (27F7) with different endosomal markers in cells hourly in MIA PaCa-2 cells overexpressing DLK1.

The result identified that two human anti-DLK1 monoclonal antibodies were internalized into the cells starting 0.1 hours after the induction of endocytosis (FIGS. 11 and 12). Meanwhile, co-localization of the internalized anti-DLK1 antibody with an anti-EEA1 antibody or anti-TfR antibody, which is a marker antibody of early endosomes and recycling endosomes, was very frequent. Such frequency decreased over time, and the frequency of co-localization with the anti-LAMP1 antibody, which is a late endosomal/lysosomal marker antibody, increased, which identified that the anti-DLK1 antibody was delivered to the lysosome. Thus, it was identified that human anti-DLK1 monoclonal antibodies 18A5 and 27F7 were antibodies suitable for antibody-drug conjugates (ADC) for delivering cytotoxic substances into MIA PaCa-2 cells overexpressing DLK1.

Example 3-7. Quantification of Intracellular Internalization of Anti-DLK1 Antibodies Through FACS Assay Anti-DLK1 antibodies 18A5 and 27F7 bound to the surface of MIA PaCa-2 cells overexpressing DLK1, and intercellular internalization thereof was induced. Then, the cells were seeded at a density of 5×10³ cells/well in a 6-well plate, were each treated with 10 µg/ml of anti-DLK1 antibodies 18A5 and 27F7, and were reacted at 4° C. for 1 hour such that the antibody bound to the antigen present on the cell surface. Then, the cells were washed with cold PBS, the medium was replaced with a complete medium pre-warmed to 37° C. to induce intracellular internalization of antibodies, and the cells were incubated under conditions of 37° C. and 5% $CO_2$ for 0, 0.5, 2 or 4 hours. Each hour, the cells were washed with PBS containing cold 10% fetal bovine serum (FBS), scraped with a scraper, centrifuged and cultured in the dark at 4° C. for 0.5 hours using an FITC fluorescence-conjugated anti-human IgG secondary antibody (Vector, USA). Fluorescently stained cells were suspended in 500 µl of PBS containing 10% FBS and analyzed using a FACSCanto™ II flow cytometer (BD Bioscience, USA). Kinetic comparison of the internalization of antibodies was carried out by quantification of anti-DLK1 antibodies remaining on the cell surface by mean fluorescence intensity (MFI). The intracellular internalization rate was calculated as follows.

Intracellular internalization rate (%)=
(1−MFI$_{37°\,C.}$/MIF$_{4°\,C.}$)×100

Figure 13:
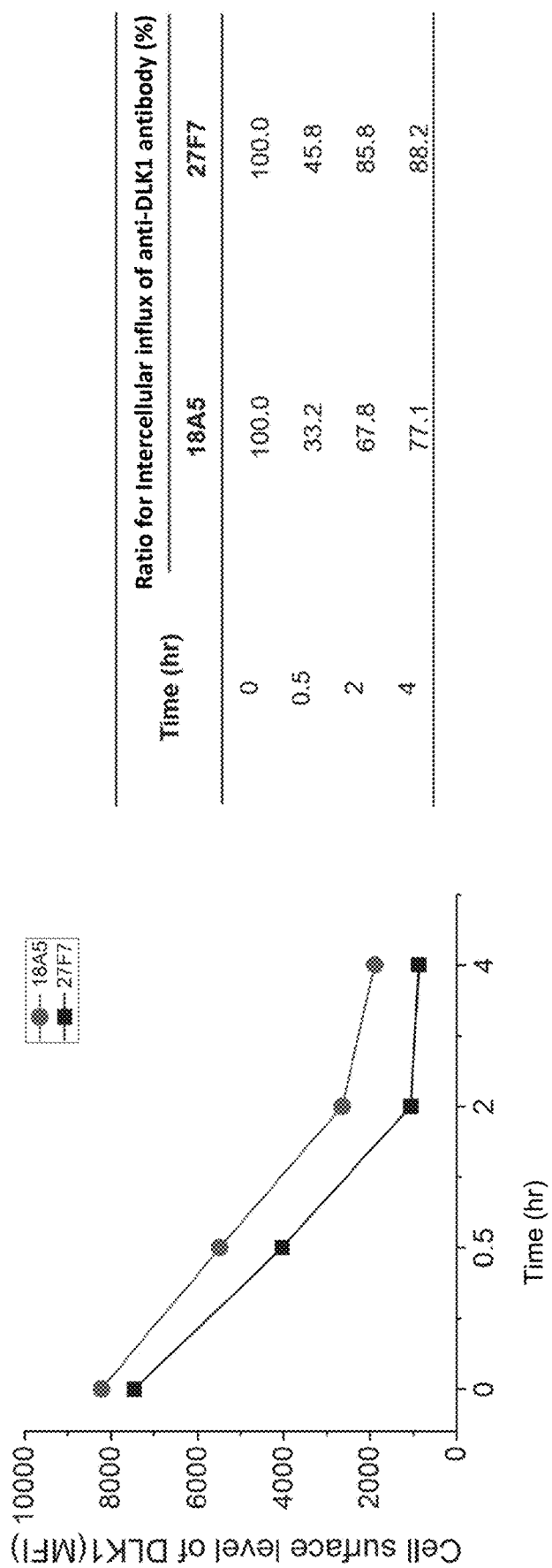
FIG. 13 shows the amount of antibody remaining in the cell membrane after intracellular internalization of human monoclonal antibodies (18A5, 27F7) in MIA PaCa-2 cells overexpressing DLK1 (FACS), quantified as a mean fluorescence intensity (MFI) using a fluorescence-activated cell sorter.

The result identified that two human anti-DLK1 monoclonal antibodies were rapidly internalized into the cell in a time-dependent manner (FIG. 13). 0.5 hours after induction of intercellular internalization, 18A5 was incorporated in an amount of 33.2% and 27F7 was incorporated in an amount of 45.8%, and 4 hours later, 18A5 was incorporated in an amount of 77.1% and 27F7 was incorporated in an amount of 88.2%. Thus, as assessed by the confocal microscopy described above, human anti-DLK1 monoclonal antibodies 18A5 and 27F7 were found to be antibodies suitable for antibody-drug conjugates (ADC) for delivering cytotoxic substances into MIA PaCa-2 cells overexpressing DLK1.

Example 4. Efficacy Test in DLK1-Expressing Cancer Cells

Figure 14:
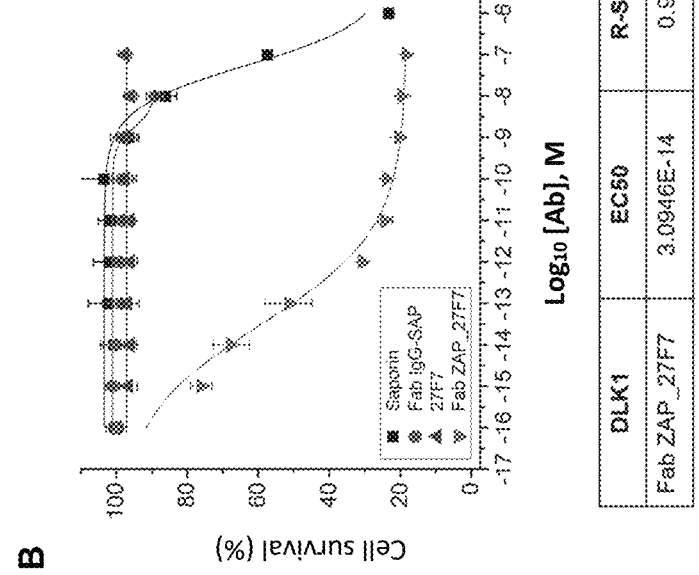
FIG. 14 shows the results (A and B) of identification of the apoptosis effect due to toxin of human monoclonal antibodies (18A5, 27F7) in MIA PaCa-2 cells overexpressing DLK1 (A and B).
Figure 14:
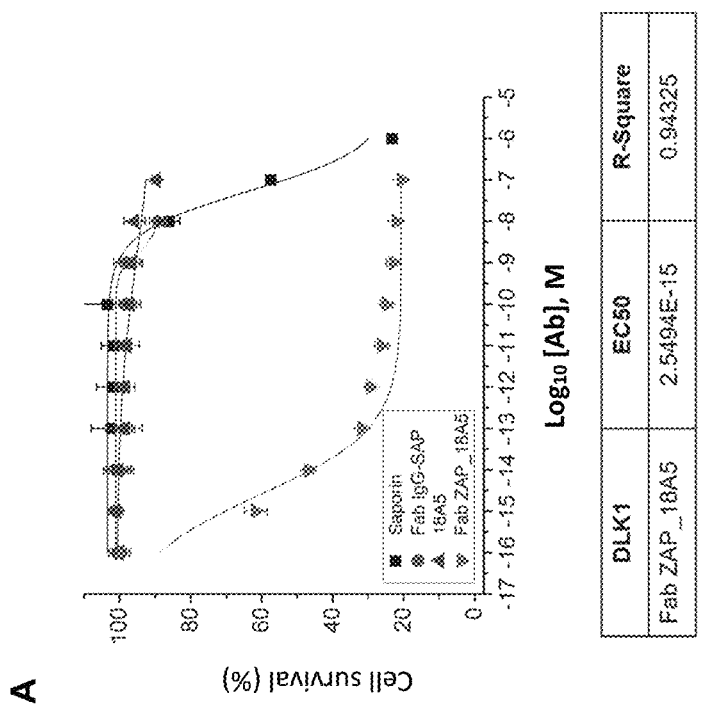

In order to identify potential development into anti-DLK1 antibody-drug conjugates from anti-DLK1 antibodies, cytotoxicity experiments were performed on human anti-DLK1 monoclonal antibodies 18A5 and 27F7 using a ZAP antibody internalization kit (Advance Targeting System, USA) in MIA PaCa-2 cells overexpressing DLK1. The cells were seeded at a density of $2.5 \times 10^3$ cells/well in a 96-well plate (Nunc, USA) and attached thereto for 24 hours, 18A5, 18A5-Fab ZAP or 27F7, 27F7-Fab ZAP were prepared at different concentrations within the range of 1 fM to 10 nM, as shown in FIG. 14, and the cell culture was treated therewith, and was treated with saponin, as a positive control drug, within the range of 1 fM to 1 μM and with IgG-SAP within the range of 1 fM to 100 nM. Then, MIA PaCa-2 cells overexpressing DLK1 were incubated in an incubator under conditions of 37° C. and 5% $CO_2$ for 72 hours and were further incubated in the presence of 50 μl of a XTT/PMS solution for 2 hours, and absorbance at 450 nm was measured using an ELISA reader (Spectra Max5; Molecular Device, USA). In order to compare the cytotoxicity of each sample, the amount of sample required to reach 50% of the maximum effect ($EC_{50}$) was measured.

The result showed that treatment with 18A5 or 27F7 or with IgG-SAP as a negative control drug did not result in the death of cancer cells in MIA PaCa-2 cells over-expressing DLK1 at any concentration, but toxicity to cancer cells of 18A5- or 27F7-Fab ZAP increased as the concentration of the antibody increased, and a cytotoxic effect of about 80% was obtained at a concentration of 10 μM (FIG. 14). In this case, $EC_{50}$ values were 2.5 and 30.1 fM, respectively. On the other hand, saporin, a positive control drug, caused cytotoxicity due to nonspecific intracellular internalization at high concentrations of 100 nM or more.

The results of Example 4 suggest that two human anti-DLK1 monoclonal antibodies (18A5 and 27F7) can be developed as anti-DLK1 antibody-drug conjugates capable of killing cancer cells while targeting DLK1 expressed on the surface of cancer cells.

Example 5. Optimization for Anti-DLK1 18A5 Antibody

Example 5-1. Construction of Libraries for Optimization of Anti-DLK1 18A5 Antibody ("DLK1-18A5 Antibody")

The antibody optimization was conducted by the following three methods including: LC shuffling including constructing new LC shuffling libraries by introducing a $10^5$-$10^6$ light chain (LC) pool owned by Y-Biologics Inc., while the heavy chains; core packing+LC shuffling (FR) including comparatively analyzing with the residues of structurally important sites such as hydrophobic cores of heavy chains, exposed residues, charge clusters and salt bridges, performing mutations with conserved residues and then conducting LC shuffling; and CDR hotspot+LC shuffling (AM), in the case of DNAs in antibody variable regions, including randomly mutating mutational hot spots that can be mutated frequently in the process of in vivo affinity maturation and then conducting LC shuffling.

For the construction of LC shuffling libraries, the LC gene of the 18A5 antibody was cleaved with BstX I and then used as a vector, and the library pool owned by Y-biologics Inc. was cleaved with BstX I and then used as an insert. After ligation with ligase, transformation was performed using the cells for electroporation transformation. The transformed cells were collected in a square plate to construct antibody libraries, and about $1.5 \times 10^7$ various libraries were obtained. The result of sequencing showed that all HC sequences were identical to each other and the LC sequences were different from each other.

For the construction of the core packing+LC shuffling libraries, the framework (FR) portion of the 18A5 antibody was substituted with a conserved amino acid sequence, the LC gene was cleaved with BstX I and then used as a vector, and a library pool owned by Y-biologics Inc. was cleaved with BstX I and then used as an insert. After ligation with ligase, transformation was performed using the cells for electroporation transformation. The transformed cells were collected in a square plate to construct antibody libraries, and about $8.4 \times 10^6$ various libraries were obtained. The result of sequencing showed that the FR portion of HC was substituted with conserved amino acid sequences and the LC sequences were different from each other.

For the construction of CDR hotspot+LC shuffling libraries, the framework (FR) portion of the 18A5 antibody was substituted with a conserved amino acid sequence, the hotspot library of CDR was cleaved with Sfi I and then used as an insert, and a library pool owned by Y-biologics Inc. was cleaved with Sfi I and then used as a vector. After ligation with ligase, transformation was performed using the cells for electroporation transformation. The transformed cells were collected in a square plate to construct antibody libraries, and about $5.6 \times 10^6$ various libraries were obtained. The result of sequencing showed that the FR portion of HC was substituted with conserved amino acid sequence, that the amino acid of the hotspot sequence of CDR was randomly mutated, and that the LC sequences were different from each other.

Example 6. Screening of Human Anti-DLK1 Antibody Variants

Example 6-1. Bio-Panning

Bacteria were infected with the library phage produced for optimization of the DLK1-18A5 antibody and incubated at 30° C. for 16 hours. After incubation, the supernatant was concentrated with PEG and then dissolved in PBS buffer to prepare a human antibody library. Library phages were placed in immune tubes coated with a human DLK1-hFc protein antigen, reacted at room temperature for 2 hours, and washed with 1×PBS/T and 1×PBS, and then only scFv-phages that specifically bind to the antigen were extracted.

A pool of positive phages was obtained through the panning process including infecting *Escherichia coli* the extracted phages again, followed by amplification. Panning for antibody optimization was performed only in the first round. As shown in Table 6, the result showed that the number of phages bound (output) to the antigen in the second round of panning was slightly increased compared to the number of input phages.

TABLE 6

Comparison of titer of antibodies according to panning

| | Number of panning rounds | Number of input phages | Number of bound phages |
|---|---|---|---|
| DLK1-18A5-LS | 1 | $1.3 \times 10^{13}$ | $1.8 \times 10^5$ |
| | 2 | $1.1 \times 10^{13}$ | $4.3 \times 10^8$ |
| DLK1-18A5-FR | 1 | $1.1 \times 10^{13}$ | $3.6 \times 10^6$ |
| | 2 | $1.3 \times 10^{13}$ | $2.8 \times 10^8$ |

TABLE 6-continued

Comparison of titer of antibodies according to panning

| | Number of panning rounds | Number of input phages | Number of bound phages |
|---|---|---|---|
| DLK1-18A5-AM | 1 | $1.1 \times 10^{13}$ | $7.1 \times 10^6$ |
| | 2 | $1.1 \times 10^{13}$ | $4.5 \times 10^8$ |

Example 6-2. Positive Phage Selection

The colonies obtained from panning were cultured at 37° C. for 16 hours using a 1 ml 96-deep well plate in a medium containing 2×YTCM, 2% glucose and 5 mM $MgCl_2$. 100 to 200 µl of the cultured cells were taken such that the $OD_{600}$ value reached 0.1, 1 ml of a medium containing 2×YTCM, 2% glucose and 5 mM $MgCl_2$ was added to a 96-deep well plate, and the cells were cultured at 37° C. for 2 to 3 hours such that the $OD_{600}$ value reached 0.5 to 0.7. The cells were infected with M1 helper phages at a MOI of 1:20 and cultured for 16 hours at 30° C. in a medium containing 2×YTCMK, 5 mM $MgCl_2$ and 1 mM IPTG.

An immuno-96 microwell plate was coated with an antigen DLK1 at 100 ng/well at 4° C. for 16 hours and each well was blocked using a 4% skim milk powder dissolved in PBS and washed with PBS/T, 1 µl of monoclonal scFv-phages (each 100 scFv-phages) incubated for 16 hours were added to each well and reacted at room temperature for 2 hours. After the reaction, each well was washed four times with PBS/T, and then a mouse anti-M13-HRP antibody (UK) as a secondary antibody was diluted to 1/2000, reacted at room temperature for 1 hour and washed with PBS/T, color development was induced and absorbance of 490 nm was measured.

Figure 15:
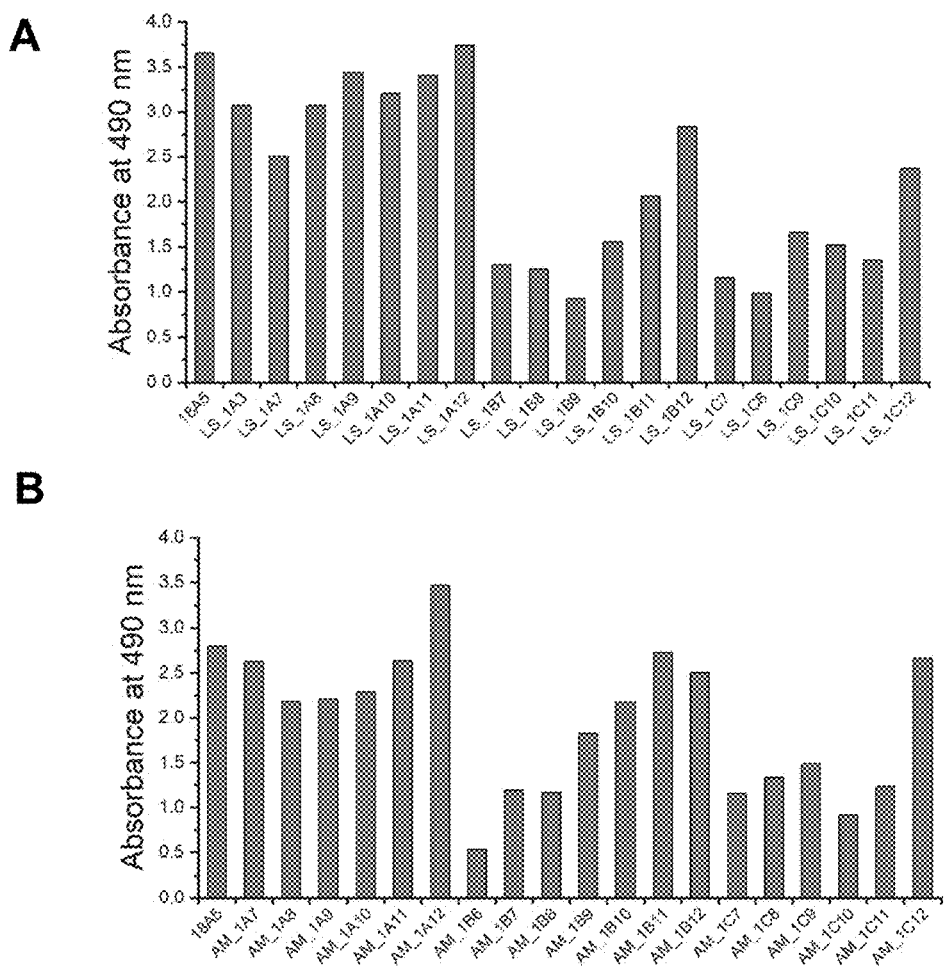
FIG. 15 shows the results of ELISA to determine whether the phage clones respectively expressing a monoclonal scFv as a variant of 18A5 human anti-DLK1 antibody bind to the antigen.

As described above, about 500 antibody clones were analyzed to select mono-phage clones that bind to a DLK1 antigen and the result identified that mono-phage clones having binding affinity stronger than or similar to the parental antibody, DLK1-18A5. For example, results of 38 mono-phage clone analysis are shown in FIG. 15.

Example 6-3. Sequencing of Positive Phage Antibodies

The selected monoclones were subjected to DNA-prep using a DNA purification kit (Qiagen, Germany) to obtain DNA, and sequencing of DNA was requested (SolGent). Based on the results of the sequencing analysis, the CDR regions of $V_H$ and $V_L$ of the selected antibodies were identified, and the similarity between these antibodies and the germ line antibody group was determined using the Ig BLAST program of NCBI's website, http://www.ncbi.nlm-.nih.gov/igblast/. As a result, 44 kinds of specific phage antibodies (LS: 19, FR: 8, AM: 17) having higher or similar antigen-binding capacity compared to the parent antibody (DLK1-18A5) were obtained. As can be seen from the examples described later, two kinds of antibodies 18A5_LS_1A10 and 18A5_AM_1A12 were selected through analysis of cross-reactivity between different species, antigen-binding sites (epitopes), affinity, cell-binding capacity, intracellular internalization, cytotoxic effects in cancer cells and the like, and the characteristics of the two selected monoclones are summarized in Table 7.

TABLE 7

Characteristics of monoclones of human anti-DLK1 antibody variants selected through optimization process

| Clone | VH (Germ line) | Similarity | VL (Germ line) | Similarity | Group |
|---|---|---|---|---|---|
| 18A5 | IGHV3-30 | 82.7% | IGKV1-39 | 84.2% | 1 |
| 18A5_LS_1A10 | IGHV3-30 | 82.7% | IGKV1-39 | 92.6% | 2 |
| 18A5_AM_1A12 | IGHV3-30 | 84.7% | IGKV1-39 | 86.3% | 3 |

The heavy- and light-chain CDRs of the two selected antibodies, the FR sequences, and the antibodies including the heavy-chain variable region and light-chain variable region including the same are shown in Table 8.

TABLE 8

Heavy-chain variable region and light-chain variable region of selected human anti-DLK1 antibody variants

| Clone | FR1 | CDR1 | FR2 | CDR2 | FR3 | CDR3 | FR4 | SEQ ID NO |
|---|---|---|---|---|---|---|---|---|
| 18A5_LS_1A10-HC | QVQLVQSGGAVVQPGHSLRLSCEAS | GFKFKDYG | MHWVRQAPGKGLEWLAV | ISHDGRNK | NYADSVKGRLTISRDNSKNTLSFQMNSLRAEDTAVYYC | VRDWSYAFDI | WGQGTLVTVSS | 101 |
| SEQ ID NO | 15 | 16 | 17 | 18 | 19 | 20 | 21 | |
| 18A5_LS_1A10-LC | DIQMTQSPSSLSASLGDRVTITCRAS | QGISSA | LAWYQQKPGKAPKLLIY | AAS | SLQSGVPSRFSGSGSGTDFTLTINSLQPEDFATYYC | QQSYTTPLT | FGGGTKVEIK | 126 |
| SEQ ID NO | 117 | 115 | 24 | 95 | 118 | 116 | 28 | |
| 18A5_AM_1A12-HC | QVQLVQSGGGVVQPGHSLRLSCAAS | GFKFKDYG | MHWVRQAPGKGLEWLAV | ISHDGRNK | NYADSVKGRLTISRDNSKNTLSFQMNSLRAEDTAVYYC | VRDWSYAFDI | WGQGTLVTVSS | 127 |
| SEQ ID NO | 119 | 16 | 17 | 18 | 19 | 20 | 21 | |

TABLE 8-continued

Heavy-chain variable region and light-chain variable region of selected human anti-DLK1 antibody variants

| Clone | FR1 | CDR1 | FR2 | CDR2 | FR3 | CDR3 | FR4 | SEQ ID NO |
|---|---|---|---|---|---|---|---|---|
| 18A5_AM_1A12-LC | DIQMTQSPS FLSASVGDR VTITCRAS | HDISS | LAWY QQKS GKAP KLLI Y | SAS | NLKSGVPSR FSGSGSGTD FSLTISSLQP EDFATYYC | QQSYT TVLT | FGGG TKLEI K | 128 |
| SEQ ID NO | 120 | 121 | 122 | 39 | 123 | 124 | 125 | |

Example 7. Production of Human Anti-DLK1 Antibody Variants

Production of the two selected 18A5 antibody variants was carried out using the same procedure described in connection with Example 2-3. Each vector including the cloned heavy and light chains was co-transfected into animal transient expression cells HEK-293E, expressed and then purified by protein A affinity chromatography to determine the yield, and SDS-PAGE analysis was performed under reducing and non-reducing conditions to determine protein purity and mobility.

Figure 16:
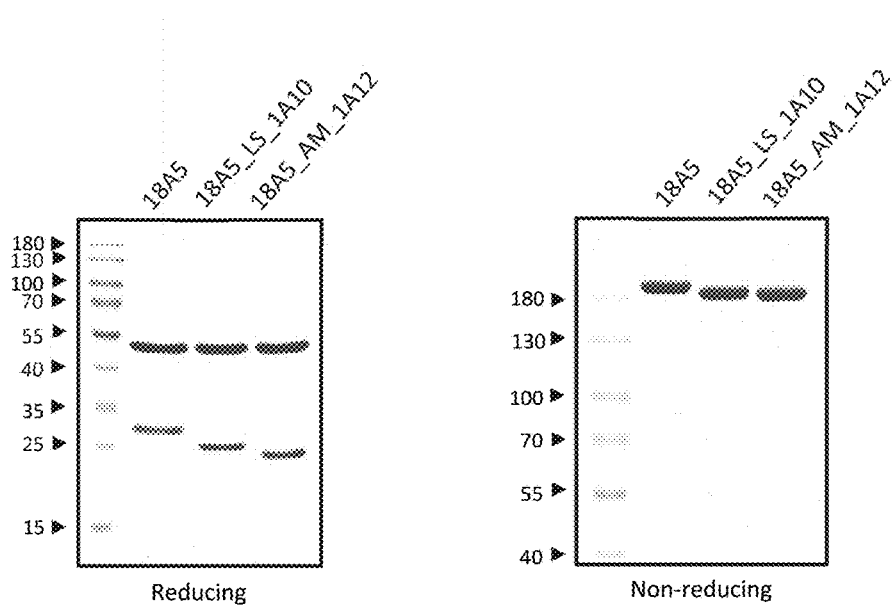
FIG. 16 shows the purity of antibodies, analyzed through SDS-PAGE in reducing or non-reducing conditions, after conversion of two phage antibodies selected from 18A5 antibody variants from scFv to IgG.

As shown in FIG. 16, the result showed that all of the DLK1-18A5 antibody variants LS_1A10 and AM_1A12 were detected at a size of 150 kDa or more under non-reducing conditions, purity was 95% or more, and yields were 127.4 mg/L and 168.5 mg/L, respectively.

Example 8. Characteristics of Human Anti-DLK1 Monoclonal Antibody Variants

Example 8-1. Determination of Cross-Reactivity of Selected Human Anti-DLK1 Monoclonal Antibody Variants The binding capacity of the human anti-DLK1 antibody was determined through ELISA using human anti-DLK1 antibody with the same mouse DLK1 and monkey DLK1 proteins as in FIG. 7 in order to determine cross-reactivity to DLK1 orthologues found in other species of human anti-DLK1 monoclonal antibody variants.

Figure 17:
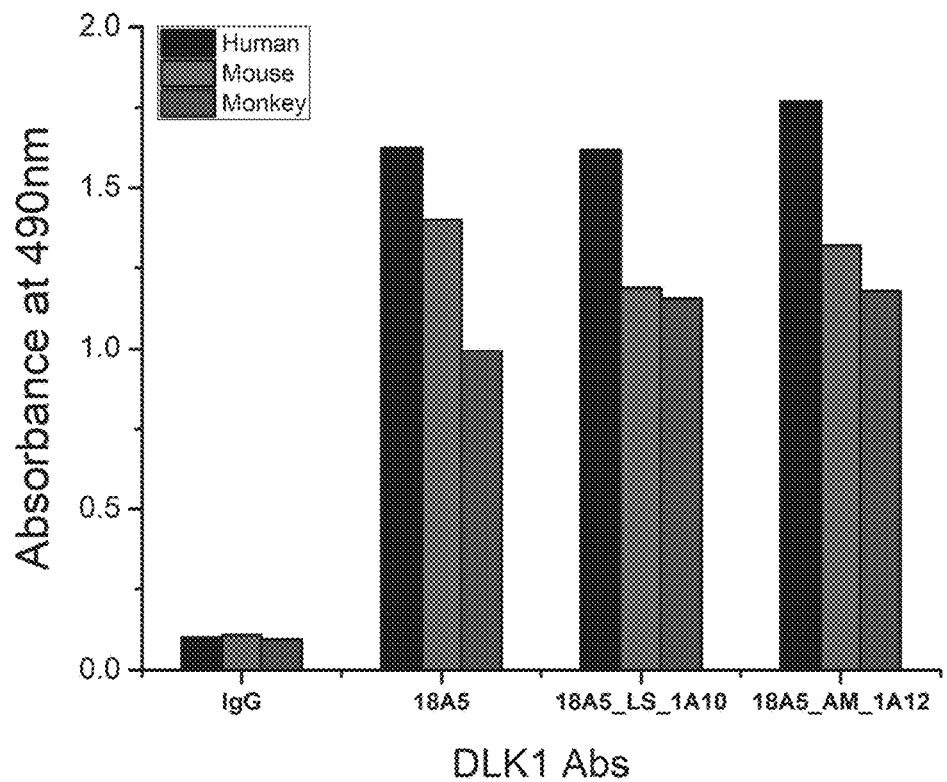
FIG. 17 shows the result of ELISA to determine cross-reactivity of the human anti-DLK1 monoclonal antibody variants, 18A5_LS_1A10 and 18A5_AM_1A12, with the hFc fusion protein of human DLK1 (hDLK1), mouse DLK1 (mDLK1), or monkey DLK1 (MDLK1).

The result showed that the anti-DLK1 antibody variants 18A5_LS_1A10 and 18A5_AM_1A12 bound to the same human DLK1, mouse DLK1 and monkey DLK1 as the parent antibody 18A5 (FIG. 17).

Example 8-2. Determination of Binding Sites (Epitopes) to DLK1 Antigens of Selected Human Anti-DLK1 Monoclonal Antibody Variants ELISA was performed for human anti-DLK1 antibody variants with the same four human-derived DLK1 recombinant proteins and hFc recombinant proteins as in FIG. 6 in order to determine binding sites (epitopes) to DLK1 antigens of selected human anti-DLK1 monoclonal antibody variants.

Figure 18:
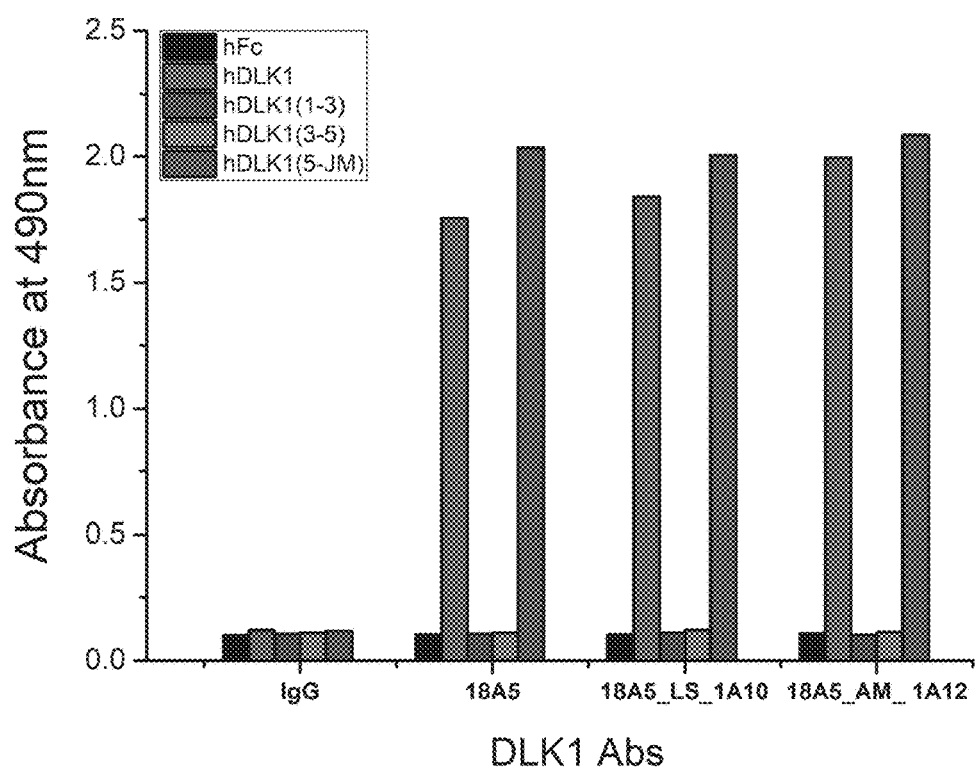
FIG. 18 shows the result of ELISA to determine the binding specificity of two kinds of human anti-DLK1 monoclonal antibody variants, namely, 18A5_LS_1A10 and 18A5_AM_1A12, to an hFc protein (negative control group) and a DLK1-hFc fusion protein including a full-length or partial-length EGF-like repeat domain.

The result showed that the anti-DLK1 antibody variants 18A5_LS_1A10 and 18A5_AM_1A12 had binding sites in the same EGF-like repeat domain 6 and membrane proximity domain as the parent antibody 18A5 (FIG. 18).

Figure 19:
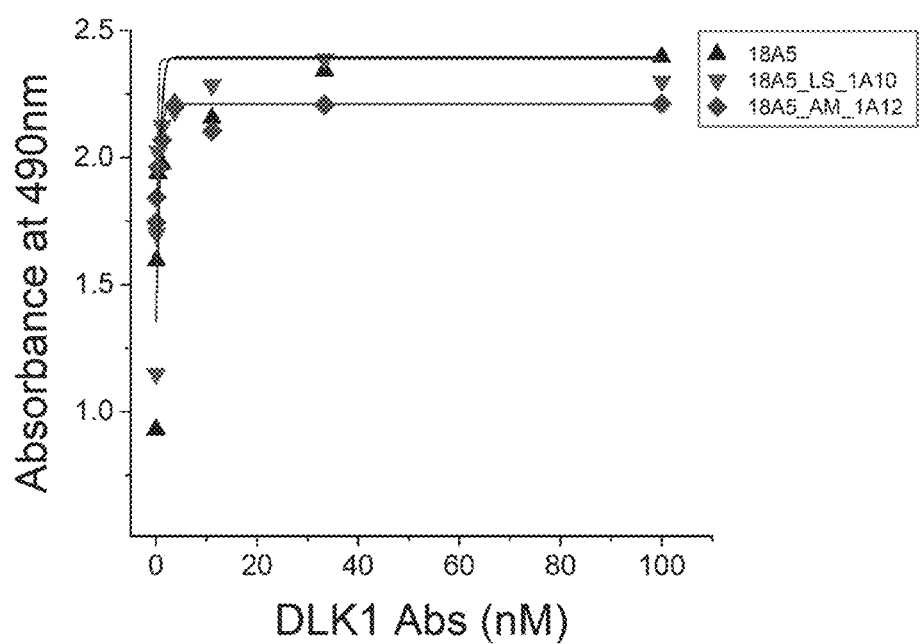
FIG. 19 shows the result of ELISA to determine binding affinity of the DLK1 single human antibody variant antibodies, 18A5_LS_1A10 and 18A5_AM_1A12 to the DLK1 antigen and kinetic constants thereof.

Example 8-3. Determination of Affinity to Antigen of Selected Human Anti-DLK1 Monoclonal Antibody Variants The binding affinity to the antigen of the selected human anti-DLK1 monoclonal antibody variants was measured using an ELISA method, which was the same as the phage-ELISA method described in Example 2-2 above, except that, instead of phages, the selected human anti-DLK1 monoclonal antibody variants were serially diluted by one-third from 100 nM to 0.046 nM and each added sequentially in an amount of 100 μl to a well column. The measurement results were analyzed using GraphPad Prism 6 software (http://www.graphpad.com/scientific-software/prism/). The affinity dissociation constants (Kd) for the antigens of human anti-DLK1 monoclonal antibodies 18A5_LS_1A10 and 18A5_AM_1A12 were 0.047 and 0.013 nM, respectively (FIG. 19).

Example 8-4. Determination of Binding Capacity to DLK1 Present on Cell Surface Through FACS Analysis FACS analysis was performed in order to compare the binding capacity of the human anti-DLK1 18A5 antibody and its variants, 18A5_LS_1A10 and 18A5_AM_1A12, to the surface of the DLK1-overexpressing human pancreatic cancer cell line, MIA PaCa-2 cells. $5 \times 10^5$ cells were prepared, and the human anti-DLK1 18A5 antibody and its variant antibodies, 18A5_LS_1A10 and 18A5_AM_1A12, as primary antibodies, were serially diluted at ⅓ from a concentration of 10 μg/ml and bound to the cells at 4° C. for 1 hour. Then, the cells were washed with cold PBS and then cultured at 4° C. for 1 hour using an anti-human IgG secondary antibody (Vector, USA) conjugated with fluorescein isothiocyanate (FITC, Vector, USA) fluorescence. Fluorescently stained cells were suspended in 500 μl of PBS containing 2% FBS (fetal bovine serum) and analyzed using a FACSCanto™ II flow cytometer (BD Biosciences, USA) and the amount of sample required to reach 50% of the maximum effect ($EC_{50}$) was measured.

Figure 20:
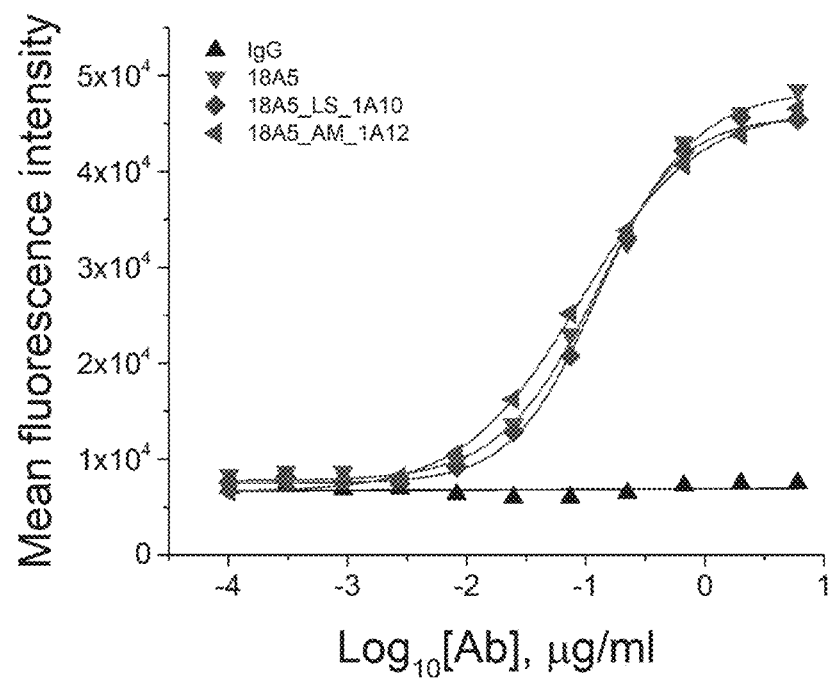
FIG. 20 shows the result of fluorescence-activated cell sorting (FACS) to identify whether DLK1 single human antibody variant antibodies, namely 18A5_LS_1A10 and 18A5_AM_1A12, have concentration-dependent binding capacity to MIA PaCa-2 cells overexpressing DLK1.

The result showed that the amount ($EC_{50}$) of human anti-DLK1 18A5 antibody and its variant antibodies 18A5_LS_1A10 and 18A5_AM_1A12 bound to MIA PaCa-2 overexpressing DLK1 was 130.7 ng/ml for 18A5, 120 ng/ml for 18A5_LS_1A10, and 90.3 ng/ml for 18A5_AM_1A, indicating that all had similar binding capacity (FIG. 20).

Example 8-5. Identification of Binding Specificity of Selected Human Anti-DLK1 Monoclonal Antibody Variants to DLK1 Antigens Present on Cell Surface MIA PaCa-2 cells overexpressing DLK1 on the cell surface and SK-N-F1 cells endogenously expressing DLK1 were each treated with 20 nM DLK1 siRNA (siDLK1, Dharmacon, USA) or shRNA (shDLK1, Sigma, USA) to reduce the expression of DLK1, and then the binding specificity of the human anti-DLK1 18A5 monoclonal antibody variants to the antigen was measured through the difference in cell binding between the antibodies. The cell binding of the antibody was determined through FACS analysis. Each cell was prepared in an amount of $5 \times 10^5$ and reacted with human anti-DLK1 monoclonal antibody variants 18A5_LS_1A10 and 18A5_AM_1A12 at a concentration of 2 µg/ml at 4° C. for 1 hour. Then, the cells were washed with cold PBS and then cultured at 4° C. for 1 hour using an anti-human IgG secondary antibody (Vector, USA) conjugated with fluorescein isothiocyanate (FITC, Vector, USA) fluorescence. Fluorescently stained cells were suspended in 500 µl of PBS containing 2% FBS (fetal bovine serum) and analyzed using a FACSCanto™ II flow cytometer (BD Biosciences, USA).

Figure 21:
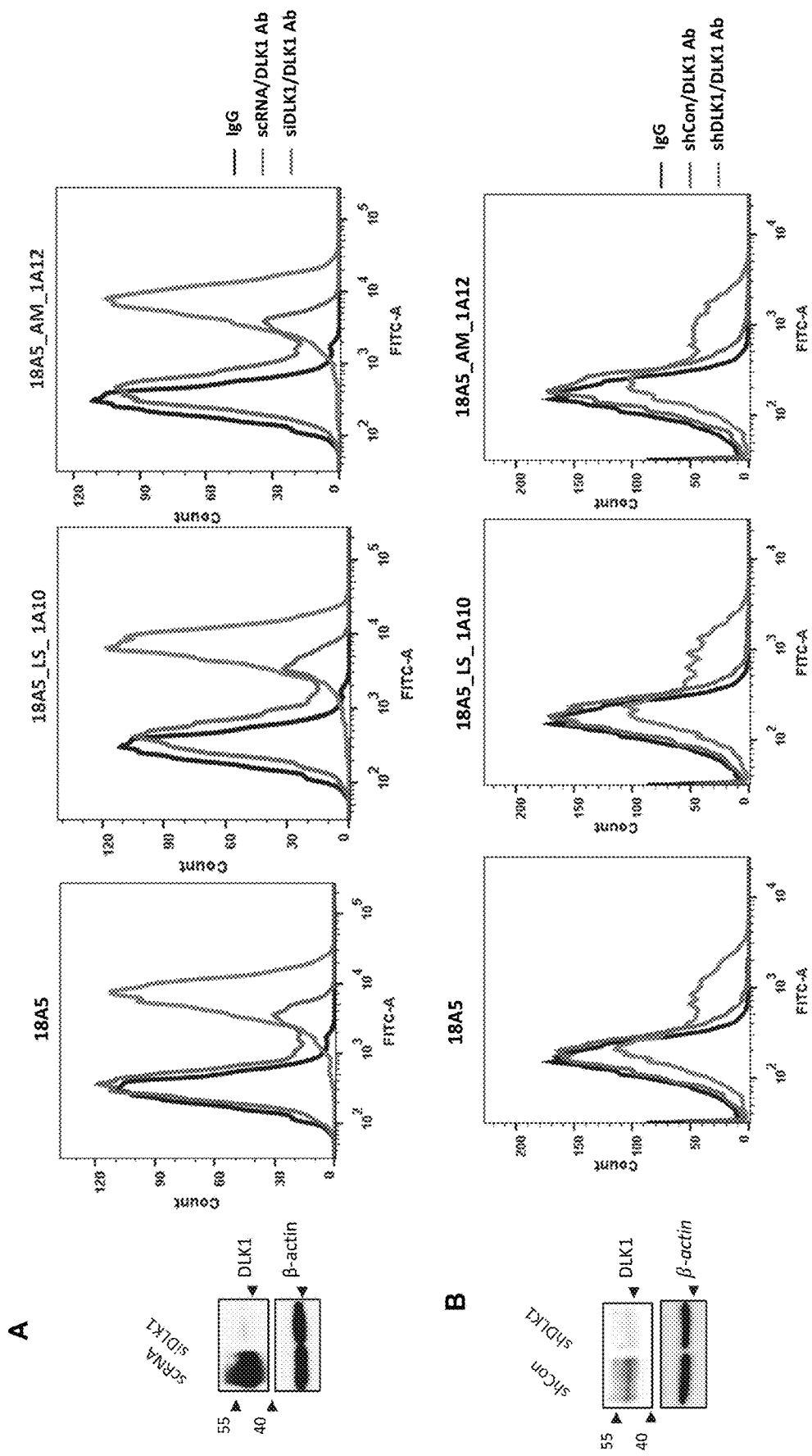
FIG. 21 shows a decrease in DLK1 protein expression, identified by treating DLK1-overexpressed MIA PaCa-2 cells with siRNA (A) or by treating SK-N-F1 cells endogenously expressing DLK1 with siRNA (B) and further shows the antigen-binding specificities of 18A5_LS_1A10 and 18A5_AM_1A12, which are human anti-DLK1 monoclonal antibody variants, identified with a fluorescence soluble cell sorter (FACS), wherein scRNA represents scrambled small interfering RNA (siRNA), siDLK1 represents DLK1-specific siRNA, shCon represents control short hairpin RNA (shRNA) and shDLK1 represents DLK1-specific shRNA.

The result showed that, when treating MIA PaCa-2 cells (FIG. 21A) overexpressing DLK1 and SK-N-F1 cells (FIG. 21B) endogenously expressing DLK1 with DLK1 siRNA or shRNA, compared to the control group (scRNA or shCon) upon Western blotting, both resulting types of cells exhibited an at least 95% decrease in DLK1 expression, and the cell binding of the human anti-DLK1 monoclonal antibody variants 18A5_LS_1A10 and 18A5_AM_1A12 was also decreased upon FACS analysis. This result suggests that the 18A5_LS_1A10 and 18A5_AM_1A12 antibodies specifically bind to the DLK1 antigen.

Example 9. Determination of Activity of Selected Human Anti-DLK1 Antibody Variants

Example 9-1. Determination of Intracellular Internalization (Endocytosis) of Selected Human Anti-DLK1 Antibody Variants Through IncuCyte Assay The intracellular internalization of the anti-DLK1 antibody 18A5 and its variant antibodies 18A5_LS_1A10 and 18A5_AM_1A12 was determined by conjugating each antibody with IncuCyte® FabFluor human red fluorescent reagent (Essen Bioscience, USA), treating, with the resulting conjugate, DLK1-overexpressing MIA PaCa-2 cells having a high expression rate, SK-N-F1 cells having a normal expression rate and HepG2 cells having a low expression rate, and monitoring the amount of each antibody internalized into the cells over time. DLK1-overexpressing MIA PaCa-2 cells (at a density of $1 \times 10^4$ cells/well) and SK-N-F1 or HepG2 cells (at a density of $4 \times 10^4$ cells/well) were seeded into a 96-well plate (Nunc, USA) and attached thereto for 24 hours, 4 µg/ml of each antibody was mixed with the equivalent amount of InCucyte® FabFluor red antibody labeling reagent and reacted in the dark at 37° C. for 15 minutes, and then the cells were treated therewith. As the intracellular internalization of the antibody, the amount of each antibody accumulated in the lysosomes of the cells over time was determined using an IncuCyte ZOOM HD/2CLR System (Essen Biosciences, USA) and quantified at 15-minute intervals for 24 hours.

Figure 22:
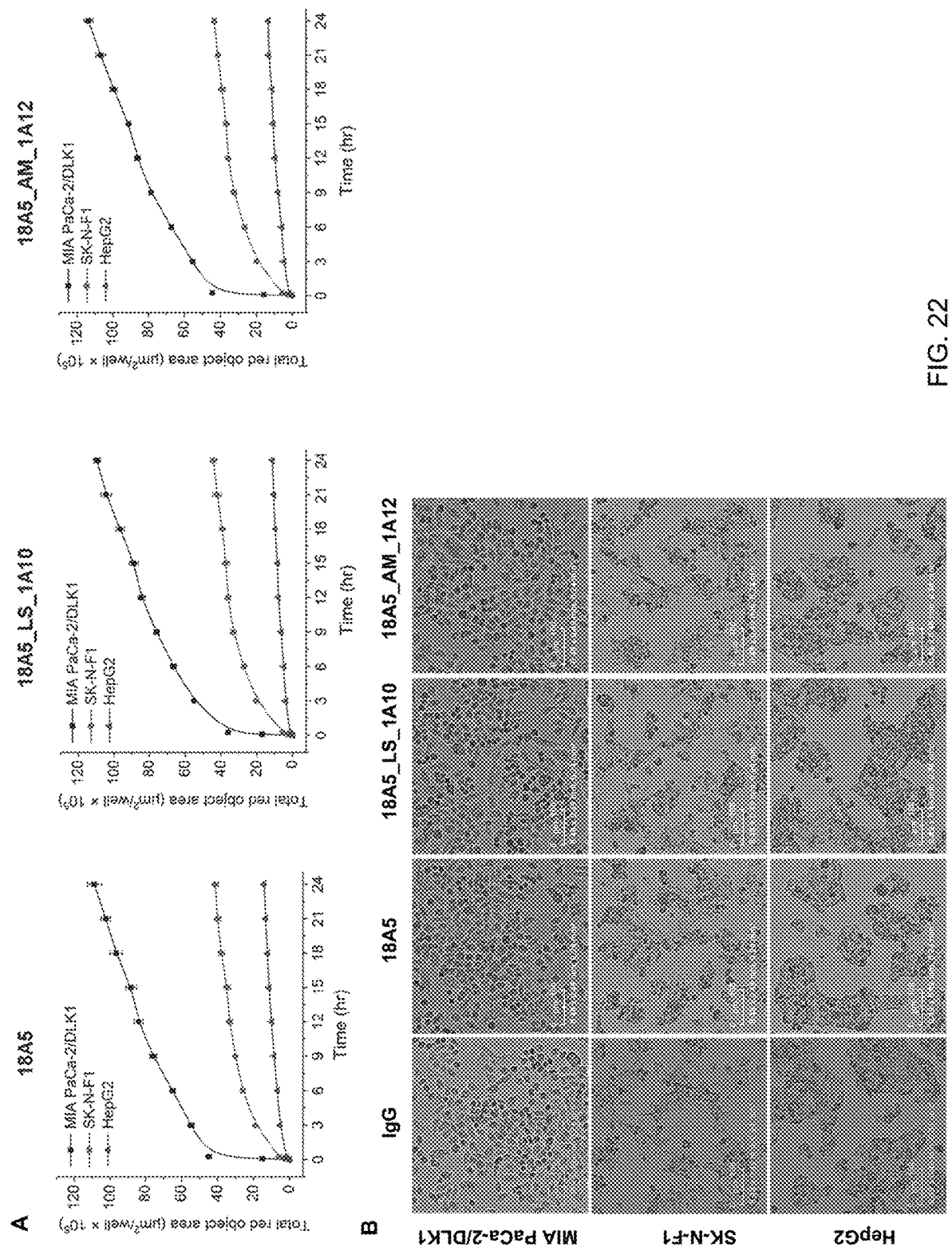
FIG. 22 shows the result of use of an IncuCyte ZOOM HD/2CLR system to identify the internalization of antibodies into cells over time (A) and the amount of antibodies accumulated in cells for 24 hours after treating MIA PaCa-2 cells overexpressing DLK1, and SK-N-F1 or HepG2 cells endogenously expressing DLK1 with human anti-DLK1 monoclonal antibody variants, 18A5_LS_1A10 and 18A5_AM_1A12.

The result showed that 50% of human anti-DLK1 18A5 antibody and its variant antibodies 18A5_LS_1A10 and 18A5_AM_1A12 bound to the cell surface were internalized into DLK1-overexpressing MIA PaCa-2 cells within one hour and into SK-N-F1 and HepG2 cells within 3 hours (FIG. 22A). The antibodies exhibited a difference in the degree of intracellular internalization depending on the extent of DLK1 expression on the cell surface. In addition, the accumulated amount of antibody internalized into the cells after 24 hours was similar for the same cells (FIG. 22B).

The results suggest that the 18A5_LS_1A10 and 18A5_LS_1A12 antibodies, like the anti-DLK1 antibody 18A5, are both considered to be antibodies capable of delivering drugs into cells and can be developed as anti-DLK1 antibody-drug conjugates.

Example 9-2. Test on Cancer-Cell-Killing Efficacy of Selected Human Anti-DLK1 Antibody Variants The possibility of developing ADC (antibody-drug conjugate) from human anti-DLK1 18A5 monoclonal antibody variants, 18A5_LS_1A10 and 18A5_AM_1A12 antibodies was determined using DLK1-overexpressing MIA PaCa-2 cells and a ZAP antibody internalization kit (Advance Targeting System, USA) as in Example 4, and cytotoxicity experiments were performed in the same manner and compared with the 18A5 antibody.

Figure 23:
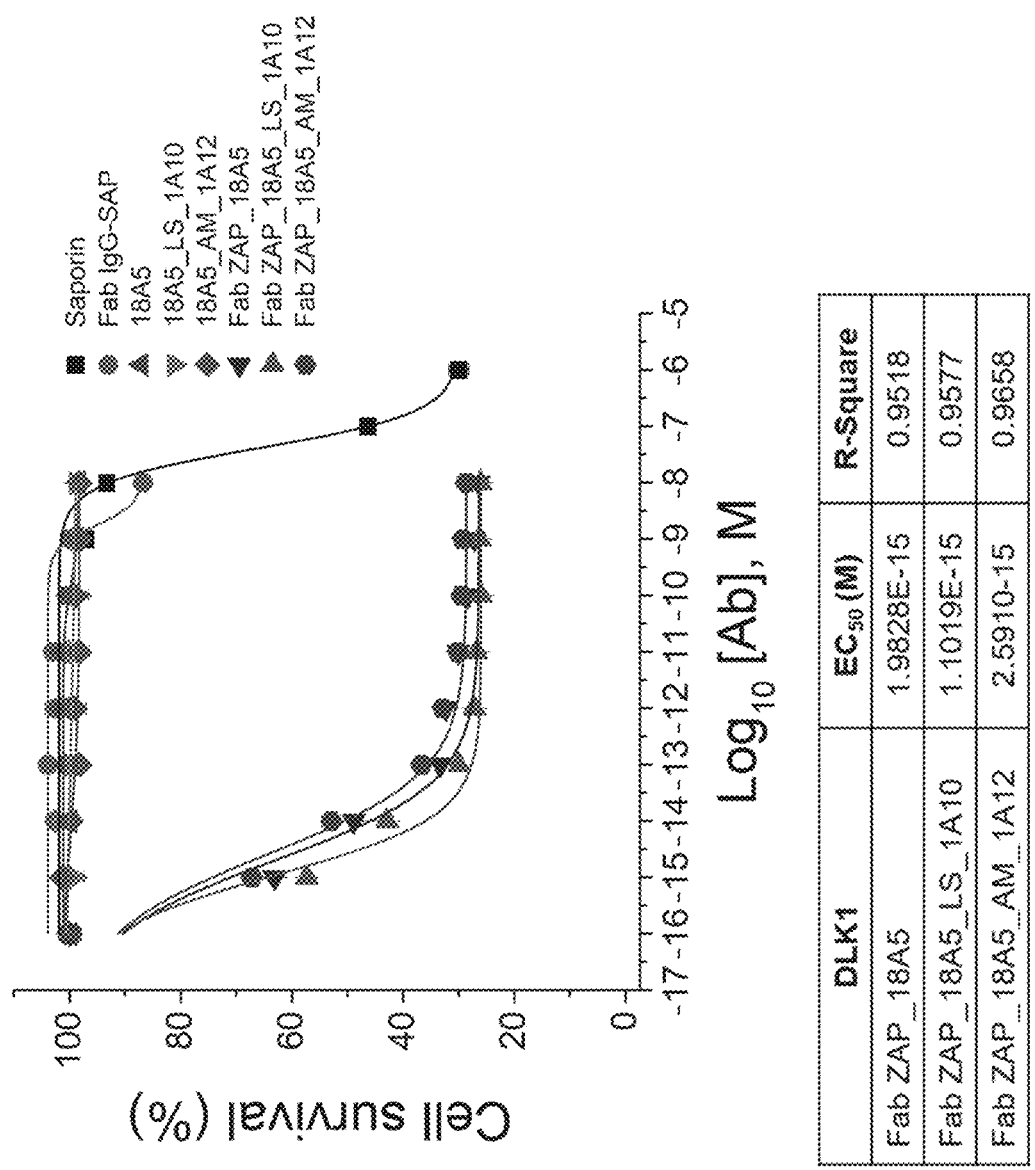
FIG. 23 shows the cytotoxic effect by toxins of human anti-DLK1 monoclonal antibody variants 18A5_LS_1A10 and 18A5_AM_1A12 in DLK1-overexpressing MIA PaCa-2 cells.

The result showed that treatment with 18A5, 18A5_LS_1A10 or 18A5_AM_1A12 antibody or negative control drug IgG-SAP did not result in the death of cancer cells in DLK1-overexpressing MIA PaCa-2 cells at any concentration, whereas toxicity to cancer cells of 18A5-, 18A5_LS_1A10- or 18A5_AM_1A12-Fab ZAP exhibited a cytotoxic effect in a concentration-dependent manner as the antibody concentration increased (FIG. 23). At this time, $EC_{50}$ values of these antibodies were 2.0, 1.1, and 2.6 fM, respectively, and among them, 18A5_LS_1A10-Fab ZAP exhibited slightly superior efficacy. A positive control drug, Saporin, caused cytotoxicity due to nonspecific intercellular internalization at high concentrations of 100 nM or more.

The results of FIG. 23 show that the 18A5_LS_1A10 and 18A5_AM_1A12 antibodies, including the human anti-DLK1 18A5 monoclonal antibody, can be developed as anti-DLK1 antibody-drug conjugates capable of killing cancer cells while targeting DLK1 expressed on the surface of cancer cells.

INDUSTRIAL APPLICABILITY

The anti-DLK1 antibody or antigen-binding fragment thereof according to the present invention exhibits excellent binding capacity to DLK1 and can be useful for the prevention or treatment of cancer. In addition, the antibody-drug conjugate including the same exhibits potent cytotoxic activity against cancer cells expressing DLK1, and the anti-DLK1 antibody or antigen-binding fragment thereof according to the present invention is expected to be useful as an antibody for ADC.

Although specific configurations of the present invention have been described in detail, those skilled in the art will appreciate that this description is provided to set forth preferred embodiments for illustrative purposes and should not be construed as limiting the scope of the present invention. Therefore, the substantial scope of the present invention is defined by the accompanying claims and equivalents thereto.

[Sequence Listing Free Text]
An electronic file is attached.

The invention claimed is:

1. An antibody or an antigen-binding fragment thereof specifically binding to delta-like 1 homolog (DLK1), comprising the following heavy-chain variable region and light-chain variable region:
   a heavy-chain variable region comprising heavy-chain CDR1 of SEQ ID. NO: 16, heavy-chain CDR2 of SEQ ID. NO: 18, heavy-chain CDR3 of SEQ ID. NO: 20, a light-chain variable region comprising light-chain CDR1 of SEQ ID. NO: 23, light-chain CDR2 of SEQ ID. NO: 25, light-chain CDR3 of SEQ ID. NO: 27,
   a heavy-chain variable region comprising heavy-chain CDR1 of SEQ ID. NO: 72, heavy-chain CDR2 of SEQ ID. NO: 74, heavy-chain CDR3 of SEQ ID. NO: 76, a light-chain variable region comprising light-chain CDR1 of SEQ ID. NO: 79, light-chain CDR2 of SEQ ID. NO: 81, light-chain CDR3 of SEQ ID. NO: 83,
   a heavy-chain variable region comprising heavy-chain CDR1 of SEQ ID. NO: 16, heavy-chain CDR2 of SEQ ID. NO: 18, heavy-chain CDR3 of SEQ ID. NO: 20, a light-chain variable region comprising light-chain CDR1 of SEQ ID. NO: 115, light-chain CDR2 of SEQ ID. NO: 95, light-chain CDR3 of SEQ ID. NO: 116, or
   a heavy-chain variable region comprising heavy-chain CDR1 of SEQ ID. NO: 16, heavy-chain CDR2 of SEQ ID. NO: 18, heavy-chain CDR3 of SEQ ID. NO: 20, a light-chain variable region comprising light-chain CDR1 of SEQ ID. NO: 121, light-chain CDR2 of SEQ ID. NO: 39, light-chain CDR3 of SEQ ID. NO: 124.

2. The antibody or an antigen-binding fragment thereof according to claim 1, comprising:
   heavy chain FR1 selected from the group consisting of SEQ ID NOS: 1, 15, 29, 43, 57, 71, 85, and 119;
   heavy chain FR2 selected from the group consisting of SEQ ID NOS: 3, 17, 31, 45, 59, 73, and 87;
   heavy chain FR3 selected from the group consisting of SEQ ID NOS: 5, 19, 33, 47, 61, 75, and 89;
   heavy chain FR4 selected from the group consisting of SEQ ID NOS: 7, 21, 35, 49, 63, 77, and 91;
   light chain FR1 selected from the group consisting of SEQ ID NOS: 8, 22, 36, 50, 64, 78, 92, 117, and 120;
   light chain FR2 selected from the group consisting of SEQ ID NOS: 10, 24, 38, 52, 66, 80, 94, and 122;
   light chain FR3 selected from the group SEQ ID NOS: 12, 26, 40, 54, 68, 82, 96, 118, and 123; or
   light chain FR4 selected from the group consisting of SEQ ID NO: 14, 28, 42, 56, 70, 84, 98, and 125.

3. The antibody or an antigen-binding fragment thereof according to claim 1, comprising a heavy-chain variable region having a sequence selected from the group consisting of SEQ ID NOS: 101, 109, and 127.

4. The antibody or an antigen-binding fragment thereof according to claim 1, comprising a light-chain variable region having a sequence selected from the group consisting of SEQ ID NOS: 102, 110, 126, and 128.

5. A nucleic acid encoding the antibody or an antigen-binding fragment thereof according to claim 1.

6. An expression vector comprising the nucleic acid according to claim 5.

7. A cell transformed with the expression vector according to claim 6.

8. A method of producing an antibody or an antigen-binding fragment thereof specifically binding to DLK1 comprising:
  (a) culturing the cells according to claim 7; and
  (b) recovering an antibody or an antigen-binding fragment thereof from the cell culture.

9. An antibody-drug conjugate (ADC) comprising the antibody or an antigen-binding fragment thereof according to claim 1, and a drug.

10. The antibody-drug conjugate (ADC) according to claim 9, wherein the drug is selected from the group consisting of cytotoxins, radioisotopes, antiproliferative agents, pro-apoptotic agents, chemotherapeutic agents, and therapeutic nucleic acids.

11. A pharmaceutical composition comprising, as an active ingredient, the antibody or an antigen-binding fragment thereof according to the antibody-drug conjugate according to claim 9.

12. A bispecific antibody comprising the antibody or an antigen-binding fragment thereof according to claim 1.

13. A pharmaceutical composition comprising, as an active ingredient, the antibody or an antigen-binding fragment thereof according to the bispecific antibody according to claim 12.

14. A pharmaceutical composition comprising, as an active ingredient, the antibody or an antigen-binding fragment thereof according to claim 1.

15. A chimeric antigen receptor (CAR) comprising the antibody or an antigen-binding fragment thereof according to claim 1 as an antigen-binding domain.

16. A T-cell engager comprising the antibody or an antigen-binding fragment thereof according to claim 1, specifically binding to DLK1 expressed in tumor cells.

17. The antibody or an antigen-binding fragment thereof according to claim 1, comprising
  a heavy-chain variable region including a sequence of SEQ ID NO: 101, and a light-chain variable region including a sequence of SEQ ID NO: 102,
  a heavy-chain variable region including a sequence of SEQ ID NO: 109, and a light-chain variable region including a sequence of SEQ ID NO: 110,
  a heavy-chain variable region including a sequence of SEQ ID NO: 101, and a light-chain variable region including a sequence of SEQ ID NO: 126, or
  a heavy-chain variable region including a sequence of SEQ ID NO: 127, and a light-chain variable region including a sequence of SEQ ID NO: 128.

* * * * *